United States Patent
Snijders et al.

(10) Patent No.: US 10,876,167 B2
(45) Date of Patent: Dec. 29, 2020

(54) 12-GENE PROGNOSTIC SIGNATURE FOR BREAST CANCER SURVIVAL

(71) Applicant: The Regents of the University of California, Oakland, CA (US)

(72) Inventors: Antoine M. Snijders, Antioch, CA (US); Xuan Yu Mao, Moraga, CA (US); Matthew J. Lee, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 414 days.

(21) Appl. No.: 15/870,693

(22) Filed: Jan. 12, 2018

(65) Prior Publication Data

US 2018/0320237 A1  Nov. 8, 2018

Related U.S. Application Data

(60) Provisional application No. 62/445,256, filed on Jan. 12, 2017.

(51) Int. Cl.
  *C12Q 1/6886*  (2018.01)
  *G16B 5/00*   (2019.01)

(52) U.S. Cl.
  CPC ............. *C12Q 1/6886* (2013.01); *G16B 5/00* (2019.02); *C12Q 2600/118* (2013.01); *C12Q 2600/158* (2013.01)

(58) Field of Classification Search
  CPC ............................... C12Q 1/6886; G16B 5/00
  See application file for complete search history.

(56) References Cited

PUBLICATIONS

Hong et al., "Down-regulation of tensin2 enhances tumorigenicity and is associated with a variety of cancers." Oncotarget, vol. 7, No. 25, pp. 38143-38153 (2016).
Xue et al., "CREBRF is a potent tumor suppressor of glioblastoma by blocking hypoxia-induced autophagy via the CREB3/ATG5 pathway. International journal of oncology." vol. 49, No. 2, pp. 519-528 (2016).
Miller et al., "An iron regulatory gene signature predicts outcome in breast cancer." Cancer research. vol. 71, No. 21, pp. 6728-6737 (2011).
Wang et al., "Endothelial Nitric Oxide Synthase Traffic Inducer (NOSTRIN) is a Negative Regulator of Disease Aggressiveness in Pancreatic Cancer. Clinical cancer research : an official journal of the American Association for Cancer Research," vol. 22, pp. 5992-6001 (2016).
Wilson et al., "Death of HT29 adenocarcinoma cells induced by TNF family receptor activation is caspase-independent and displays features of both apoptosis and necrosis. Cell death and differentiation." vol. 9, No. 12, 1321-1333 (2002).
Nakayama et al., "TWEAK-induced cell death. Journal of immunology." vol. 168, No. 2, pp. 734-743 (2002).
Schneider et al., "TWEAK can induce cell death via endogenous TNF and TNF receptor 1." European journal of immunology. vol. 29, No. 6, 1785-1792 (1999).
Gu et al., "Functional expression of TWEAK and the receptor Fn14 in human malignant ovarian tumors: possible implication for ovarian tumor intervention," PLOS One, vol. 8, No. 3, e57436 (2013).
Wang et al., "Nucleic acids research." vol. 41 (Web Server issue) pp. W77-W83 (2013).
Zhang et al., "WebGestalt: an integrated system for exploring gene sets in various biological contexts." Nucleic acids research. vol. 33 (Web Server issue) pp. W741-W748 (2005).
Cerami et al., "The cBio cancer genomics portal: an open platform for exploring multidimensional cancer genomics data." Cancer discovery. vol. 2, No. 5, pp. 401-404 (2012).
Gao et al., "Integrative analysis of complex cancer genomics and clinical profiles using the cBioPortal," Science signaling, vol. 6, No. 269, p. 11 (2013).
DeSantis et al., Breast cancer statistics, 2013. CA: a Cancer Journal for Clinicians. vol. 64, No. 1, pp. 52-62 (2014).
Siegel et al., A. Cancer statistics, 2014. CA: a Cancer Journal for Clinicians. vol. 64, No. 1, pp. 9-29 (2014).
Holloway et al., "Technology as a force for improved diagnosis and treatment of breast disease. Canadian Journal of Surgery Journal Canadien de Chirurgie." vol. 53, No. 4, pp. 268-277 (2010).
Duffy et al., "Complexities in the estimation of overdiagnosis in breast cancer screening." British Journal of Cancer. vol. 99, No. 7, pp. 1176-1178 (2008).
Glass et al., "Breast cancer incidence, 1980-2006: combined roles of menopausal hormone therapy, screening mammography, and estrogen receptor status." Journal of the National Cancer Institute. vol. 99, No. 15, pp. 1152-1161 (2007).
Anampa et al., "Progress in adjuvant chemotherapy for breast cancer: an overview." BMC Medicine. vol. 13, No. 195, pp. 1-13 (2015).
Chew, "Adjuvant therapy for breast cancer: who should get what?" The Western Journal of Medicine. vol. 174, No. 4, pp. 284-287 (2001).
Cianfrocca et al., "Prognostic and predictive factors in early-stage breast cancer." The Oncologist. vol. 9, No. 6, pp. 606-616 (2004).
Consortium GT. "The Genotype-Tissue Expression (GTEx) project." Nature Genetics. vol. 4, No. 6, pp. 580-585 (2013).
Mele et al., "The human transcriptome across tissues and individuals." Science. vol. 348, No. 6235, pp. 660-665 (2015).
Alimonti et al., "Subtle variations in Pten dose determine cancer susceptibility." Nature Genetics. vol. 42, No. 5, pp. 454-458 (2010).
Richardson et al., "X chromosomal abnormalities in basal-like human breast cancer." Cancer Cell. vol. 9, No. 2, pp. 121-132 (2006).
Colak et al., "Age-specific gene expression signatures for breast tumors and cross-species conserved potential cancer progression markers in young women." PLoS ONE. vol. 8, No. 5, e63204 (2013).

(Continued)

*Primary Examiner* — Jerrry Lin
(74) *Attorney, Agent, or Firm* — Robin C. Chiang; Lawrence Berkeley National Laboratory

(57) ABSTRACT

A biomarker panel of 12 genes based on expression levels. Methods for calculating prognostic scores and patient ranking based on their score and divided into two equal sized cohorts. Kaplan-Meier analysis and a log-rank test were used to determine differences in survival.

1 Claim, 15 Drawing Sheets
Specification includes a Sequence Listing.

(56) References Cited

PUBLICATIONS

Kretschmer et al., "Identification of early molecular markers for breast cancer." Molecular Cancer. 10:15 (2011).

Chen et al., "Proliferative genes dominate malignancy-risk gene signature in histologically-normal breast tissue." Breast Cancer Research and Treatment. vol. 119, vol. 2, pp. 335-346 (2010).

Gyorffy et al., "An online survival analysis tool to rapidly assess the effect of 22,277 genes on breast cancer prognosis using microarray data of 1,809 patients." Breast Cancer Research and Treatment. vol. 23, No. 3, pp. 725-731 (2010).

Curtis et al., "The genomic and transcriptomic architecture of 2,000 breast tumours reveals novel subgroups." Nature. vol. 486, No. 7403, pp. 346-352 (2012).

Pereira et al., "The somatic mutation profiles of 2,433 breast cancers refines their genomic and transcriptomic landscapes." Nature Communications. vol. 7, No. 11479, pp. 1-16 (2016).

Parker et al., "Supervised risk predictor of breast cancer based on intrinsic subtypes." Journal of Clinical Oncology: Official Journal of the American Society of Clinical Oncology. vol. 27, No. 8, pp. 1160-1167 (2009).

Van't Veer et al., "Gene expression profiling predicts clinical outcome of breast cancer." Nature. vol. 415, No. 6871, pp. 530-536 (2002).

Wang et al., "Gene-expression profiles to predict distant metastasis of lymph-node-negative primary breast cancer." Lancet. vol. 365, No. 9460, pp. 671-679 (2005).

Paik et al., "A multigene assay to predict recurrence of tamoxifen-treated, node-negative breast cancer." The New England Journal of Medicine. vol. 351, No. 27, pp. 2817-2826 (2004).

Xiao et al., "Loss of PLZF expression in prostate cancer by immunohistochemistry correlates with tumor aggressiveness and metastasis." PLoS ONE. vol. 10, No. 3, e0121318 (2015).

Wang et al., "Hypermethylation reduces expression of tumor-suppressor PLZF and regulates proliferation and apoptosis in non-small-cell lung cancers." FASEB Journal: Official Publication of the Federation of American Societies for Experimental Biology. vol. 27, No. 10, pp. 4194-4203 (2013).

Brunner et al., "Increased expression of the tumor suppressor PLZF is a continuous predictor of long-term survival in malignant melanoma patients." Cancer Biotherapy & Radiopharmaceuticals. vol. 3, No. 4, pp. 451-459 (2008).

Du et al., "Maternal embryonic leucine zipper kinase enhances gastric cancer progression via the FAK/Paxillin pathway." Molecular Cancer. vol. 13, No. 100, pp. 1-14 (2014).

Kuner et al., "The maternal embryonic leucine zipper kinase (MELK) is upregulated in high-grade prostate cancer." Journal of Molecular Medicine. vol. 91, No. 2, pp. 237-248 (2013).

Pickard et al., "Dysregulated expression of Fau and MELK is associated with poor prognosis in breast cancer." Breast Cancer Research: BCR. vol. 11, No. 4, R60, pp. 1-8 (2009).

Nakano et al., "Maternal embryonic leucine zipper kinase is a key regulator of the proliferation of malignant brain tumors, including brain tumor stem cells." Journal of Neuroscience Research. vol. 86, No. 1, pp. 48-60 (2008).

Gray et al., "Maternal embryonic leucine zipper kinase/murine protein serine-threonine kinase 38 is a promising therapeutic target for multiple cancers." Cancer Research. vol. 65, No. 21, 9751-9761 (2005).

Wang et al., "MELK is an oncogenic kinase essential for mitotic progression in basal-like breast cancer cells." eLIFE. vol. 3, pp. 1-27, e01763 (2014).

Hu et al., "Downregulation of NUF2 inhibits tumor growth and induces apoptosis by regulating lncRNA AF339813." International Journal of Clinical and Experimental Pathology. vol. 8, No. 3, pp. 2638-2648 (2015).

Sugimasa et al., "Heterogeneous nuclear ribonucleoprotein K upregulates the kinetochore complex component NUF2 and promotes the tumorigenicity of colon cancer cells." Biochemical and Biophysical Research Communications. vol. 459, No. 1, pp. 29-35 (2015).

Dai et al., "Over-expression of EPS15 is a favorable prognostic factor in breast cancer." Molecular BioSystems. vol. 11, No. 11, pp. 2978-2985 (2015).

Amatschek et al., "Tissue-wide expression profiling using cDNA subtraction and microarrays to identify tumor-specific genes." Cancer Research. 64(3):844-856 (2004).

Yang et al., "The Impact of TIMM17A on Aggressiveness of Human Breast Cancer Cells." Anticancer Research. 36(3):1237-1241 (2016).

Xu et al., "Quantitative proteomics study of breast cancer cell lines isolated from a single patient: discovery of TIMMI7A as a marker for breast cancer." Proteomics. 10(7):1374-1390 (2010).

Goncharova et al., "TSC2 modulates actin cytoskeleton and focal adhesion through TSC1-binding domain and the Rac1 GTPase." The Journal of Cell Biology. 167(6):1171-1182 (2004).

Mehta et al., "Polymorphic variants in TSC1 and TSC2 and their association with breast cancer phenotypes." Breast Cancer Research and Treatment. 125(3):861-868 (2011).

Findley et al., "TSC1-2 tumour suppressor and regulation of mTOR signalling: linking cell growth and proliferation?" Current Opinion in Genetics & Development. 15(1):69-76 (2005).

Tang et al., "Lipid phosphate phosphatase-1 expression in cancer cells attenuates tumor growth and metastasis in mice." Journal of Lipid Research. 55(11):2389-2400 (2014).

Parkkila et al., "The calcium-binding protein S100P in normal and malignant human tissues." BMC Clinical Pathology. 8:2 (2008).

Salhab et al., "High TIMM17A expression is associated with adverse pathological and clinical outcomes in human breast cancer." Breast Cancer 19(2):153-160 (2012).

Prica et al., "The life and works of S100P—from conception to cancer." American Journal of Cancer Research. 6(2):562-576 (2016).

Perisic et al., "Plekhh2, a novel podocyte protein downregulated in human focal segmental glomerulosclerosis, is involved in matrix adhesion and actin dynamics." Kidney International. 82(10):1071-1083 (2012).

Parsons et al., "USP47 is a deubiquitylating enzyme that regulates base excision repair by controlling steady-stat; levels of DNA polymerase beta." Molecular Cell. 41(5):609-615 (2011).

Peschiaroli et al., "The ubiquitin-specific protease USP47 is a novel beta-TRCP interactor regulating cell survival." Oncogene. 29(9)1384-1393 (2010).

Jiang et al., "Anti-IgM-induced down-regulation of nuclear Thy28 protein expression in Ramos B lymphoma cells." Apoptosis : an International Journal on Programmed Cell Death. 8(5):509-519 (2003).

Lee et al., "Ahnak functions as a tumor suppressor via modulation of TGFbeta/Smad signaling pathway." Oncogene. 33(38):4675-4684 (2014).

Goodwin et al., "An AMPK-independent signaling pathway downstream of the LKB1 tumor suppressor controls Snail1 and metastatic potential" Molecular Cell. 55(3):436-450 (2014).

| Human Breast Tumor Data | Invasive ductal carcinoma samples | Normal breast samples | PMID |
|---|---|---|---|
| GSE3744 | 40 | 7 | 16473279; 20400965 |
| GSE10780 | 42 | 143 | 19266279 |
| GSE21422 | 5 | 5 | 21314937 |
| GSE29044 | 73 | 36 | 23704896 |
| Total | 160 | 191 | |

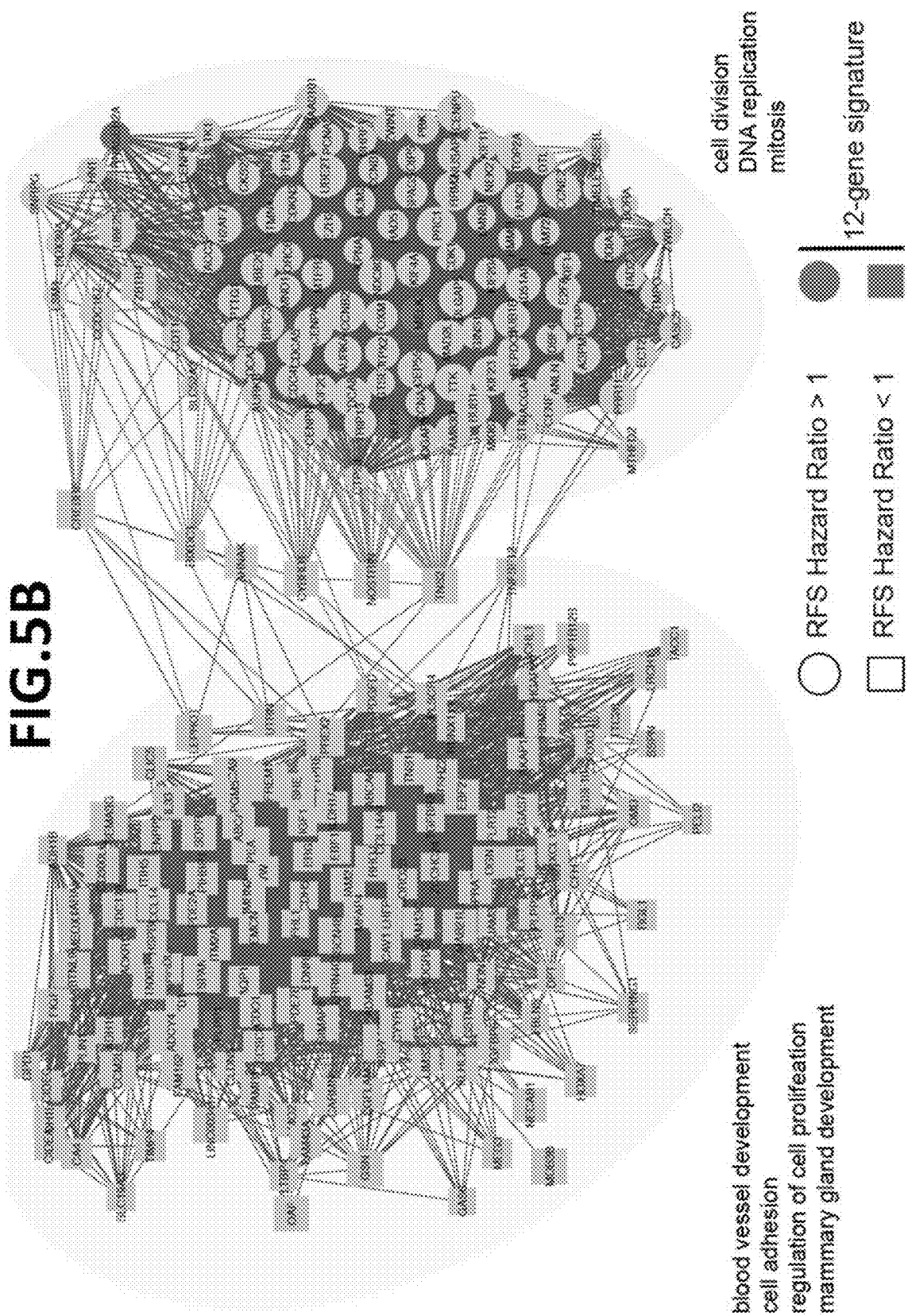

| Factors | Hazard Ratio | 95% CI | Significance |
|---|---|---|---|
| Tumor stage II vs I | 1.616 | 0.93-2.82 | .091 |
| Tumor stage III vs I | 3.341 | 1.87-5.98 | .000 |
| Tumor stage IV vs I | 10.939 | 5.31-22.55 | .000 |
| Estrogen receptor status | 1.633 | 0.94-2.85 | .084 |
| Progesterone receptor status | 1.294 | 0.77-2.16 | .325 |
| Prognostic score | 2.123 | 1.23-3.66 | .007 |
| Age at diagnosis | 1.030 | 1.02-1.04 | .000 |

| Factors | Hazard Ratio | 95% CI | Significance |
|---|---|---|---|
| Age at diagnosis | 1.037 | 1.03-1.04 | 0.000 |
| Estrogen receptor status | .689 | 0.55-0.87 | 0.001 |
| Progesterone receptor status | .914 | 0.79-1.1 | 0.233 |
| Grade | | | 0.010 |
| PAM50 | | | 0.002 |
| Prognostic score | 1.355 | 1.18-1.56 | 0.000 |

FIG. 7C

12-GENE PROGNOSTIC SIGNATURE FOR BREAST CANCER SURVIVAL

RELATED PATENT APPLICATIONS

The application claims priority to U.S. Provisional Patent Application Ser. No. 62/445,256, filed Jan. 12, 2017; which is incorporated herein by reference.

STATEMENT OF GOVERNMENTAL SUPPORT

This invention was made with government support under Contract No. DE-AC02-05CH11231 awarded by the U.S. Department of Energy. The government has certain rights in the invention.

REFERENCE TO SEQUENCE LISTING AND/OR TABLES

This application also incorporates by reference Tables S1A-S1D, S2A-S2E, S3A-S3B, and S4 of U.S. Provisional Patent Application Ser. No. 62/445,256, filed Jan. 12, 2017.

BACKGROUND OF THE INVENTION

Field of the Invention

The present invention relates to genomic prognostic markers and signatures for screening, diagnostics and prognostics of cancer, especially breast cancer.

Related Art

Breast cancer (BC) is the leading female malignancy and the second leading cause of cancer deaths in U.S. women, with tumor metastasis being the underlying cause in most of these breast cancer related deaths [1, 2]. Breast carcinogenesis is a multi-step process in which epithelial cells accumulate genetic alterations, which in a permissive tissue microenvironment progress towards malignancy and may then metastasize to distant organs. Advances in imaging technologies and heightened public awareness of breast cancer have resulted in an increase in the diagnosis of early-stage breast cancer [3-5]. Furthermore, adjuvant systemic therapy has reduced the risk of recurrence and improved overall survival from BC [6]. However, not all patients who receive adjuvant therapy benefit from it and could have been spared the treatment-associated toxicity. Prognostic factors are critical to distinguish patients with poor prognoses, who would benefit from adjuvant therapy, from patients with good prognoses, who may not benefit sufficiently from adjuvant therapy to outweigh the risks associated with treatment [7].

Traditional prognostic factors currently used to guide the use of systemic therapy and predict outcome include tumor size, lymph node involvement, histological grade, age, race, estrogen receptor (ER), progesterone receptor (PR) and epidermal growth factor receptor (HER2) status [8]. However, a critical problem with BC is the difference in clinical outcome among patients with the same disease. This heterogeneous clinical outcome is manifested by differences in disease susceptibility, progression, treatment response, and relapse, even among individuals with the same apparent histopathological disease. These differences seem to be in part controlled by so-called tumor modifier genes, multiple low-penetrance susceptibility genes that interact with each other and their environment to contribute to the disease process.

Clinical patient survival data, along with genomic datasets can be used to identify genes important in patient survival. Recently, a large gene expression database across normal human tissues became available and which can be used to identify the biological mechanisms underlying different diseases and identify potential novel therapeutic targets [9, 10]. We combined independent BC databases to identify a gene expression signature of differentially expressed genes. Using gene co-expression network analyses, we investigated the genetic architecture of this signature in normal breast tissue. We subsequently identified and validated a 12-gene signature that predicts BC survival.

BRIEF SUMMARY OF THE INVENTION

Large genomic datasets in combination with clinical data can be used as an unbiased tool to identify genes important in patient survival and discover potential therapeutic targets. We used a genome-wide screen to identify 587 genes significantly and robustly deregulated across four independent breast cancer (BC) datasets compared to normal breast tissue. Gene expression of 381 genes was significantly associated with relapse-free survival (RFS) in BC patients. We used a gene co-expression network approach to visualize the genetic architecture in normal breast and BCs. In normal breast tissue, co-expression cliques were identified enriched for cell cycle, gene transcription, cell adhesion, cytoskeletal organization and metabolism. In contrast, in BC, only two major co-expression cliques were identified enriched for cell cycle-related processes or blood vessel development, cell adhesion and mammary gland development processes.

Interestingly, gene expression levels of 7 genes were found to be negatively correlated with many cell cycle related genes, highlighting these genes as potential tumor suppressors and novel therapeutic targets. A forward-conditional Cox regression analysis was used to identify a 12-gene signature associated with RFS. A prognostic scoring system was created based on the 12-gene signature. This scoring system robustly predicted BC patient RFS in 60 sampling test sets and was further validated in TCGA and METABRIC BC data. Our integrated study identified a 12-gene prognostic signature that could guide adjuvant therapy for BC patients and includes novel potential molecular targets for therapy.

Thus, the present invention provides for a 12-gene prognostic signature for breast cancer and methods for prognosis using the 12-gene prognostic signature.

In one embodiment, methods for calculating a cancer patient's prognostic score and determining whether the patient has a prognosis for relapse-free survival.

BRIEF DESCRIPTION OF THE TABLES

Table 1. 12-Gene signature
Table 2. 12-Gene signature with Accession IDs.
Tables S1A-S1D. Differential gene expression between breast tumor and normal breast tissue in the following datasets: Table S1A—GSE01780; Table S1B—GSE03744; Table S1C—GSE21422; and Table S1D—GSE29044.
Table S2A-S2E. The 795 probe IDs robustly deregulated in breast cancer. Table S2A are the 795 probe IDs. Table S2B shows the fold changes in GSE3744. Table S2C shows the fold changes in GSE01780. Table S2D shows the fold changes in GSE21422. Table S2E shows the fold changes in GSE29044.

Table S3A and S3B. Genes significantly associated with relapse-free survival in breast cancer patients. Table S3A shows the genes with Hazard Ratio less than 1 (HR<1); Table S3B shows the genes with Hazard Ratio greater than 1 (HR>1).

Table S4. Significant GO categories associated with 381 genes significantly associated with relapse-free survival in breast cancer.

BRIEF DESCRIPTION OF THE DRAWINGS AND TABLES

Figure 2:
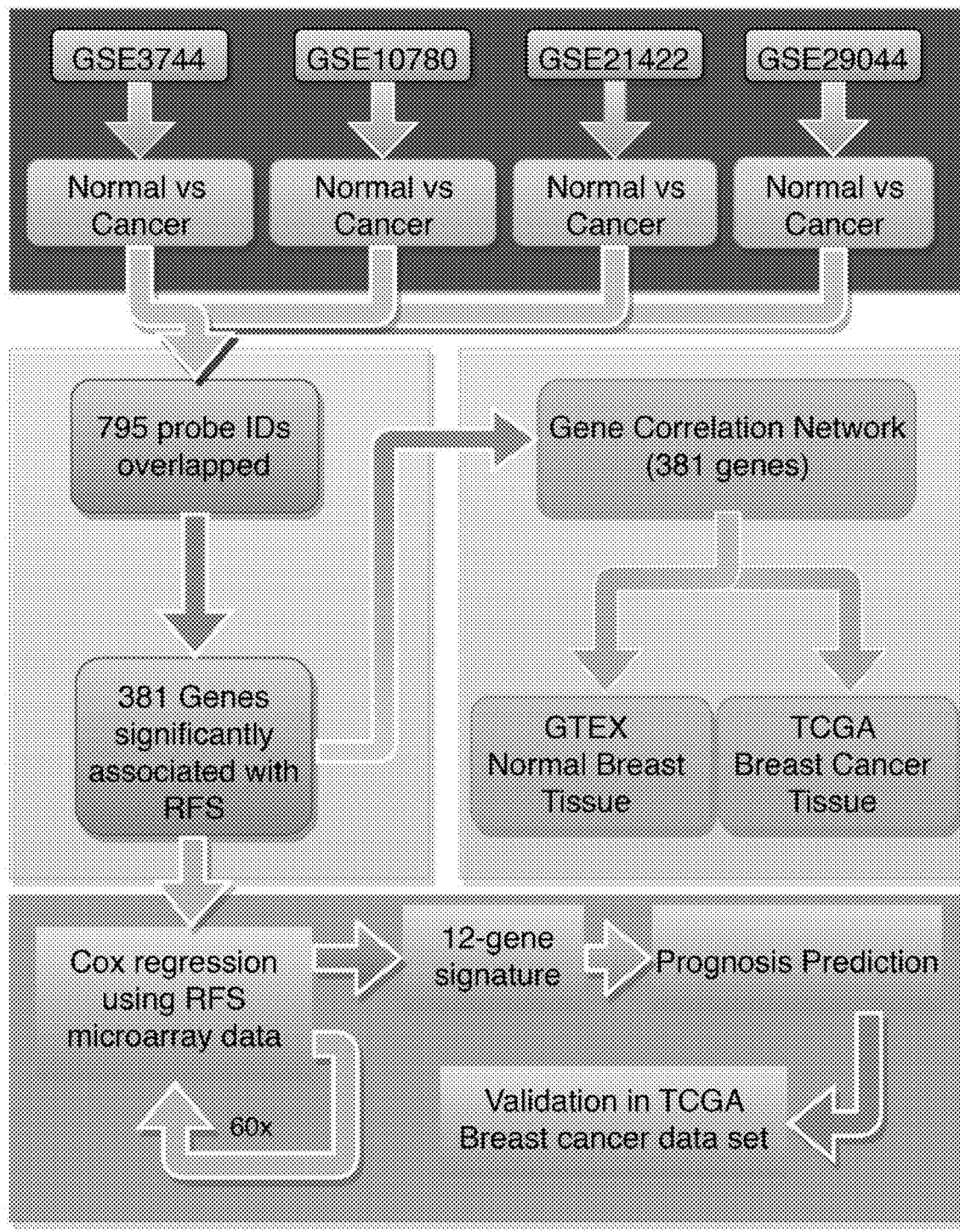

FIG. 2 is a flow diagram for identifying and validating a prognostic biomarker panel for breast cancer. The 795 robustly deregulated probe IDs were identified using 4 breast tumor microarray data sets (blue). To identify individual genes associated with relapse-free survival (RFS), Kaplan Meier survival analysis was run on the overlapping IDs (yellow). A gene expression correlation network approach was used to identify cliques of functionally related genes (green). Cox regression was run on 60 random tumor samples for 381 genes significantly associated with RFS (turquoise) to generate the 12-gene signature. The 12-gene signature was used to generate a prognosis scoring system, which was validated using the TCGA and METABRIC BC data sets.

Figure 3:
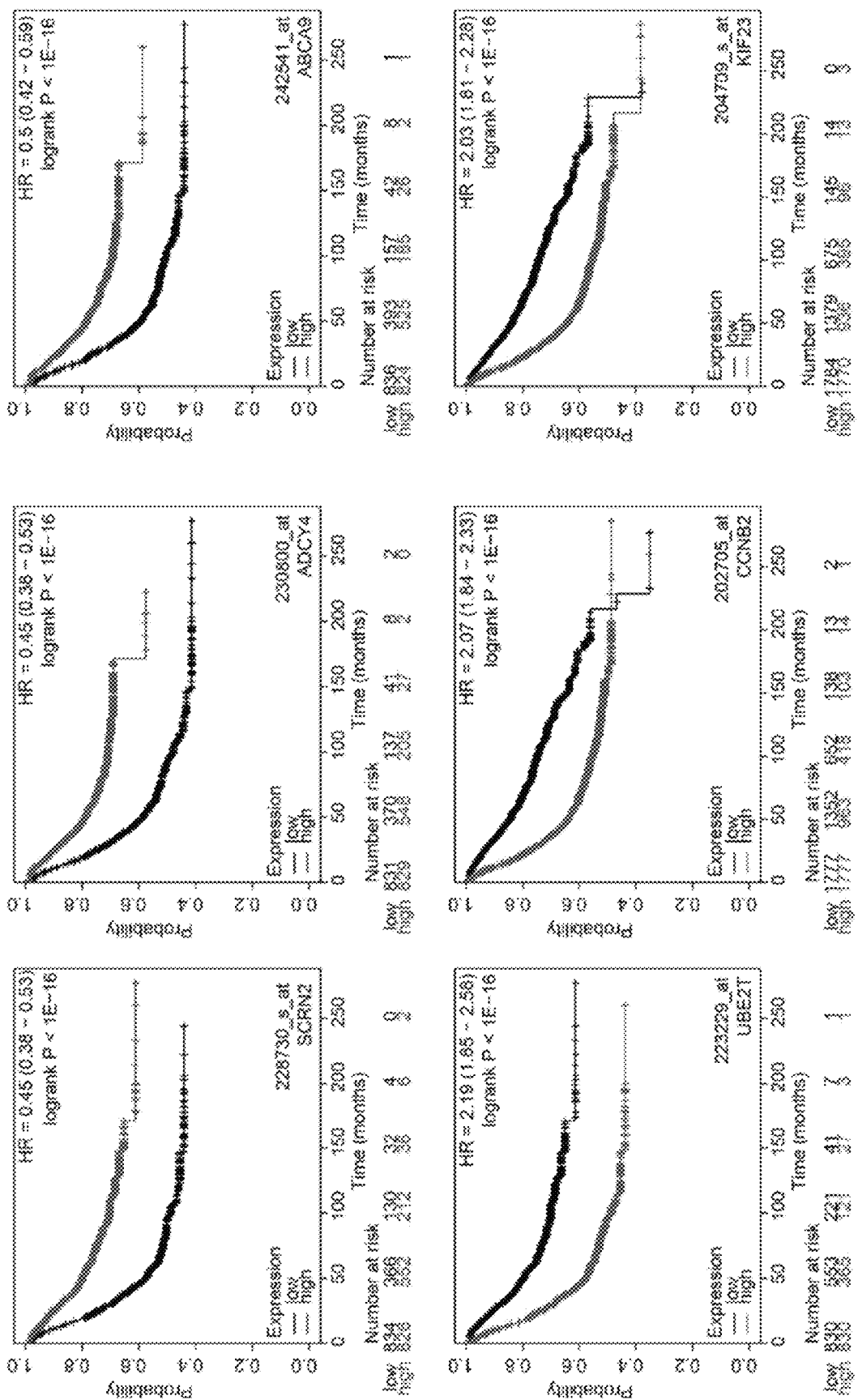

FIG. 3 shows Kaplan-Meier survival curves for breast cancer patients according to tumor expression of genes with highest and lowest hazard ratios. The breast cancer patient cohort was divided into two equal groups based on median expression for each gene and compared by a Kaplan-Meier survival analysis. The estimate of the hazard ratio (HR) and log-rank p-value of the curve comparison between the groups is shown. Top three genes with the lowest HR values (top row): SCRN2, ADCY4 and ABCA9. Top three genes with the highest HR values (bottom row): UBE2T, CCNB2 and KIF23. Low and high risks indicated in black and red, respectively.

Figure 4A:
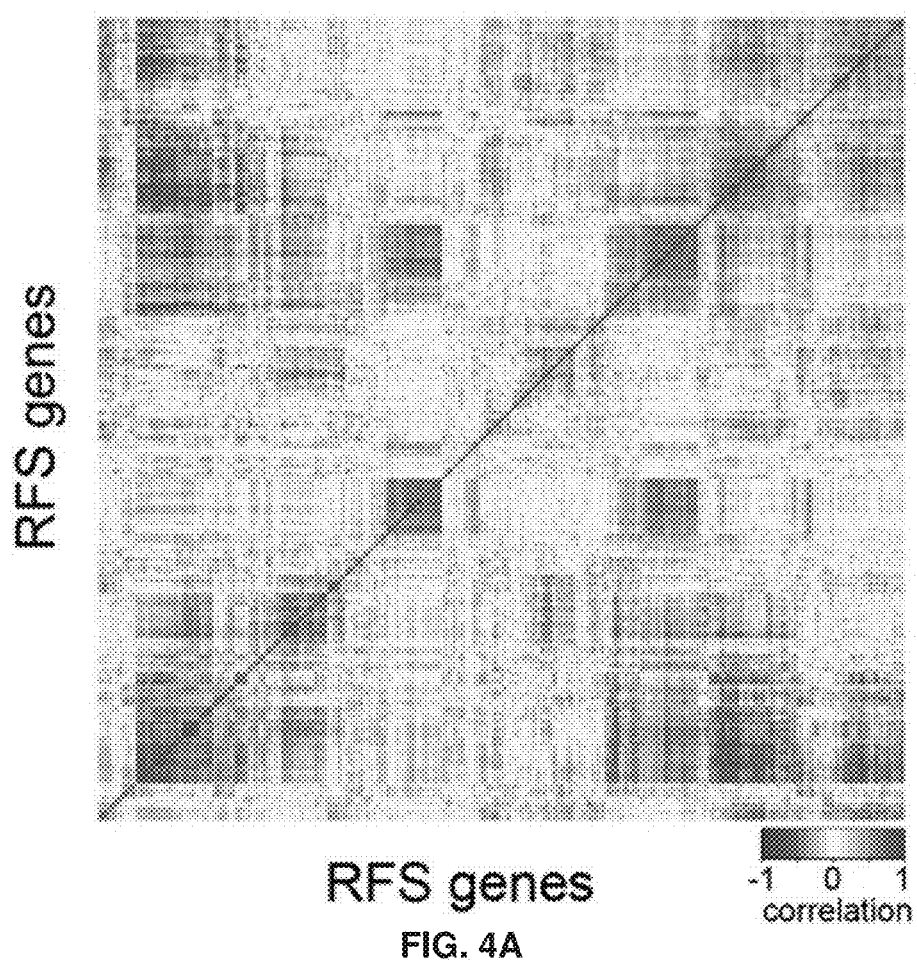

FIG. 4A shows a visual representation of correlations in gene expression in normal human breast tissue samples. The heat map shows the correlation in gene expression between normal breast tissue samples obtained from GTEX. Positive correlations are indicated in red, while negative correlations are indicated in blue.

Figure 4B:
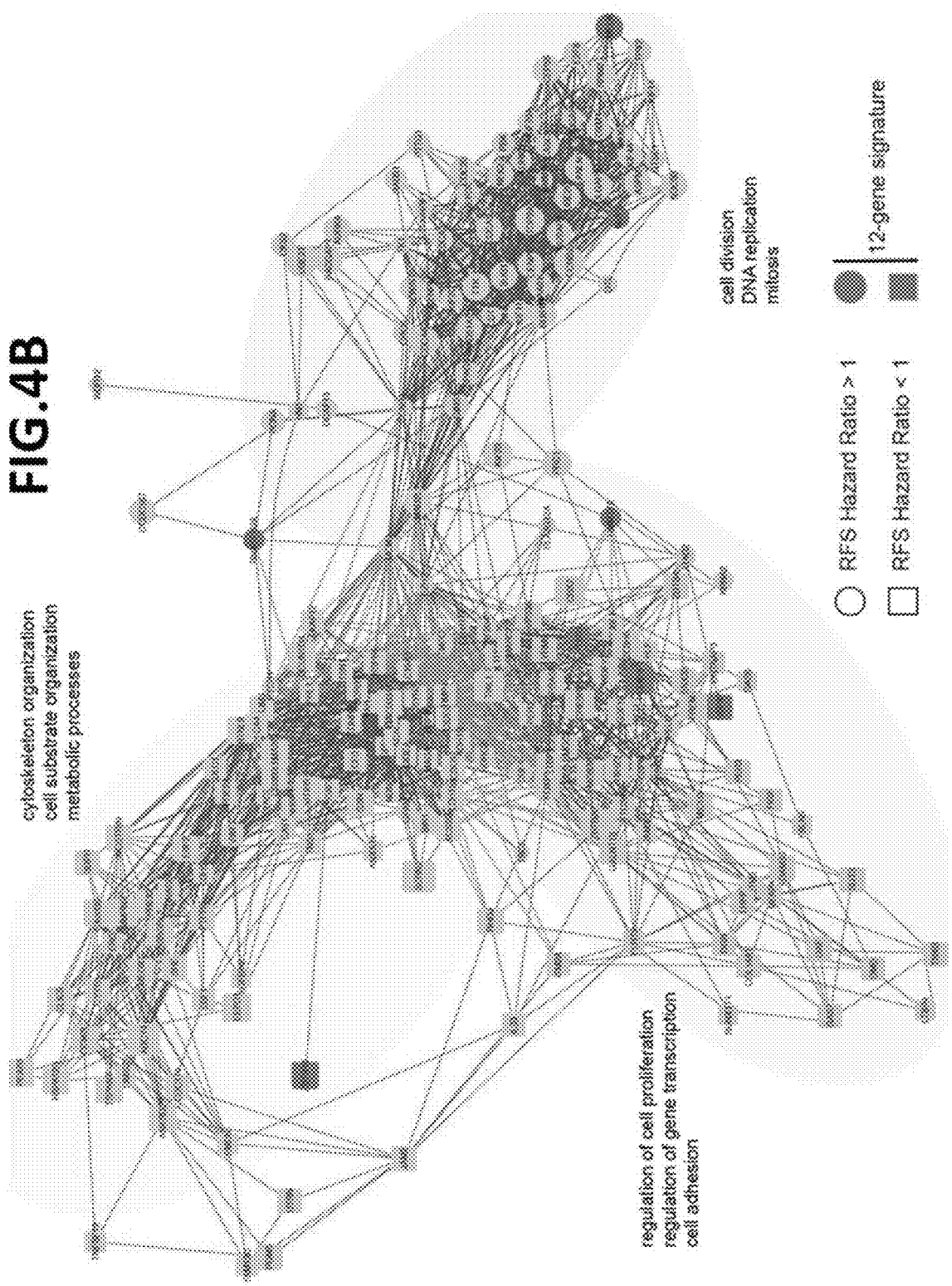

FIG. 4B shows a visual representation of correlations in gene expression in normal human breast tissue samples. Gene expression correlation network of RFS significant genes in normal breast tissue samples. Individual genes are indicated as nodes. Red edges indicate a positive correlation in gene expression ($r \geq 0.6$) between two genes. Green edges indicate a negative correlation in gene expression between two genes ($r \leq -0.6$). Labels indicate significant biological enrichment (adjusted p-value<0.05). Pink colored genes are present in the 12-gene prognostic signature. Three major functional cliques were separated based on gene-ontology. Clique 1 (yellow): cytoskeleton organization, cell substrate organization, and metabolic processes. Clique 2 (orange): regulation of cell proliferation, regulation of gene transcription, and cell adhesion. Clique 3 (blue): ell division, DNA replication, and mitosis. Genes with hazard ratio for RFS>1 are indicated as circles and those with HR<1 as squares.

Figure 4C:
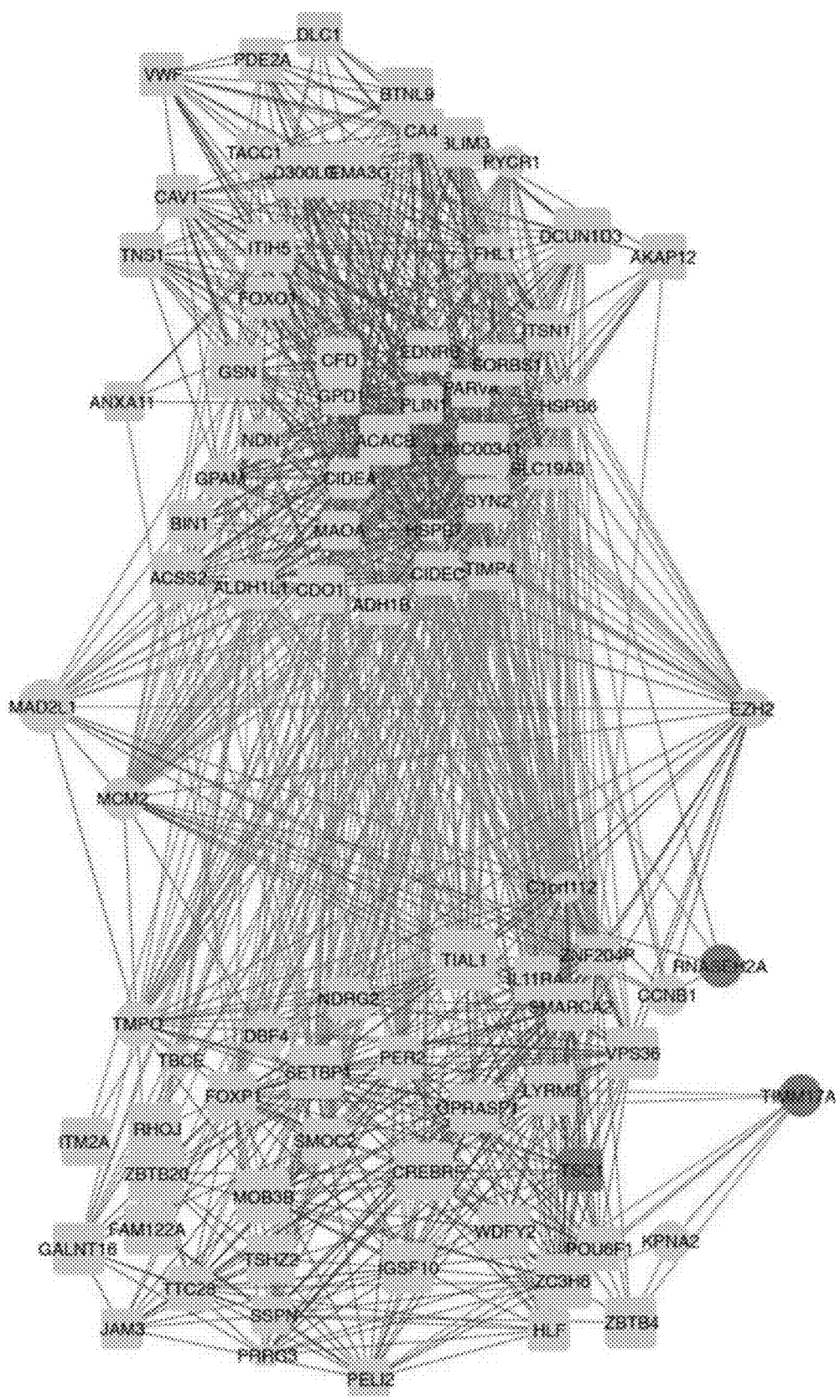

FIG. 4C shows a visual representation of correlations in gene expression in normal human breast tissue samples. Enlargement of negative correlations and the genes associated with them.

Figure 4D:
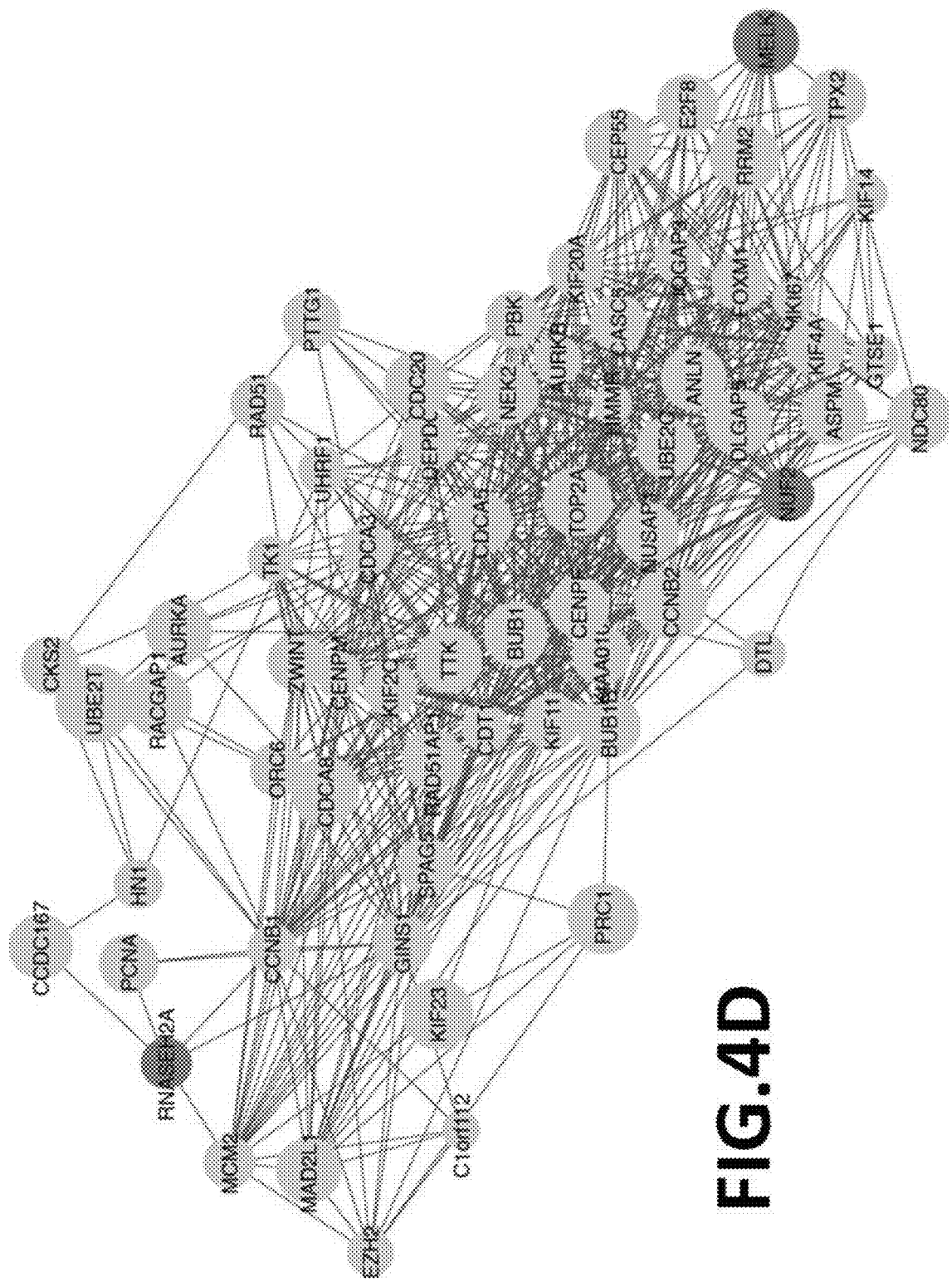

FIG. 4D shows a visual representation of correlations in gene expression in normal human breast tissue samples. Enlarged cell division, DNA replication, and mitosis clique.

Figure 5A:
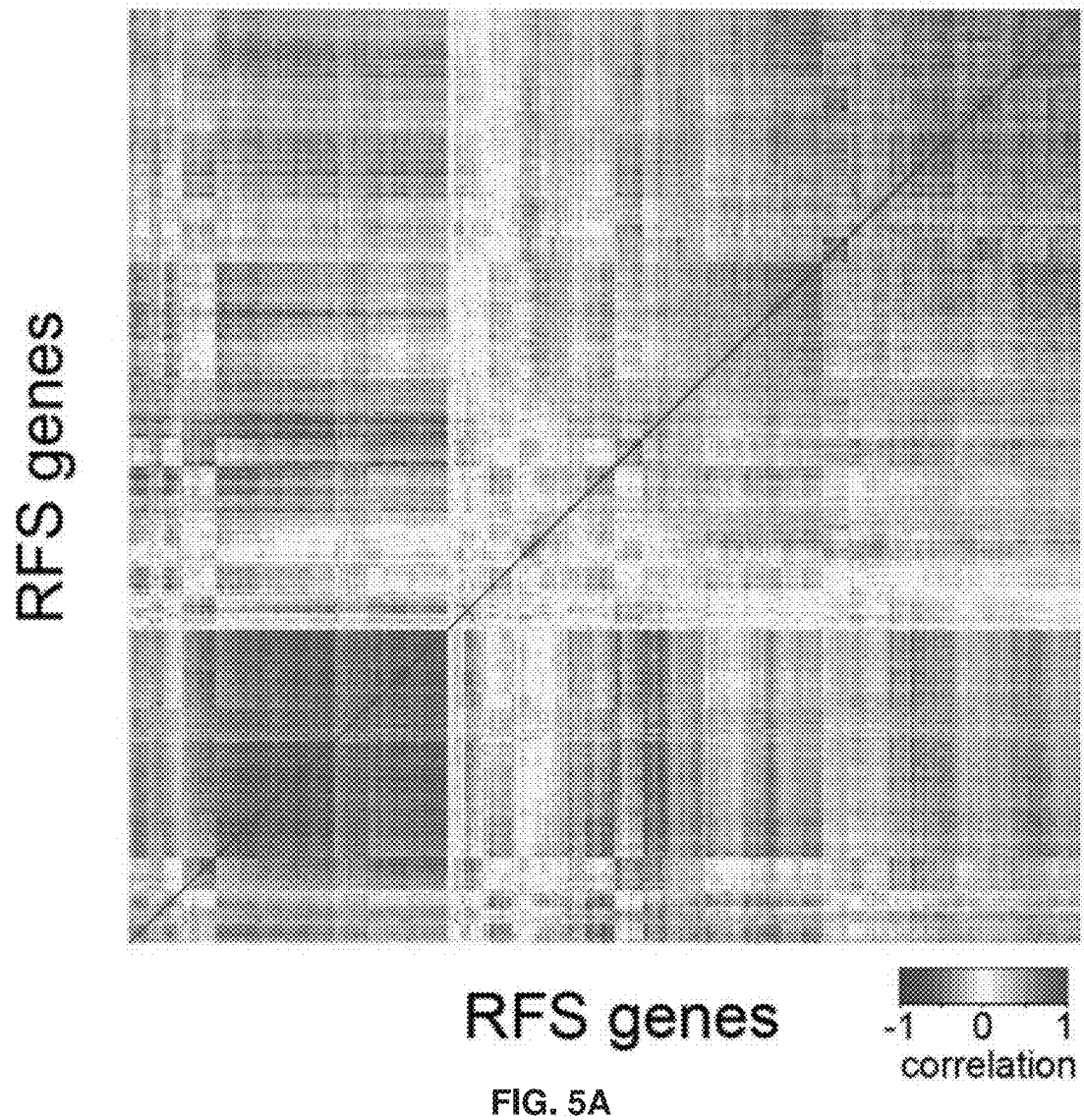

FIG. 5A shows visual representation of correlations in gene expression in breast cancer samples. The heat map shows the correlation in gene expression between breast cancer samples obtained from TCGA. Positive correlations are indicated in red, while negative correlations are indicated in blue.

FIG. 5B shows visual representation of correlations in gene expression in breast cancer samples. Gene expression correlation network of RFS significant genes in breast cancer samples. Individual genes are indicated as nodes. Red edges indicate a positive correlation in gene expression ($r \geq 0.6$) between two genes. Green edges indicate a negative correlation in gene expression between two genes ($r \leq -0.6$). Labels indicate significant biological enrichment (adjusted p-value<0.05). Pink colored genes are present in the 12-gene prognostic signature. Two major functional cliques were separated based on gene-ontology. Clique 1 (orange): blood vessel development, cell adhesion, regulation of cell proliferation and mammary gland development. Clique 2 (blue): cell division, DNA replication, and mitosis. Genes with hazard ratio for RFS>1 are indicated as circles and those with HR<1 as squares.

Figure 5C:
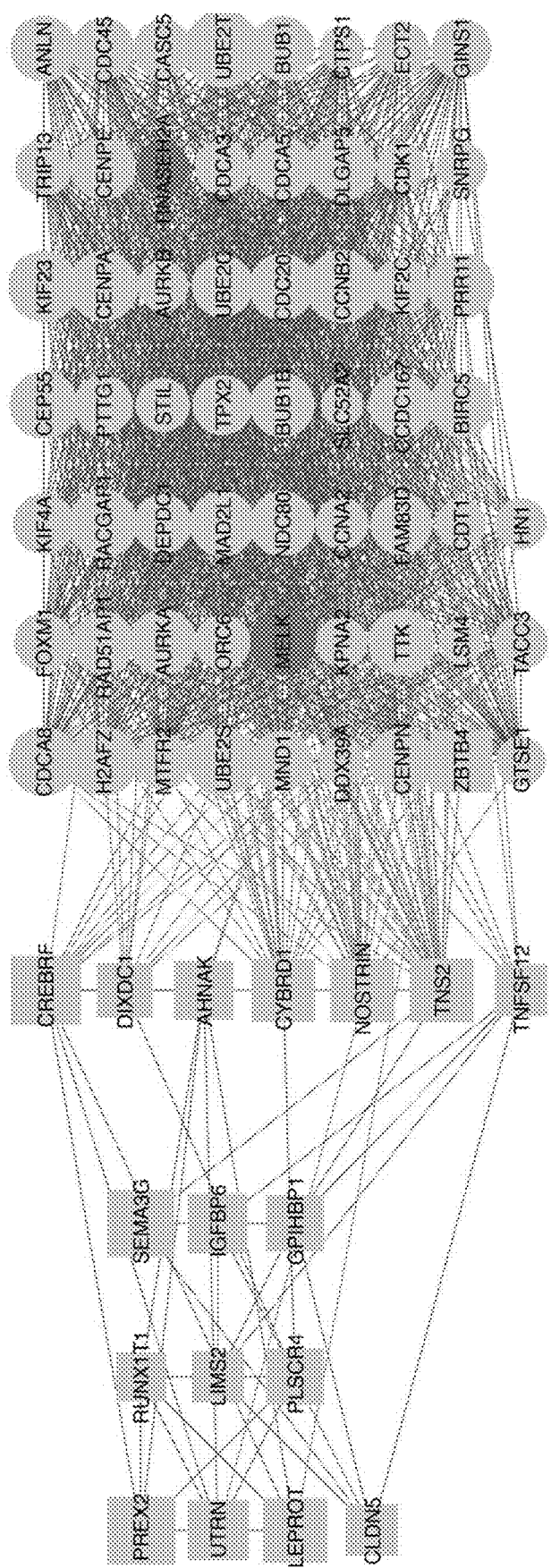

FIG. 5C shows visual representation of correlations in gene expression in breast cancer samples. Correlation network with negatively correlated genes and its association with cell division, DNA replication, and mitosis genes, as well as some blood vessel development, cell adhesion, regulation of cell proliferation, and mammary gland development genes.

Figure 6A:
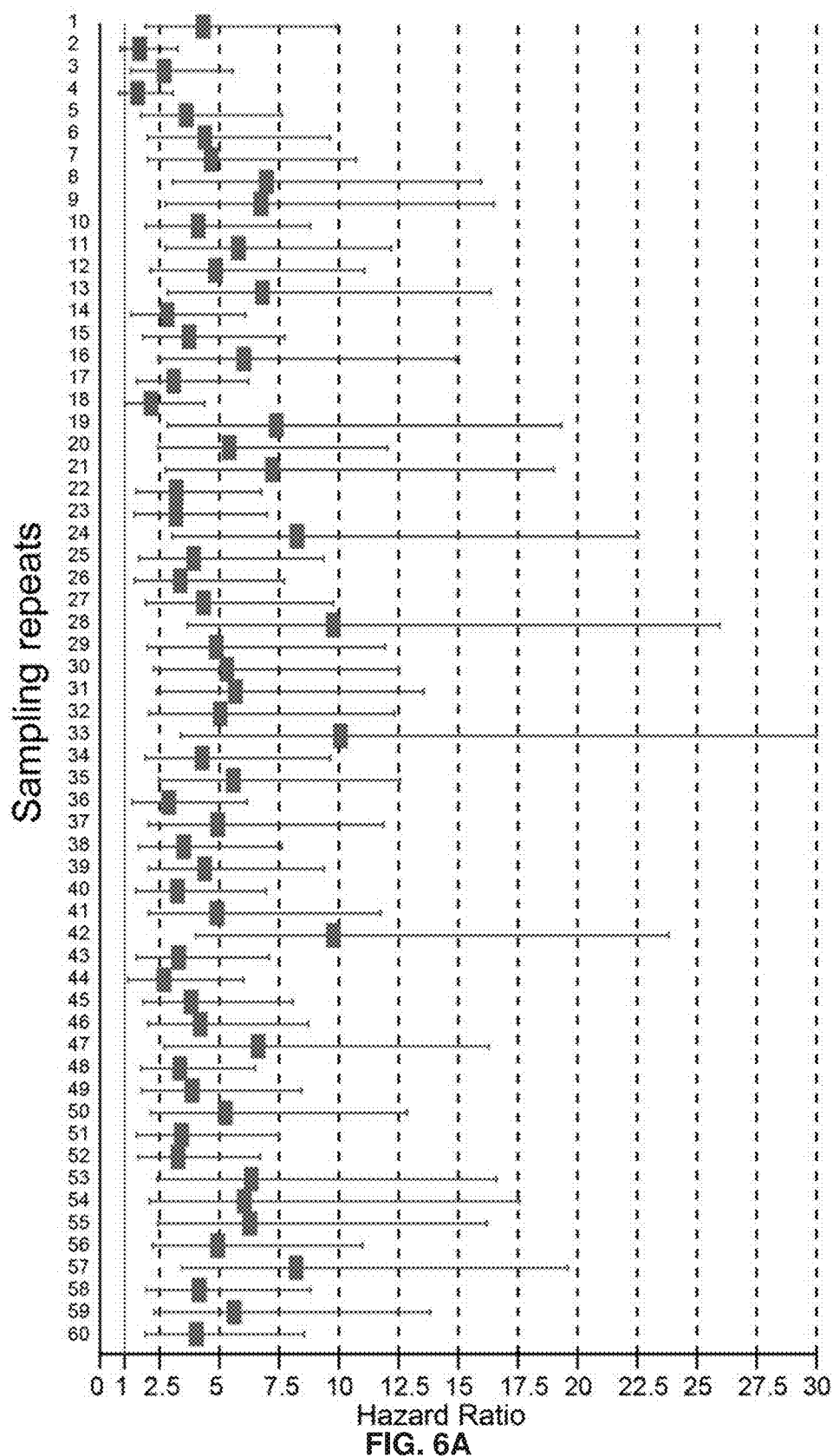

FIG. 6A describes a 12-gene signature predicts breast cancer patient prognosis. For each of 60 test sets the hazard ratio and the 95% confidence interval was calculated using a Cox model based on the prognostic score with groups as covariates, and subsequently plotted in a forest-plot diagram. The red line indicates a HR value of 1, or the null hypothesis. The two red boxes indicate the insignificant trials (confidence interval included HR value of 1).

Figures 6B, 6C:
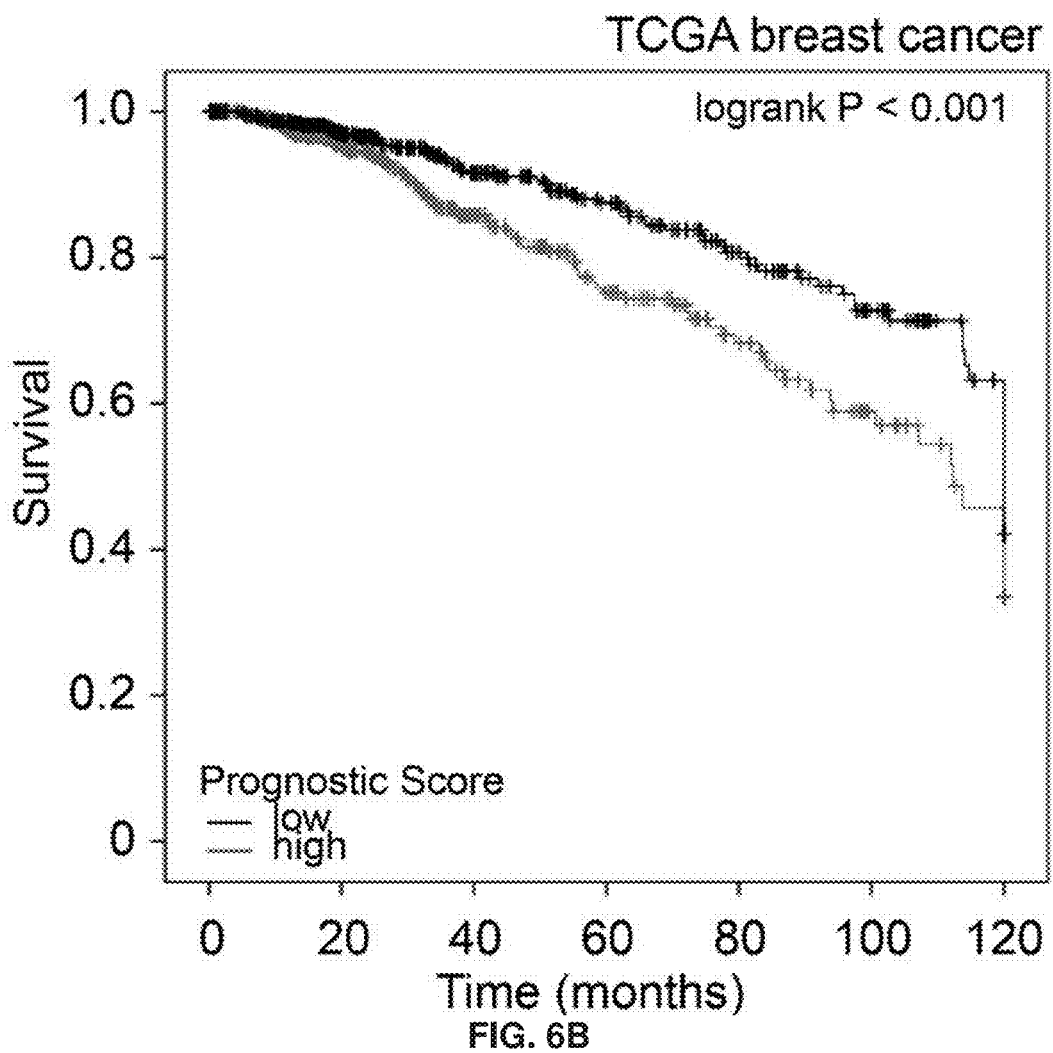

FIG. 6B describes a 12-gene signature predicts breast cancer patient prognosis. Kaplan-Meier overall survival curve for breast cancer patients according to prognostic score using the 12-gene signature. The BC patient cohort was divided into two equal groups based on the prognostic score. The log-rank p-value of the curve comparison between the groups is shown.

FIG. 6C describes a 12-gene signature predicts breast cancer patient prognosis. The hazard ratio and the 95% confidence interval was calculated using a Cox model based on tumor stage (I-IV), estrogen receptor and progesterone receptor status, age at diagnosis and prognostic score as covariates.

Figure 7A:
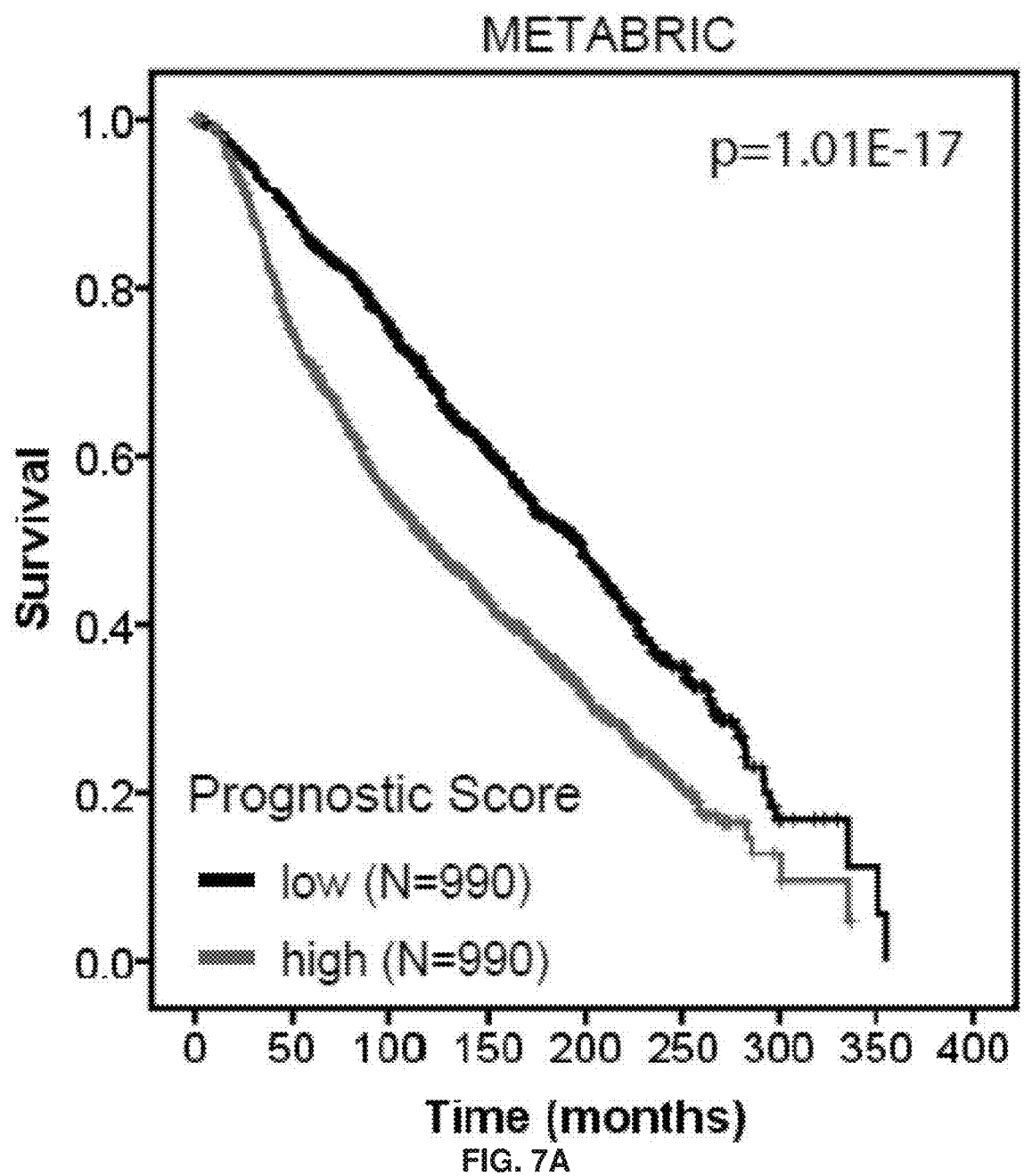

FIG. 7A shows the 12-gene signature predicts overall survival independent of clinical factors and molecular subtypes. Kaplan-Meier overall survival curve for breast cancer patients according to prognostic score using the 12-gene signature. The BC patient cohort was divided into two equal groups based on the prognostic score. The log-rank p-value of the curve comparison between the groups is shown.

Figure 7B:
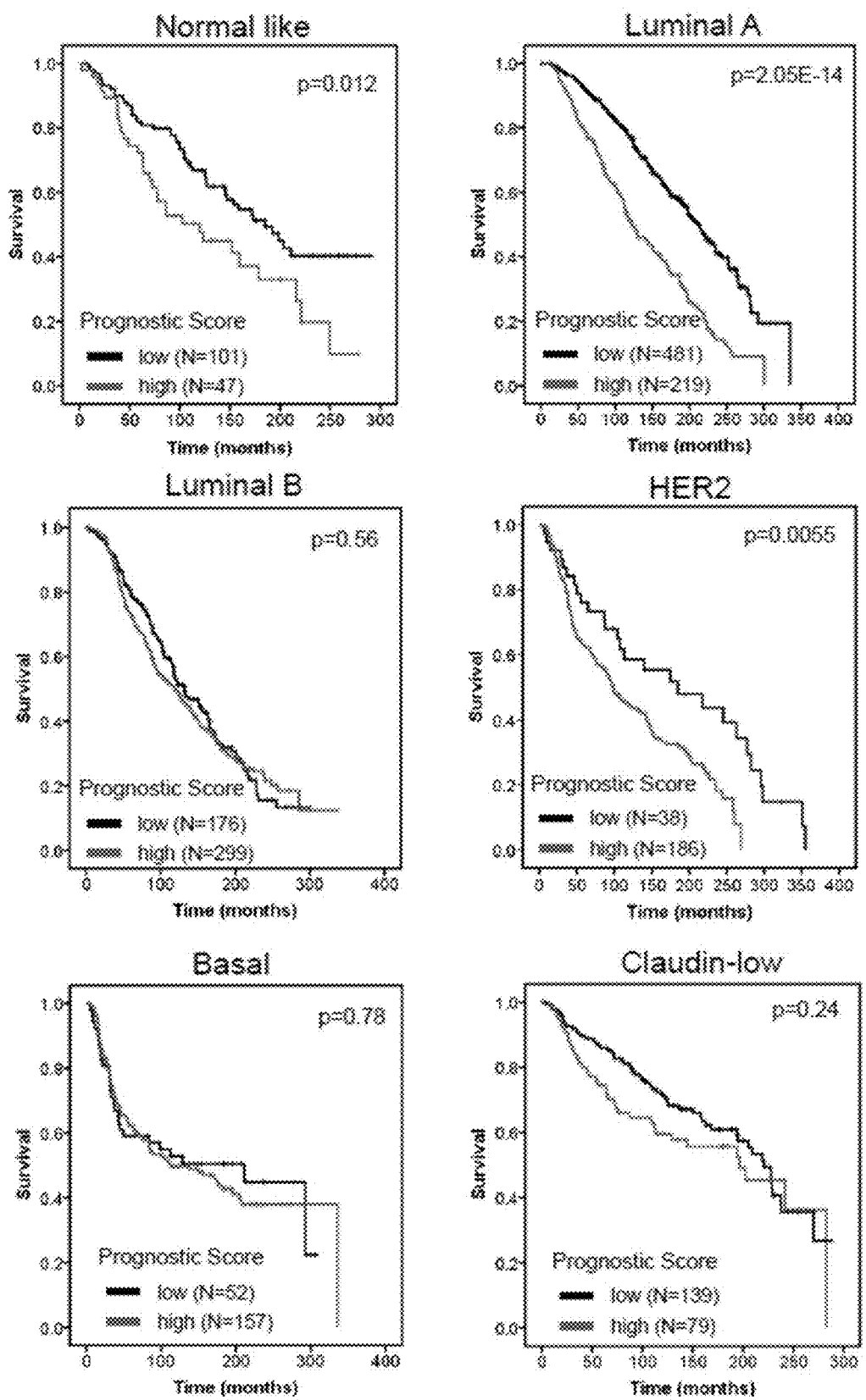

FIG. 7B shows the 12-gene signature predicts overall survival independent of clinical factors and molecular subtypes. Kaplan-Meier overall survival curve for breast cancer patients stratified by molecular subtype. The log-rank p-value of the curve comparison between the groups is shown.

FIG. 7C shows the 12-gene signature predicts overall survival independent of clinical factors and molecular subtypes. The hazard ratio and the 95% confidence interval was calculated using a Cox model based on tumor grade, estrogen receptor and progesterone receptor status, age at diagnosis, molecular subtype (PAM50) and prognostic score as covariates.

DETAILED DESCRIPTION OF THE EMBODIMENTS

In one embodiment, a forward-conditional Cox regression analysis was used to identify a 12-gene signature associated with relapse-free survival (RFS). A prognostic scoring system was created based on the 12-gene signature. This scoring system robustly predicted BC patient RFS in 60 sampling test sets and was further validated in TCGA and METABRIC BC data. Our integrated study identified a 12-gene prognostic signature that could guide adjuvant therapy for BC patients and includes novel potential molecular targets for therapy.

Thus, in some embodiments a 12-gene prognostic signature for breast cancer and methods for prognosis using the 12-gene prognostic signature.

In the examples, the average beta-value (Cox regression coefficient) of each of the 12 genes was calculated and used as a weighting factor for the expression value of each gene. A prognostic score was estimated for each patient: gene expression values were multiplied by their respective beta-value and the prognostic score was determined as the sum of resulting weighted gene expression values. The patients were ranked by their prognostic score, divided into two equal sized cohorts based on the median score, and Kaplan-Meier analysis was performed to determine differences in RFS between two cohorts. Using the mean beta values developed in the training set, prognostic scores were calculated for all patients in the 60 test sets. Patients were again ranked on their prognostic score and divided into two cohorts based on the average prognostic-score cut-point in the 60 training sets. Kaplan-Meier analysis was performed and a log-rank test was used to determine if there was a significant difference in RFS between two cohorts. The hazard ratio was calculated for each of the 60 test sets.

TABLE 1

Twelve-gene prognostic gene signature

| Gene symbol | Gene name | Affymetrix ID | Hazard Ratio | p-value |
|---|---|---|---|---|
| EPS15 | Epidermal growth factor receptor substrate 15 | 217886_at | 0.73 | 9.30E−08 |
| MELK | Maternal Embryonic Leucine Zipper Kinase | 204825_at | 1.89 | 1.00E−16 |
| NUF2 | NDC80 Kinetochore Complex Component | 223381_at | 1.63 | 2.30E−09 |
| RNASEH2A | Ribonuclease H2 Subunit A | 203022_at | 1.56 | 1.90E−14 |
| S100P | S100 Calcium Binding Protein P | 204351_at | 1.45 | 2.50E−10 |
| THYN1 | Thymocyte Nuclear Protein 1 | 218491_s_at | 0.76 | 2.70E−06 |
| TIMM17A | Translocase Of Inner Mitochondrial Membrane 17 Homolog A | 201821_s_at | 1.55 | 3.70E−14 |
| TSC1 | Tuberous Sclerosis 1 | 209390_at | 0.74 | 4.00E−07 |
| USP47 | Ubiquitin Specific Peptidase 47 | 223119_s_at | 0.65 | 2.40E−07 |
| ZBTB16 | Zinc finger and BTB domain containing 16 | 205883_at | 0.6 | 1.00E−16 |
| PLPP1 | Phospholipid Phosphatase 1 | 209147_s_at | 0.77 | 4.10E−06 |
| PLEKHH2 | Pleckstrin Homology, MyTH4 And FERM Domain Containing H2 | 227148_at | 0.59 | 1.70E−10 |

TABLE 2

12-Gene signature

| Gene symbol | Gene name | Affymetrix ID | Hazard Ratio | p-value | Ensembl | Entrez Gene | RefSeq Transcript ID |
|---|---|---|---|---|---|---|---|
| EPS15 | Epidermal growth factor receptor substrate 15 | 217886_at | 0.73 | 9.30E−08 | ENSG00000085832 | 2060 | NM_001981 |
| MELK | Maternal Embryonic Leucine Zipper Kinase | 204825_at | 1.89 | 1.00E−16 | ENSG00000165304 | 9833 | NM_014791 |
| NUF2 | NDC80 Kinetochore Complex Component | 223381_at | 1.63 | 2.30E−09 | ENSG00000143228 | 83540 | NM_031423 /// NM_145697 |
| RNASEH2A | Ribonuclease H2 Subunit A | 203022_at | 1.56 | 1.90E−14 | ENSG00000104889 | 10535 | NM_006397 |
| S100P | S100 Calcium Binding Protein P | 204351_at | 1.45 | 2.50E−10 | ENSG00000163993 | 6286 | NM_005980 |
| THYN1 | Thymocyte Nuclear Protein 1 | 218491_s_at | 0.76 | 2.70E−06 | ENSG00000151500 | 29087 | NM_001037304 /// NM_001037305 /// NM_014174 /// NM_199297 /// NM_199298 |

TABLE 2-continued

12-Gene signature

| Gene symbol | Gene name | Affymetrix ID | Hazard Ratio | p-value | Ensembl | Entrez Gene | RefSeq Transcript ID |
|---|---|---|---|---|---|---|---|
| TIMM17A | Translocase Of Inner Mitochondrial Membrane 17 Homolog A | 201821_s_at | 1.55 | 3.70E−14 | ENSG00000134375 | 10440 | NM_006335 |
| TSC1 | Tuberous Sclerosis 1 | 209390_at | 0.74 | 4.00E−07 | ENSG00000165699 | 7248 | NM_000368 /// NM_001008567 |
| USP47 | Ubiquitin Specific Peptidase 47 | 223119_s_at | 0.65 | 2.40E−07 | ENSG00000170242 | 55031 | NM_017944 |
| ZBTB16 | Zinc finger and BTB domain containing 16 | 205883_at | 0.6 | 1.00E−16 | ENSG00000109906 | 7704 | NM_001018011 /// NM_006006 |
| PLPP1 | Phospholipid Phosphatase 1 | 209147_s_at | 0.77 | 4.10E−06 | ENSG00000067113 | 8611 | NM_003711 /// NM_176895 |
| PLEKHH2 | Pleckstrin Homology, MyTH4 And FERM Domain Containing H2 | 227148_at | 0.59 | 1.70E−10 | ENSG00000152527 | 130271 | NM_172069 |

In some embodiments, methods for calculating a cancer patient's prognostic score and determining whether the patient has a prognosis for relapse-free survival. In one embodiment, a method for calculating a cancer patient's prognostic score comprising steps of: measuring the gene expression level of the 12 genes, EPS15, MELK, NUF2, RNASEH2A, S100P, THYN1, TIMM17A, TSC1, USP47, ZBTB16, PLPP1, PLEKHH2, in a patient's tumor tissue; calculating the prognostic score using the formula $$\sum_{i=1}^{12} (\text{gene } i\,\beta) \times (\text{gene } i \text{ expression level})$$

where the beta values for each of the 12 genes is obtained from Cox Hazard Regression model; assigning the patient to the appropriate prognostic group based on the calculated prognostic score, whereby the cut points for high and low scores depend on the platform used to assess the gene expression levels. A high score indicates patient has poor prognosis and a low score indicates the patient has good prognosis for relapse-free survival.

A clinician will measure the gene expression level of the 12 genes in a patient's tumor tissue. Then a prognostic score will be calculated based on the following formula $$\sum_{i=1}^{12} (\text{gene } i\,\beta) \times (\text{gene } i \text{ expression level})$$

where the beta values for each of the 12 genes is obtained from Cox Hazard Regression model. For this to be clinically useful, the beta values are re-calculated for each of the 12 genes using the final platform used to measure gene expression levels. The final score for a given patient will determine the prognosis and outcome of the patient, whereby the calculated score is compared to the previously calculated scores split into two cohorts such that high score=poor prognosis; low score=good prognosis. FIGS. 6A to 6C, and FIGS. 7A to 7C show two independent large data sets (>1000 patients) where we calculated the score for each patient and then split the patient cohort into two equal sized groups—one group is called the "high score" group and the other group is the "low score" group. The cut points for high and low scores will depend on the platform used to assess the gene expression levels.

The gene sequences that may be detected for each of the 12 genes in the signature are provided in the paragraphs herein. The GenBank Accessions for each of the 12 genes are listed below and hereby incorporated by reference:

```
EPS15: NM_001981.2 Homo sapiens epidermal growth factor receptor pathway
substrate 15 (EPS15), transcript variant 1, mRNA. The sequence is as follows:
                                                              (SEQ ID NO: 1)
GGCCTCGCCTGCGGCCGCTCCCTCCGCCTCCTCCCCGCCCCGAGCCCCAGTCAGCCCGTCTTCCTTCCCC

TCCCTTGCATGATGGAAACACCATGGCTGCGGCGGCCCAGCTCTCTCTGACACAGTTATCAAGTGGGAAT

CCTGTATATGAAAAATACTATAGACAGGTTGATACAGGCAATACTGGAAGGGTGTTGGCTTCTGATGCTG

CTGCTTTCCTGAAAAAATCAGGGCTTCCAGACTTGATACTTGGAAAGATTTGGGATTTAGCCGACACAGA

TGGCAAAGGTATCCTGAACAAACAAGAATTCTTTGTTGCTTTGCGTCTTGTGGCATGTGCCCAGAATGGA

TTGGAAGTTTCACTAAGTAGTTTGAACCTGGCTGTTCCTCCACCAAGATTTCATGATACCAGTAGTCCTT

TGCTAATCAGTGGAACCTCTGCAGCTGAGCTCCCATGGGCTGTAAAACCTGAAGATAAGGCCAAATATGA

TGCAATATTTGATAGTTTAAGCCCAGTGAATGGATTTCTGTCTGGTGATAAAGTGAAACCAGTGTTGCTC

AACTCTAAGTTACCTGTGGATATCCTTGGAAGAGTTTGGGAGTTGAGTGATATTGACCATGATGGAATGC
```

-continued

```
TTGACAGAGATGAGTTTGCAGTTGCCATGTTTTTGGTATACTGTGCACTGGAGAAAGAACCTGTGCCAAT
GTCCTTGCCTCCAGCCTTGGTGCCACCATCTAAGAGAAAAACGTGGGTTGTATCCCCTGCAGAAAAAGCT
AAATATGATGAAATCTTCCTGAAAACTGATAAAGATATGGACGGATTTGTGTCTGGATTGGAGGTCCGTG
AAATATTCTTGAAAACAGGTTTACCTTCTACCTTACTAGCCCATATATGGTCATTATGCGACACAAAGGA
CTGTGGGAAGCTTTCAAAGGATCAGTTTGCCTTGGCTTTTCACTTAATCAGTCAGAAGTTAATCAAGGGC
ATTGATCCTCCTCACGTTCTTACTCCTGAAATGATTCCACCATCAGACAGGGCCAGTTTACAAAAGAACA
TCATAGGATCAAGTCCTGTTGCAGATTTCTCTGCTATTAAGGAACTAGATACTCTTAACAATGAAATAGT
TGACCTACAGAGGGAAAAGAATAATGTGGAACAGGACCTTAAGGAGAAGGAAGATACTATTAAACAGAGG
ACAAGTGAGGTTCAGGATCTTCAAGATGAAGTTCAAAGGGAGAATACTAATCTGCAAAAACTACAGGCCC
AGAAACAGCAGGTACAGGAACTCCTTGATGAACTGGATGAGCAGAAAGCCCAGCTGGAGGAGCAACTCAA
GGAAGTCAGAAAGAAATGTGCTGAGGAGGCCCAACTGATCTCTTCTCTGAAAGCTGAATTAACTAGTCAG
GAATCGCAGATCTCCACTTACGAAGAAGAATTGGCAAAAGCTAGAGAAGAGCTGAGCCGTCTACAGCAAG
AAACAGCAGAATTGGAGGAGAGTGTAGAGTCAGGGAAGGCTCAGTTGGAACCTCTTCAGCAGCACCTACA
AGATTCACAACAGGAAATTAGTTCAATGCAAATGAAACTGATGGAAATGAAAGATTTGGAAAATCATAAT
AGTCAGTTAAATTGGTGCAGTAGCCCACACAGCATTCTTGTAAACGGAGCTACAGATTATTGCAGCCTCA
GCACCAGCAGCAGTGAAACAGCCAACCTTAATGAACATGTTGAAGGCCAGAGCAACCTAGAGTCTGAGCC
CATACACCAGGAATCTCCAGCAAGAAGTAGTCCTGAACTACTGCCTTCTGGTGTGACTGATGAAAATGAG
GTGACTACAGCTGTTACTGAAAAAGTTTGTTCTGAACTCGACAATAATAGACATTCAAAAGAGGAAGATC
CATTTAATGTAGACTCAAGTTCGCTGACAGGTCCAGTTGCAGATACAAACTTGGATTTTTTCCAGTCTGA
TCCTTTTGTTGGCAGTGATCCTTTCAAGGATGATCCTTTTGGAAAAATCGATCCATTTGGTGGTGATCCT
TTCAAAGGTTCAGATCCATTTGCATCAGACTGTTTCTTCAGGCAATCTACTGATCCTTTTGCCACTTCAA
GCACTGACCCTTTCAGTGCAGCCAACAATAGCAGTATTACATCGGTAGAAACGTTGAAGCACAATGATCC
TTTTGCTCCTGGTGGAACAGTTGTTGCAGCAAGCGATTCAGCCACAGACCCCTTTGCTTCTGTTTTTGGG
AATGAATCATTTGGAGGTGGATTTGCTGACTTCAGCACATTGTCAAAGGTCAACAATGAAGATCCTTTTC
GTTCAGCCACATCGAGCTCTGTCAGCAACGTAGTGATTACAAAAAATGTATTTGAGGAAACATCGGTCAA
AAGTGAAGATGAACCCCCAGCACTGCCACCAAAGATCGGAACTCCAACAAGACCCTGCCCTCTACCACCT
GGGAAAAGATCCATCAACAAATTGGATTCTCCTGATCCCTTTAAACTGAATGATCCATTTCAGCCTTTCC
CAGGCAACGATAGCCCCAAAGAAAAAGATCCTGAAATATTTTGTGATCCATTCACTTCTGCTACTACCAC
TACCAATAAAGAGGCTGATCCAAGCAATTTTGCCAACTTCAGTGCTTATCCCTCTGAAGAAGATATGATC
GAATGGGCCAAGAGGGAAAGTGAGAGAGAGGAAGAGCAGAGGCTTGCCCGACTAAATCAGCAGGAACAAG
AAGACTTAGAACTGGCTATTGCACTCAGCAAATCTGAGATATCAGAAGCATGAAGAATTCTCTTGTTCTT
TGGCAACAATATAGTATTCTTCTTCCTGAATACTGAAACTATTTACAATGTGTATCAAAACTACCTGTGA
GCATGGGAATACAAAAGGTTTGAGATTCCTGTAAATGTGACAAAATTTTAGGATTTTTTTTTTTCTTCA
TTACAGATTCGTCTTTTTTTTTTTTCTTATAAAAGCCGTAACCCAGTCAGACAAATTCACCTTCACTTA
GGCCCCTGTTCTGGTATACATTTACTGTGAGCTTTTGCCTGCCTGTGCTATTTTACTTGTAAAGCTAGAG
CACCCAAGCTTCTGCCTTCTGGAATATAGAGAAATAGTTTCACCCTGCACTACCCTGTTCTGTAGTTATT
CTGATGATAGCCAGTGAGGTTCTTAAAGTTTGCAGTATTCTCCCCTGATTGGAATGGTTGAGTGAGGGTA
AGGGAAAGAATATCTTATTTCTTTTATGATTGGTGCAAATTGGCTAAAGTGCATTTTTAAATTTCCTCTA
CTTAATTTGTTTTTCAGAGATAAGGAAAAATATTTTGCACAGATTTACTCCACTATGGAAAAGGGATGCT
GTAGGTTGAACCATTATAGCCTCAGATTCGATCTTTTCCTAACTAAAAATATTAAAGCCTCATGTGTGAA
```

-continued

```
ATAAATTTTTAAAAAGATTTATCTGGATTTAGAGAATTTTAGATCAACAGATACCTCTCAGTGTGTTTGC

TAATTAATAAAAATCAGTTTCTTACAAATAAAGTTTGTAAGAAAATGTTCATTTTAAGTGATAGATAGTG

GAGAAAATTTATCACCTAAAATATACCCATCAGTATAAGGCAAGCAAAAGTCTTAACATGGCAGCCATTC

TGCCTTTGCCGTGGCCCTGTCCTGTTTAGTTCTTAGTGGGTTAATTTTTGTACTTTTGCAGAAGAAACTT

CAGCAAGCTAGAACTGGAAGGTACTTTAATTTTTCATATATATTTGTTTTTTTTTTTTAATGAAGGCTC

ATTTACTTGAAATGTAAAAACTTTCACTGAATACAAATAGAAAAGTGATGTGTTTTATATCATATTGCT

TTTTGTCCATCTTTGTGGTTTAGTTTATTTACTCACTTCATGTTTTTCACCTATAAAATTGTCAAGCTAG

CAAAAAAACTCTTGTTTTTTTAATTGGGAGAGAAGAGACCTGCCAGATTATCAGACCTCTTCATGTTAAA

AGACCATCTCCTGTAAAACTGACCTAGTGGACAAGCTGAATTTGAAATAGACTGTGAAGTAAGCTGTAAC

TTGTCATTTTAATTTTGTTTAACACGGTTACTGACTTAGATGATGTATTAAATACCAAGATAAAGAAAAA

TGCACCTAAAATCTAATTAGAATTCTCTGGGTCAACAAGTCAAGGTGGTATTGATCTGTGTTAATCTGAG

TAACTTATTGCCTAGCCTATAAATAAATTCCAAAATATCCAATTCATTTCTTCTTGAAATGGTGCTTGTT

TTGTTTTCTTTCCATTACACAATTAGACTCCTACAGTTTAAAACAAACTTTAAACCACTATCTTGCACTG

CTAACTTTTTTCTACCTTTGTAAATAGAAACATTTCTGCATAAAAGTCATACATATGAAGCAAGGGCTGA

ATCATAATCACAAGGCTTAATTTTGATAAACGAATCCAGTGACCTAAGGATTTTCTGCAAAATTTGACTG

GGAGTTGTGATAGGTGGTATTTTTGTTTATTTTCTTCCTCTTACTCCTTAGGATAAAGGTAAGTTGACTT

GAACAACTTTCTTTTGCACTGGGAAAATAAGCAAATGTTTAAATGCTTCAAAAAAATTTTCAATTAAACT

CAAATATTAAATATCTATAACTTATAAACACCAACTTTCAATGTAATAAATGTATCCTAATCTTATGTAT

GTTTAACTGGATTACATAGATTTTTATCTTTTGTTAAAATGTGTATACCCCGTGGACCAACATAATATTA

AAGTATGTATATATTATATAAATATATATGTATATGTGCTCGCTTGTGTAGGATGAATGTCTTAGAGTCG

TTTGTGGTATTTTATGTTGTTGACTCTGGCTCCAGGGCCTGTGCTTGAAAAGGACAGATAAGTATTGCCC

AGAGCTAAGTGGCACTACTTACAAAGTTTTAAATGTCTTCTACATACTGATTCATGTTTATTTGAGCTCT

CTTTATAGAATTTTCTCTTAAAGTTTCAAACCTCTAAGTTGTAGCCTGTAATTATGAGAACAGTAAACTT

TAAGTAATAATAAAGAATCCCATCCATATATCCAATTTGCAATTGAGTTTTGCATGGTTCTCTGATTATG

TCCATGCTGTGTCCAAGGAGGAGTAGGTACATACAATCAGCACAGATTAATATATGTAAAGGGTTTGGGA

CAGCACCTGGTATAGAATAAATAATAAATGTAAACTATTA.
```

MELK: NM_014791.3 Homo sapiens maternal embryonic leucine zipper kinase (MELK), transcript variant 1, mRNA. The sequence is as follows:

(SEQ ID NO: 2)

```
GAGATTTGATTCCCTTGGCGGGCGGAAGCGGCCACAACCCGGCGATCGAAAAGATTCTTAGGAACGCCGT

ACCAGCCGCGTCTCTCAGGACAGCAGGCCCCTGTCCTTCTGTCGGGCGCCGCTCAGCCGTGCCCTCCGCC

CCTCAGGTTCTTTTTCTAATTCCAAATAAACTTGCAAGAGGACTATGAAAGATTATGATGAACTTCTCAA

ATATTATGAATTACATGAAACTATTGGGACAGGTGGCTTTGCAAAGGTCAAACTTGCCTGCCATATCCTT

ACTGGAGAGATGGTAGCTATAAAAATCATGGATAAAAACACACTAGGGAGTGATTTGCCCCGGATCAAAA

CGGAGATTGAGGCCTTGAAGAACCTGAGACATCAGCATATATGTCAACTCTACCATGTGCTAGAGACAGC

CAACAAAATATTCATGGTTCTTGAGTACTGCCCTGGAGGAGAGCTGTTTGACTATATAATTTCCCAGGAT

CGCCTGTCAGAAGAGGAGACCCGGGTTGTCTTCCGTCAGATAGTATCTGCTGTTGCTTATGTGCACAGCC

AGGGCTATGCTCACAGGGACCTCAAGCCAGAAAATTTGCTGTTTGATGAATATCATAAATTAAAGCTGAT

TGACTTTGGTCTCTGTGCAAAACCCAAGGGTAACAAGGATTACCATCTACAGACATGCTGTGGGAGTCTG

GCTTATGCAGCACCTGAGTTAATACAAGGCAAATCATATCTTGGATCAGAGGCAGATGTTTGGAGCATGG

GCATACTGTTATATGTTCTTATGTGTGGATTTCTACCATTTGATGATGATAATGTAATGGCTTTATACAA

GAAGATTATGAGAGGAAAATATGATGTTCCCAAGTGGCTCTCTCCCAGTAGCATTCTGCTTCTTCAACAA
```

-continued

```
ATGCTGCAGGTGGACCCAAAGAAACGGATTTCTATGAAAAATCTATTGAACCATCCCTGGATCATGCAAG

ATTACAACTATCCTGTTGAGTGGCAAAGCAAGAATCCTTTTATTCACCTCGATGATGATTGCGTAACAGA

ACTTTCTGTACATCACAGAAACAACAGGCAAACAATGGAGGATTTAATTTCACTGTGGCAGTATGATCAC

CTCACGGCTACCTATCTTCTGCTTCTAGCCAAGAAGGCTCGGGGAAAACCAGTTCGTTTAAGGCTTTCTT

CTTTCTCCTGTGGACAAGCCAGTGCTACCCCATTCACAGACATCAAGTCAAATAATTGGAGTCTGGAAGA

TGTGACCGCAAGTGATAAAAATTATGTGGCGGGATTAATAGACTATGATTGGTGTGAAGATGATTTATCA

ACAGGTGCTGCTACTCCCCGAACATCACAGTTTACCAAGTACTGGACAGAATCAAATGGGGTGGAATCTA

AATCATTAACTCCAGCCTTATGCAGAACACCTGCAAATAAATTAAAGAACAAAGAAAATGTATATACTCC

TAAGTCTGCTGTAAAGAATGAAGAGTACTTTATGTTTCCTGAGCCAAAGACTCCAGTTAATAAGAACCAG

CATAAGAGAGAAATACTCACTACGCCAAATCGTTACACTACACCCTCAAAAGCTAGAAACCAGTGCCTGA

AAGAAACTCCAATTAAAATACCAGTAAATTCAACAGGAACAGACAAGTTAATGACAGGTGTCATTAGCCC

TGAGAGGCGGTGCCGCTCAGTGGAATTGGATCTCAACCAAGCACATATGGAGGAGACTCCAAAAAGAAAG

GGAGCCAAAGTGTTTGGGAGCCTTGAAAGGGGGTTGGATAAGGTTATCACTGTGCTCACCAGGAGCAAAA

GGAAGGGTTCTGCCAGAGACGGGCCCAGAAGACTAAAGCTTCACTATAACGTGACTACAACTAGATTAGT

GAATCCAGATCAACTGTTGAATGAAATAATGTCTATTCTTCCAAAGAAGCATGTTGACTTTGTACAAAAG

GGTTATACACTGAAGTGTCAAACACAGTCAGATTTTGGGAAAGTGACAATGCAATTTGAATTAGAAGTGT

GCCAGCTTCAAAAACCCGATGTGGTGGGTATCAGGAGGCAGCGGCTTAAGGGCGATGCCTGGGTTTACAA

AAGATTAGTGGAAGACATCCTATCTAGCTGCAAGGTATAATTGATGGATTCTTCCATCCTGCCGGATGAG

TGTGGGTGTGATACAGCCTACATAAAGACTGTTATGATCGCTTTGATTTTAAAGTTCATTGGAACTACCA

ACTTGTTTCTAAAGAGCTATCTTAAGACCAATATCTCTTTGTTTTTAAACAAAAGATATTATTTTGTGTA

TGAATCTAAATCAAGCCCATCTGTCATTATGTTACTGTCTTTTTTAATCATGTGGTTTTGTATATTAATA

ATTGTTGACTTTCTTAGATTCACTTCCATATGTGAATGTAAGCTCTTAACTATGTCTCTTTGTAATGTGT

AATTTCTTTCTGAAATAAAACCATTTGTGAATATAG.
```

NUF2: NM_145697.2 *Homo sapiens* NUF2, NDC80 kinetochore complex component (NUF2), transcript variant 1, mRNA. The sequence is as follows:

(SEQ ID NO: 3)

```
GCGGAATGGGGCGGGACTTCCAGTAGGAGGCGGCAAGTTTGAAAAGTGATGACGGTTGACGTTTGCTGAT

TTTTGACTTTGCTTGTAGCTGCTCCCCGAACTCGCCGTCTTCCTGTCGGCGGCCGGCACTGTAGGTGAGC

GCGAGAGGACGGAGGAAGGAAGCCTGCAGACAGACGCCTTCTCCATCCCAAGGCGCGGGCAGGTGCCGGG

ACGCTGGGCCTGGCGGTGTTTTCGTCGTGCTCAGCGGTGGGAGGAGGCGGAAGAAACCAGAGCCTGGGAG

ATTAACAGGAAACTTCCAAGATGGAAACTTTGTCTTTCCCCAGATATAATGTAGCTGAGATTGTGATTCA

TATTCGCAATAAGATCTTAACAGGAGCTGATGGTAAAAACCTCACCAAGAATGATCTTTATCCAAATCCA

AAGCCTGAAGTCTTGCACATGATCTACATGAGAGCCTTACAAATAGTATATGGAATTCGACTGGAACATT

TTTACATGATGCCAGTGAACTCTGAAGTCATGTATCCACATTTAATGGAAGGCTTCTTACCATTCAGCAA

TTTAGTTACTCATCTGGACTCATTTTTGCCTATCTGCCGGGTGAATGACTTTGAGACTGCTGATATTCTA

TGTCCAAAAGCAAAACGGACAAGTCGGTTTTAAGTGGCATTATCAACTTTATTCACTTCAGAGAAGCAT

GCCGTGAAACGTATATGGAATTTCTTTGGCAATATAAATCCTCTGCGGACAAAATGCAACAGTTAAACGC

CGCACACCAGGAGGCATTAATGAAACTGGAGAGACTTGATTCTGTTCCAGTTGAAGAGCAAGAAGAGTTC

AAGCAGCTTTCAGATGGAATTCAGGAGCTACAACAATCACTAAATCAGGATTTTCATCAAAAAACGATAG

TGCTGCAAGAGGGAAATTCCCAAAAGAAGTCAAATATTTCAGAGAAAACCAAGCGTTTGAATGAACTAAA

ATTGTCGGTGGTTTCTTTGAAAGAAATACAAGAGAGTTTGAAAACAAAAATTGTGGATTCTCCAGAGAAG

TTAAAGAATTATAAAGAAAAAATGAAAGATACGGTCCAGAAGCTTAAAAATGCCAGACAAGAAGTGGTGG
```

-continued

AGAAATATGAAATCTATGGAGACTCAGTTGACTGCCTGCCTTCATGTCAGTTGGAAGTGCAGTTATATCA

AAAGAAAATACAGGACCTTTCAGATAATAGGGAAAAATTAGCCAGTATCTTAAAGGAGAGCCTGAACTTG

GAGGACCAAATTGAGAGTGATGAGTCAGAACTGAAGAAATTGAAGACTGAAGAAATTCGTTCAAAAGAC

TGATGATTGTGAAGAAGGAAAAACTTGCCACAGCACAATTCAAAATAAATAAGAAGCATGAAGATGTTAA

GCAATACAAACGCACAGTAATTGAGGATTGCAATAAAGTTCAAGAAAAAGAGGTGCTGTCTATGAACGA

GTAACCACAATTAATCAAGAAATCCAAAAAATTAAACTTGGAATTCAACAACTAAAAGATGCTGCTGAAA

GGGAGAAACTGAAGTCCCAGGAAATATTTCTAAACTTGAAAACTGCTTTGGAGAAATACCACGACGGTAT

TGAAAAGGCAGCAGAGGACTCCTATGCTAAGATAGATGAGAAGACAGCTGAACTGAAGAGGAAGATGTTC

AAAATGTCAACCTGATTAACAAAATTACATGTCTTTTTGTAAATGGCTTGCCATCTTTTAATTTTCTATT

TAGAAAGAAAAGTTGAAGCGAATGGAAGTATCAGAAGTACCAAATAATGTTGGCTTCATCAGTTTTTATA

CACTCTCATAAGTAGTTAATAAGATGAATTTAATGTAGGCTTTTATTAATTTATAATTAAAATAACTTGT

GCAGCTATTCATGTCTCTACTCTGCCCCTTGTTGTAAATAGTTTGAGTAAAACAAAACTAGTTACCTTTG

AAATATATATATTTTTTTCTGTTACTATC.

RNASEH2A: NM_006397.2 Homo sapiens ribonuclease H2 subunit A (RNASEH2A),
mRNA. The sequence is as follows:

(SEQ ID NO: 4)

GCGCCGAGACCCGCTCCTGCAGTATTAGTTCTTGCAGCTGGTGGTGGCGGCTGAGGCGGCATGGATCTCA

GCGAGCTGGAGAGAGACAATACAGGCCGCTGTCGCCTGAGTTCGCCTGTGCCCGCGGTGTGCCGCAAGGA

GCCTTGCGTCCTGGGCGTCGATGAGGCGGGCAGGGGCCCCGTGCTGGGCCCCATGGTCTACGCCATCTGT

TATTGTCCCCTGCCTCGCCTGGCAGATCTGGAGGCGCTGAAAGTGGCAGACTCAAAGACCCTATTGGAGA

GCGAGCGGGAAAGGCTGTTTGCGAAAATGGAGGACACGGACTTTGTCGGCTGGGCGCTGGATGTGCTGTC

TCCAAACCTCATCTCTACCAGCATGCTTGGGCGGGTCAAATACAACCTGAACTCCCTGTCACATGATACA

GCCACTGGGCTTATACAGTATGCATTGGACCAGGGCGTGAACGTCACCCAGGTATTCGTGGACACCGTAG

GGATGCCAGAGACATACCAGGCGCGGCTGCAGCAAAGTTTTCCCGGGATTGAGGTGACGGTCAAGGCCAA

AGCAGATGCCCTCTACCCGGTGGTTAGTGCTGCCAGCATCTGTGCCAAGGTGGCCCGGGACCAGGCCGTG

AAGAAATGGCAGTTCGTGGAGAAACTGCAGGACTTGGATACTGATTATGGCTCAGGCTACCCCAATGATC

CCAAGACAAAAGCGTGGTTGAAGGAGCACGTGGAGCCTGTGTTCGGCTTCCCCCAGTTTGTCCGGTTCAG

CTGGCGCACGGCCCAGACCATCCTGGAGAAAGAGGCGGAAGATGTTATATGGGAGGACTCAGCATCCGAG

AATCAGGAGGGACTCAGGAAGATCACATCCTACTTCCTCAATGAAGGGTCCCAAGCCCGTCCCCGTTCTT

CCCACCGATATTTCCTGGAACGCGGCCTGGAGTCAGCAACCAGCCTCTAGCAGCTGCCTCTACGCGCTCT

ACCTGCTTCCCCAACCCAGACATTAAAATTGTTTAAGGAGAACCACACGTAGGGGATGTACTTTTGGGAC

AGAAGCAAGGTGGGAGTGTGCTCTGCAGCCGGGTCCAGCTACTTCCTTTTGGAACCTTAAATAGAATGGG

TGTTGGTTGATTAATTTTATTTAAAAAA.

S100P: NM_005980.2 Homo sapiens S100 calcium binding protein P (S100P), mRNA.
The sequence is as follows:

(SEQ ID NO: 5)

TGAGGCTGCCTTATAAAGCACCAAGAGGCTGCCAGTGGGACATTTTCTCGGCCCTGCCAGCCCCCAGGAG

GAAGGTGGGTCTGAATCTAGCACCATGACGGAACTAGAGACAGCCATGGGCATGATCATAGACGTCTTTT

CCCGATATTCGGGCAGCGAGGGCAGCACGCAGACCCTGACCAAGGGGGAGCTCAAGGTGCTGATGGAGAA

GGAGCTACCAGGCTTCCTGCAGAGTGGAAAAGACAAGGATGCCGTGGATAAATTGCTCAAGGACCTGGAC

GCCAATGGAGATGCCCAGGTGGACTTCAGTGAGTTCATCGTGTTCGTGGCTGCAATCACGTCTGCCTGTC

ACAAGTACTTTGAGAAGGCAGGACTCAAATGATGCCCTGGAGATGTCACAGATTCCTGGCAGAGCCATGG

TCCCAGGCTTCCCCAAAAGTGTTTGTTGGCAATTATTCCCCTAGGCTGAGCCTGCTCATGTACCTCTGATT

AATAAATGCTTATGAAATGA.

THYN1: NM_014174.2 *Homo sapiens* thymocyte nuclear protein 1 (THYN1), transcript variant 1, mRNA. The sequence is as follows:

(SEQ ID NO: 6)

GCGGGGGTCGCGCTGCACAGCCTGCGGCGCAGCGGAGGCGGACCGCAGTCGAGTCTGCAGAGTGTTGGGT

CTGTAGCCAGCAAATTACTTCATCATCTAGATTATCCATTCAGTTGATCCTAATTAGCAAGGATAACAAG

GTAACACAAGGCTTACTTATATTCACCCAACAAAAGTGTCTCTGTGGAGCCACTTCCCAGTGAACTACAT

ACTGAGATAGGGGTTCCTGGATGAGAAGGACCAAGGACAGAACCGAGAAGAGTTTAGGGGCAGGTTATGC

GAGATGGAAATGGCGCAGATAACGGAGGGAAGGATTTGAGGGCTCAAACGTAGGCGTCTGTGTTTCGCAA

AAGTTGGAGACGTTCTAGGCTGCCTCTCGTTGCCTCCATCTCGCTCTGCGCGGGTTTTGGAGGACATTAG

CATTCTTTCTTGTATCTCCGTTGATTCCAGAATCGTCCGCACTAAAGTCCCCTGCAGCGTGACCATGTCG

AGACCCCGGAAGAGGCTGGCTGGGACTTCTGGTTCAGACAAGGGACTATCAGGAAAACGCACCAAAACTG

AGAACTCAGGTGAGGCATTAGCTAAAGTGGAGGACTCCAACCCTCAGAAGACTTCAGCCACTAAAAACTG

TTTGAAGAATCTAAGCAGCCACTGGCTGATGAAGTCAGAGCCAGAGAGCCGCCTAGAGAAAGGTGTAGAT

GTGAAGTTCAGCATTGAGGATCTCAAAGCACAGCCCAAACAGACAACATGCTGGGATGGTGTTCGTAACT

ACCAGGCTCGGAACTTCCTTAGAGCCATGAAGCTGGGAGAAGAAGCCTTCTTCTACCATAGCAACTGCAA

AGAGCCAGGCATCGCAGGACTCATGAAGATCGTGAAAGAGGCTTACCCAGACCACACACAGTTTGAGAAA

AACAATCCCCATTATGACCCATCTAGCAAAGAGGACAACCCTAAGTGGTCCATGGTGGATGTACAGTTTG

TTCGGATGATGAAACGTTTCATTCCCCTGGCTGAGCTCAAATCCTATCATCAAGCTCACAAAGCTACTGG

TGGCCCCTTAAAAAATATGGTTCTCTTCACTCGCCAGAGATTATCAATCCAGCCCCTGACCCAGGAAGAG

TTTGATTTTGTTTTGAGCCTGGAGGAAAAGGAACCAAGTTAACTGAGATACTGCTGCTGGAATGGGCGAG

ACATTGCTGCAAAGAAGTCAAGCTTTTTTCAGACAAAAGGTGTGAGGGGGCTTGCTTGGTATGCTTACCT

GGGCTTGTGTACCTCAGTGGTTTTTGTGTACTTTTTTCAATAAAATATCAAAGTTGAAGAAAA.

TIMM17A: NM_006335.2 *Homo sapiens* translocase of inner mitochondrial membrane 17 homolog A (yeast) (TIMM17A), mRNA. The sequence is as follows:

(SEQ ID NO: 7)

AGCTTGCCCGGCATCACTCGCGGCATTGGAGTCAAGATGGAGGAGTACGCGCGAGAGCCTTGCCCATGGC

GAATTGTGGATGACTGTGGTGGGGCCTTTACGATGGGTACCATTGGTGGTGGTATCTTTCAAGCAATCAA

AGGTTTTCGCAATTCTCCAGTGGGAGTAAACCACAGACTACGAGGGAGTTTGACAGCTATTAAAACCAGG

GCTCCACAGTTAGGAGGTAGCTTTGCAGTTTGGGGAGGGCTGTTTTCCATGATTGACTGTAGTATGGTTC

AAGTCAGAGGAAAGGAAGATCCCTGGAACTCCATCACAAGTGGTGCCTTAACGGGAGCCATACTGGCAGC

AAGAAATGGACCAGTGGCCATGGTTGGGTCAGCCGCAATGGGTGGCATTCTCCTAGCTTTAATTGAAGGA

GCTGGTATCTTGTTGACAAGATTTGCCTCTGCACAGTTTCCCAATGGTCCTCAGTTTGCAGAAGACCCCT

CCCAGTTGCCTTCAACTCAGTTACCTTCCTCACCTTTTGGAGACTATCGACAATATCAGTAGGACTTCTT

TCCTAGGATTTCTTTAACAGAACGAGTTGTGGTTCGAGAAGGATTTCAGAAGATCAAGTTACAGTCTGTT

TTTAAAACCATAGGTGGGACAGCTATGGCCAATAGGCTATAAAGAGACATTTAGCACTTTTTTCTATTTA

AAGGAACAAGCGGGGAAGGGTGCTAAAAGATAATACGTTTATTTATTCACACTTGAATTGCATTTGTGAT

CAAAATAAATGTTTAAATCGCTAAAGGAAAATACAGTAAGTGCTTGAAAGATGAAGGACCAAAAGGCCAA

AAAACAGTGAAATATGATCATCATCTCCTTGCGGACTTCTCTGCCTGGTTTTGTGTGTTCTGTTATTCAA

ACAATAAAAAGCTGGTGGAACTTACTCTTTCTTTTAAGATAAGTTGTAGACTTCGATGTTTCATGCTCAT

GTACTTCAAATAATGCATGTTTTATAGTTAGTCCCTCATCACTTGAAGTGACTTCTGAGAATTATGCAGA

GTCAACATGGATCATTTCACAGTGAGATGCTTTATGGATTGAAGGATATGGTAAAATGTTTATAGTTTAC

TTTGAAAGTAAAATATACTATGTCTTGGTTTTGAGGATATTGGATACAAAACTCTCTTCCTTTAGGGCTA

CTGAGTCTTGATTCCTGATCATCAGAAATTTCACCAGAAACAACTTGCTTCCAATATACCCAATTCTATA

-continued

TGAAGAATTCATGGAGAGTGTACTGGCACTGGAAGAGTTTAGTGTTTCTTGTATGCTTGAAAATAAAGTA

TGTACTGTTTTGAATGTGTTCCAAGTCCTCTGCATAAACGATGTATTTTGGGGTCTGGTTGGGCCTGGAA

AATGGATGAGCACTTCAGAACAGGTCATTTTCCTGATATTGGAAGTGACATGTGGCCCTATAGGAGGCAT

GATGTTAGTTAATTACACATTTGCCTACATCTGTGGGAAATGGAGAACAAAGCCATGTGGGTACTGTAAA

CACACGTTTATCTTTTGGCCCAATGCCATACATATGGTAGGCATTTAATTACTGATTGTGTTTGGATAAT

TTGGGAATTTTCGACTGTGGTAAAATATACATAAAATAATACTTATTAAAAAAAAAAAAAAAAAA.

TSC1: NM_000368.4 *Homo sapiens* tuberous sclerosis 1 (TSC1), transcript variant 1, mRNA. The sequence is as follows:

(SEQ ID NO: 8)

ACGACGGGGGAGGTGCTGTACGTCCAAGATGGCGGCGCCCTGTAGGCTGGAGGGACTGTGAGGTAAACAG

CTGAGGGGGAGGAGACGGTGGTGACCATGAAAGACACCAGGTTGACAGCACTGGAAACTGAAGTACCAGT

TGTCGCTAGAACAGTTTGGTAGTGGCCCCAATGAAGAACCTTCAGAACCTGTAGCACACGTCCTGGAGCC

AGCACAGCGCCTTCGAGCGAGAGAATGGCCCAACAAGCAAATGTCGGGGAGCTTCTTGCCATGCTGGACT

CCCCCATGCTGGGTGTGCGGGACGACGTGACAGCTGTCTTTAAAGAGAACCTCAATTCTGACCGTGGCCC

TATGCTTGTAAACACCTTGGTGGATTATTACCTGGAAACCAGCTCTCAGCCGGCATTGCACATCCTGACC

ACCTTGCAAGAGCCACATGACAAGCACCTCTTGGACAGGATTAACGAATATGTGGGCAAAGCCGCCACTC

GTTTATCCATCCTCTCGTTACTGGGTCATGTCATAAGACTGCAGCCATCTTGGAAGCATAAGCTCTCTCA

AGCACCTCTTTTGCCTTCTTTACTAAAATGTCTCAAGATGGACACTGACGTCGTTGTCCTCACAACAGGC

GTCTTGGTGTTGATAACCATGCTACCAATGATTCCACAGTCTGGGAAACAGCATCTTCTTGATTTCTTTG

ACATTTTTGGCCGTCTGTCATCATGGTGCCTGAAGAAACCAGGCCACGTGGCGGAAGTCTATCTCGTCCA

TCTCCATGCCAGTGTGTACGCACTCTTTCATCGCCTTTATGGAATGTACCCTTGCAACTTCGTCTCCTTT

TTGCGTTCTCATTACAGTATGAAAGAAAACCTGGAGACTTTTGAAGAAGTGGTCAAGCCAATGATGGAGC

ATGTGCGAATTCATCCGGAATTAGTGACTGGATCCAAGGACCATGAACTGGACCCTCGAAGGTGGAAGAG

ATTAGAAACTCATGATGTTGTGATCGAGTGTGCCAAAATCTCTCTGGATCCCACAGAAGCCTCATATGAA

GATGGCTATTCTGTGTCTCACCAAATCTCAGCCCGCTTTCCTCATCGTTCAGCCGATGTCACCACCAGCC

CTTATGCTGACACACAGAATAGCTATGGGTGTGCTACTTCTACCCCTTACTCCACGTCTCGGCTGATGTT

GTTAAATATGCCAGGGCAGCTACCTCAGACTCTGAGTTCCCCATCGACACGGCTGATAACTGAACCACCA

CAAGCTACTCTTTGGAGCCCATCTATGGTTTGTGGTATGACCACTCCTCCAACTTCTCCTGGAAATGTCC

CACCTGATCTGTCACACCCTTACAGTAAAGTCTTTGGTACAACTGCAGGTGGAAAAGGAACTCCTCTGGG

AACCCCAGCAACCTCTCCTCCTCCAGCCCCACTCTGTCATTCGGATGACTACGTGCACATTTCACTCCCC

CAGGCCACAGTCACACCCCCCAGGAAGGAAGAGAGAATGGATTCTGCAAGACCATGTCTACACAGACAAC

ACCATCTTCTGAATGACAGAGGATCAGAAGAGCCACCTGGCAGCAAAGGTTCTGTCACTCTAAGTGATCT

TCCAGGGTTTTTAGGTGATCTGGCCTCTGAAGAAGATAGTATTGAAAAAGATAAAGAAGAAGCTGCAATA

TCTAGAGAACTTTCTGAGATCACCACAGCAGAGGCAGAGCCTGTGGTTCCTCGAGGAGGCTTTGACTCTC

CCTTTTACCGAGACAGTCTCCCAGGTTCTCAGCGGAAGACCCACTCGGCAGCCTCCAGTTCTCAGGGCGC

CAGCGTGAACCCTGAGCCTTTACACTCCTCCCTGGACAAGCTTGGGCCTGACACACCAAAGCAAGCCTTT

ACTCCCATAGACCTGCCCTGCGGCAGTGCTGATGAAAGCCCTGCGGGAGACAGGGAATGCCAGACTTCTT

TGGAGACCAGTATCTTCACTCCCAGTCCTTGTAAAATTCCACCTCCGACGAGAGTGGGCTTTGGAAGCGG

GCAGCCTCCCCCGTATGATCATCTTTTTGAGGTGGCATTGCCAAAGACAGCCCATCATTTTGTCATCAGG

AAGACTGAGGAGCTGTTAAAGAAAGCAAAGGAAACACAGAGGAAGATGGTGTGCCCTCTACCTCCCCAA

TGGAAGTGCTGGACAGACTGATACAGCAGGGAGCAGACGCGCACAGCAAGGAGCTGAACAAGTTGCCTTT

ACCCAGCAAGTCTGTCGACTGGACCCACTTTGGAGGCTCTCCTCCTTCAGATGAGATCCGCACCCTCCGA

-continued

```
GACCAGTTGCTTTTACTGCACAACCAGTTACTCTATGAGCGTTTTAAGAGGCAGCAGCATGCCCTCCGGA
ACAGGCGGCTCCTCCGCAAGGTGATCAAAGCAGCAGCTCTGGAGGAACATAATGCTGCCATGAAAGATCA
GTTGAAGTTACAAGAGAAGGACATCCAGATGTGGAAGGTTAGTCTGCAGAAAGAACAAGCTAGATACAAT
CAGCTCCAGGAGCAGCGTGACACTATGGTAACCAAGCTCCACAGCCAGATCAGACAGCTGCAGCATGACC
GAGAGGAATTCTACAACCAGAGCCAGGAATTACAGACGAAGCTGGAGGACTGCAGGAACATGATTGCGGA
GCTGCGGATAGAACTGAAGAAGGCCAACAACAAGGTGTGTCACACTGAGCTGCTGCTCAGTCAGGTTTCC
CAAAAGCTCTCAAACAGTGAGTCGGTCCAGCAGCAGATGGAGTTCTTGAACAGGCAGCTGTTGGTTCTTG
GGGAGGTCAACGAGCTCTATTTGGAACAACTGCAGAACAAGCACTCAGATACCACAAAGGAAGTAGAAAT
GATGAAAGCCGCCTATCGGAAAGAGCTAGAAAAAAACAGAAGCCATGTTCTCCAGCAGACTCAGAGGCTT
GATACCTCCCAAAAACGGATTTTGGAACTGGAATCTCACCTGGCCAAGAAAGACCACCTTCTTTTGGAAC
AGAAGAAATATCTAGAGGATGTCAAACTCCAGGCAAGAGGACAGCTGCAGGCCGCAGAGAGCAGGTATGA
GGCTCAGAAAAGGATAACCCAGGTGTTTGAATTGGAGATCTTAGATTTATATGGCAGGTTGGAGAAAGAT
GGCCTCCTGAAAAAACTTGAAGAAGAAAAAGCAGAAGCAGCTGAAGCAGCAGAAGAAAGGCTTGACTGTT
GTAATGACGGGTGCTCAGATTCCATGGTAGGGCACAATGAAGAGGCATCTGGCCACAACGGTGAGACCAA
GACCCCCAGGCCCAGCAGCGCCCGGGGCAGTAGTGGAAGCAGAGGTGGTGGAGGCAGCAGCAGCAGCAGC
AGCGAGCTTTCTACCCCAGAGAAACCCCCACACCAGAGGGCAGGCCCATTCAGCAGTCGGTGGGAGACGA
CTATGGGAGAAGCGTCTGCCAGCATCCCCACCACTGTGGGCTCACTTCCCAGTTCAAAAAGCTTCCTGGG
TATGAAGGCTCGAGAGTTATTTCGTAATAAGAGCGAGAGCCAGTGTGATGAGGACGGCATGACCAGTAGC
CTTTCTGAGAGCCTAAAGACAGAACTGGGCAAAGACTTGGGTGTGGAAGCCAAGATTCCCCTGAACCTAG
ATGGCCCTCACCCGTCTCCCCCGACCCCGGACAGTGTTGGACAGCTACATATCATGGACTACAATGAGAC
TCATCATGAACACAGCTAAGGAATGATGGTCAATCAGTGTTAACTTGCATATTGTTGGCACAGAACAGGA
GGTGTGAATGCACGTTTCAAAGCTTTCCTGTTTCCAGGGTCTGAGTGCAAGTTCATGTGTGGAAATGGGA
CGGAGGTCCTTTGGACAGCTGACTGAATGCAGAACGGTTTTTGGATCTGGCATTGAAATGCCTCTTGACC
TTCCCCTCCACCCGCCCTAACCCCCTCTCATTTACCTCGCAGTGTGTTCTAATCCAAGGGCCAGTTGGTG
TTCCTCAGTAGCTTTACTTTCTTCCTTTCCCCCCCAAATGGTTGCGTCCTTTGAACCTGTGCAATATGAG
GCCAAATTTAATCTTTGAGTCTAACACACCACTTTCTGCTTTCCCGAAGTTCAGATAACTGGGTTGGCTC
TCAATTAGACCAGGTAGTTTGTTGCATTGCAGGTAAGTCTGGTTTTGTCCCTTCCAGGAGGACATAGCCT
GCAAAGCTGGTTGTCTTTACATGAAAGCGTTTACATGAGACTTTCCGACTGCTTTTTTGATTCTGAAGTT
CAGCATCTAAAGCAGCAGGTCTAGAAGAACAACGGTTTATTCATACTTGCATTCTTTTGGCAGTTCTGAT
AAGCTTCCTAGAAAGTTCTGTGTAAACAGAAGCCTGTTTCAGAAATCTGGAGCTGGCACTGTGGAGACCA
CACACCCTTTGGGAAAGCTCTTGTCTCTTCTTCCCCCACTACCTCTTATTTATTTGGTGTTTGCTTGAAT
GCTGGTACTATTGTGACCACAGGCTGGTGTGTAGGTGGTAAAACCTGTTCTCCATAGGAGGGAAGGAGCA
GTCACTGGGAGAGGTTACCCGAGAAGCACTTGAGCATGAGGAACTGCACCTTTAGGCCATCTCAGCTTGC
TGGGCCTTTTGTTAAACCCTTCTGTCTACTGGCCTCCCTTTGTGTGCATACGCCTCTTGTTCATGTCAGC
TTATATGTGACACTGCAGCAGAAAGGCTCTGAAGGTCCAAAGAGTTTCTGCAAAGTGTATGTGACCATCA
TTTCCCAGGCCATTAGGGTTGCCTCACTGTAGCAGGTTCTAGGCTACCAGAAGAGGGGCAGCTTTTTCAT
ACCAATTCCAACTTTCAGGGGCTGACTCTCCAGGGAGCTGATGTCATCACACTCTCCATGTTAGTAATGG
CAGAGCAGTCTAAACAGAGTCCGGGAGAATGCTGGCAAAGGCTGGCTGTGTATACCCACTAGGCTGCCCC
ACGTGCTCCCGAGAGATGACACTAGTCAGAAAATTGGCAGTGGCAGAGAATCCAAACTCAACAAGTGCTC
CTGAAAGAAACGCTAGAAGCCTAAGAACTGTGGTCTGGTGTTCCAGCTGAGGCAGGGGGATTGGTAGGA
AGGAGCCAGTGAACTTGGCTTTCCTGTTTCTATCTTTCATTAAAAAGAATAGAAGGATTCAGTCATAAAG
```

-continued

```
AGGTAAAAAACTGTCACGGTACGAAATCTTAGTGCCCACGGAGGCCTCGAGCAGAGAGAATGAAAGTCTT
TTTTTTTTTTTTTTTTTTTTAGCATGGCAATAAATATTCTAGCATCCCTAACTAAAGGGGACTAGACAGT
TAGAGACTCTGTCACCCTAGCTATACCAGCAGAAAACCTGTTCAGGCAGGCTTTCTGGGTGTGACTGATT
CCCAGCCTGTGGCAGGGCGTGGTCCCAACTACTCAGCCTAGCACAGGCTGGCAGTTGGTACTGAATTGTC
AGATGTGGAGTATTAGTGACACCACACATTTAATTCAGCTTTGTCCAAAGGAAAGCTTAAAACCCAATAC
AGTCTAGTTTCCTGGTTCCGTTTTAGAAAAGGAAAACGTGAACAAACTTAGAAAGGGAAGGAAATCCCAT
CAGTGAATCCTGAAACTGGTTTTAAGTGCTTTCCTTCTCCTCATGCCCAAGAGATCTGTGCCATAGAACA
AGATACCAGGCACTTAAAGCCTTTTCCTGAATTGGAAAGGAAAAGAGGCCCAAGTGCAAAAGAAAAAACA
TTTTAGAAACGGACAGCTTATAAAAATAAAGGGAAGAAAGGAGGCAGCATGGAGAGAGGCCTGTGCTAGA
AGCTCCATGGACGTGTCTGCACAGGGTCCTCAGCTCATCCATGCGGCCTGGGTGTCCTTTTACTCAGCTT
TATAACAAATGTGGCTCCAAGCTCAGGTGCCTTTGAGTTCTAGGAGGCTGTGGGTTTTATTCAACTACGG
TTGGGAGAATGAGACCTGGAGTCATGTTGAAGGTGCCCAACCTAAAAATGTAGGCTTTCATGTTGCAAAG
AACTCCAGAGTCAGTAGTTAGGTTTGGTTTGGTTTTGGACATGATAAACCTGCCAAGAGTCAACAGGTCA
CTTGATCATGCTGCAGTGGGTAGTTCTAAGGATGGAAAGGTGACAGTATTACTCTCGAGAGGCAATTCAG
TCCTGGGCAAAGGTATTAGTACAATAAGCGTTAAGGGCAGAGTCTACCTTGAAACCAATTAAGCAGCTTG
GTATTCATAAATATTGGGATTGGATGGCCTCCATCCAGAAATCACTATGGGTGAGCATACCTGTCTCAGC
TGTTTGGCCAATGTGCATAACCTACTCGGATCCCCACCTGACACTAACCAGAGTCAGCACAGGCCCCGAG
GAGCCCGAAGTCTGCTGCTGTGCAGCATGGAATTCCTTTAAAAAGGTGCACTACAGTTTTAGCGGGGAGG
GGGATAGGAAGACGCAGAGCAAATGAGCTCCGGAGTCCCTGCAGGTGAATAAACACACAGATCTGCATCT
GATAGAACTTTGATGGATTTTCAAAAAGCCGTTGACAAGGCTCTGCTATACAGTCTATAAAAATTGTTAT
TATGGGATTGGAAGAAACACGTGGTCATGAATAGAAAAAAAACAAACCCAAAGGTAGGAAGGTCAAGGTC
ATTTCTTAGATGGAGAAGTTGTGAAAGATGTCCTTGGAGATGAGTTTTAGGACCAGCATTACTAAGGCAG
GTGGGCAGACAGTGACCTCTCTAGGTGTGTCCACAGAGTTTTTCAGGAGAGAAAACTGCCTGACCTTTGG
GACTAAGCTGCGGAATCTTCTTACTAAGCTTGAAGAGTGGAGAGGCGAGAGGTGAGCTACTTTGTGAGCC
AAAGCTTATGTGACATGGTTGGGGAAACAGTCCAAACTGTTCTGAGAAGGTGAACTGTTACGACCCAGGA
CAATTAGAAAAATTCACCCACCATGCCGCACATTACTGGGTAAAAGCAGGGCAGCAGGGAACAAAACTCC
AGACTCTTGGGCCGTCCCCATTTGCAACAGCACACATAGTTTCTGGTATATTTGTTGGGAAAGATAAAAC
TCTAGCAGTTGTTGAGGGGAGGATGTATAAAATGGTCATGGGGATGAAAGGATCTCTGAGACCACAGAGG
CTCAGACTCACTGTTAAGAATAGAAAACTGGGTATGCGTTTCATGTAGCCAGCAGAACTGAAGTGTGCTG
TGACAAGCCAATGTGAATTTCTACCAAATAGTAGAGCATACCACTTGAAGAAGGAAAGAACCGAAGAGCA
AACAAAAGTTCTGCGTAATGAGACTCACCTTTTCTCGCTGAAAGCACTAAGAGGTGGGAGGAGGCCTGCA
CAGGCTGGAGGAGGGTTTGGGCAGAGCGAAGACCCGGCCAGGACCTTGGTGAGATGGGGTGCCGCCCACC
TCCTGCGGATACTCTTGGAGAGTTGTTCCCCCAGGGGGCTCTGCCCCACCTGGAGAAGGAAGCTGCCTGG
TGTGGAGTGACTCAAATCAGTATACCTATCTGCTGCACCTTCACTCTCCAGGGTACATGCTTTAAAACCG
ACCCGCAACAAGTATTGGAAAAATGTATCCAGTCTGAAGATGTTTGTGTATCTGTTTACATCCAGAGTTC
TGTGACACATGCCCCCAGATTGCTGCAAAGATCCCAAGGCATTGATTGCACTTGATTAAGCTTTTGTCT
GTAGGTGAAAGAACAAGTTTAGGTCGAGGACTGGCCCCTAGGCTGCTGCTGTGACCCTTGTCCCATGTGG
CTTGTTTGCCTGTCCGGGACTCTTCGATGTGCCCAGGGGAGCGTGTTCCTGTCTCTTCCATGCCGTCCTG
CAGTCCTTATCTGCTCGCCTGAGGGAAGAGTAGCTGTAGCTACAAGGGAAGCCTGCCTGGAAGAGCCGAG
CACCTGTGCCCATGGCTTCTGGTCATGAAACGAGTTAATGATGGCAGAGGAGCTTCCTCCCCACTTCGCA
```

-continued

```
GCGCCACATTATCCATCCTCTGAGATAAGTAGGCTGGTTTAACCATTGGAATGGACCTTTCAGTGGAAAC

CCTGAGAGTCTGAGAACCCCCAGACCAACCCTTCCCTCCCTTTCCCCACCTCTTACAGTGTTTGGACAGG

AGGGTATGGTGCTGCTCTGTGTAGCAAGTACTTTGGCTTATGAAAGAGGCAGCCACGCATTTTGCACTAG

GAAGAATCAGTAATCACTTTTCAGAAGACTTCTATGGACCACAAATATATTACGGAGGAACAGATTTTGC

TAAGACATAATCTAGTTTTATAACTCAATCATGAATGAACCATGTGTGGCAAACTTGCAGTTTAAAGGGG

TCCCATCAGTGAAAGAAACTGATTTTTTTTAACGGACTGCTTTTAGTTAAATTGAAGAAAGTCAGCTCTT

GTCAAAAGGTCTAAACTTTCCCGCCTCAATCCTAAAAGCATGTCAACAATCCACATCAGATGCCATAAAT

ATGAACTGCAGGATAAAATGGTACAATCTTAGTGAATGGGAATTGGAATCAAAAGAGTTTGCTGTCCTTC

TTAGAATGTTCTAAAATGTCAAGGCAGTTGCTTGTGTTTAACTGTGAACAAATAAAAATTTATTGTTTTG

CACTACAAAAAAAAAA.
```

USP47: NM_017944.3 Homo sapiens ubiquitin specific peptidase 47 (USP47),
transcript variant 2, mRNA. The sequence is as follows:

(SEQ ID NO: 9)

```
AGAGGGGAAAAGAACGTCAGGAGAGTGAACGGGAGCAAATAAAACGCTGTCCATTCTGACTGGAAGGGCC

AGAGCCGTGTCTAAGGGCGGGGGCCGGGAGGTGGCCCGCGGTGGTGTCTCTACCAGGACGAGGCCTGGGG

TATCTGAAGAGGGGATGACGTCCAGGCGCTTTGCTAAAGGGAAGCCAGAAGGGTATGAGTTGCTAGGGTC

AGAGATGGGGCTTTCGGCTCGAGTCTTTCCCTGCAGGGCAGAGAGTCCGAAGAGCCCGAGAAGGCAGGGA

GGACAGTGGGCCTGGTCCTTCCCCGGCCGGCAGAGGGAGTCCCGAGATGGAACGTCCAGCTCTCCTCTAA

CGAAAAGCGTTTGCATGGCTGTCTCGCCAATTCTGTACCTCCCGGGGCTGAGGAAGAGCCGAGGTGACTA

GAAGCTAGCGACAAGTGCCGGCCACCTCCGACGCCAGGCGCCGGGCTTGGAGCCCGACGGGCCGAATTCT

CGCGAGAGCGGCCGCCGCCATTTTTCCATTGATTGCAGCGGGCTGGGGGAGGGGCCGACGACGAAGGCGG

CTGTGGTAGCGGCGGCGGCGGCGGAGCCCTGGGTCGGTGTCTGCGCGCTGGTGTCTGAGGCCCAGGC

TGAGGCCTCCGCTATTGCTGGAGCGCAGGCGGCGGAGAGGATGACTGCCGCTGCCATTCTCTCTTGAGCT

AGCGAGCCGCCGCCACCCTCCACCCTCCCCCGGCAGGGCGGAGAGGAGCGGCCGGAGTCAGCGATGGTGC

CCGGCGAGGAGAACCAACTGGTCCCGAAAGAGGCACCACTGGATCATACCAGTGACAAGTCACTTCTCGA

CGCTAATTTTGAGCCAGGAAAGAAGAACTTTCTGCATTTGACAGATAAAGATGGTGAACAACCTCAAATA

CTGCTGGAGGATTCCAGTGCTGGGGAAGACAGTGTTCATGACAGGTTTATAGGTCCGCTTCCAAGAGAAG

GTTCTGGGGGTTCTACCAGTGATTATGTCAGCCAAAGCTACTCCTACTCATCTATTTTGAATAAATCAGA

AACTGGATATGTGGGACTAGTAAACCAAGCAATGACTTGCTATTTGAATAGCCTTTTGCAAACACTTTTT

ATGACTCCTGAATTTAGGAATGCATTATATAAGTGGGAATTTGAAGAATCTGAAGAAGATCCAGTGACAA

GTATTCCATACCAACTTCAAAGGCTTTTTGTTTTGTTACAAACCAGCAAAAAGAGAGCAATTGAAACCAC

AGATGTTACAAGGAGCTTTGGATGGGATAGTAGTGAGGCTTGGCAGCAGCATGATGTACAAGAACTATGC

AGAGTCATGTTTGATGCTTTGGAACAGAAATGGAAGCAAACAGAACAGGCTGATCTTATAAATGAGCTAT

ATCAAGGCAAGCTGAAGGACTACGTGAGATGTCTGGAATGTGGTTATGAGGGCTGGCGAATCGACACATA

TCTTGATATTCCATTGGTCATCCGACCTTATGGGTCCAGCCAAGCATTTGCTAGTGTGGAAGAAGCATTG

CATGCATTTATTCAGCCAGAGATTCTGGATGGCCCAAATCAGTATTTTGTGAACGTTGTAAGAAGAAGT

GTGATGCACGGAAGGGCCTTCGGTTTTTGCATTTTCCTTATCTGCTGACCTTACAGCTGAAAAGATTCGA

TTTTGATTATACAACCATGCATAGGATTAAACTGAATGATCGAATGACATTTCCCGAGGAACTAGATATG

AGTACTTTATTGATGTTGAAGATGAGAAATCTCCTCAGACTGAAAGTTGCACTGACAGTGGAGCAGAAA

ATGAAGGTAGTTGTCACAGTGATCAGATGAGCAACGATTTCTCCAATGATGATGGTGTTGATGAAGGAAT

CTGTCTTGAAACCAATAGTGGAACTGAAAAGATCTCAAAATCTGGACTTGAAAAGAATTCCTTGATCTAT

GAACTTTTCTCTGTTATGGTTCATTCTGGGAGCGCTGCTGGTGGTCATTATTATGCATGTATAAAGTCAT
```

-continued

```
TCAGTGATGAGCAGTGGTACAGCTTCAATGATCAACATGTCAGCAGGATAACACAAGAGGACATTAAGAA
AACACATGGTGGATCTTCAGGAAGCAGAGGATATTATTCTAGTGCTTTCGCAAGTTCCACAAATGCATAT
ATGCTGATCTATAGACTGAAGGATCCAGCCAGAAATGCAAAATTTCTAGAAGTGGATGAATACCCAGAAC
ATATTAAAAACTTGGTGCAGAAAGAGAGAGAGTTGGAAGAACAAGAAAAGAGACAACGAGAAATTGAGCG
CAATACATGCAAGATAAAATTATTCTGTTTGCATCCTACAAAACAAGTAATGATGGAAAATAAATTGGAG
GTTCATAAGGATAAGACATTAAAGGAAGCAGTAGAAATGGCTTATAAGATGATGGATTTAGAAGAGGTAA
TACCCCTGGATTGCTGTCGCCTTGTTAAATATGATGAGTTTCATGATTATCTAGAACGGTCATATGAAGG
AGAAGAAGATACACCAATGGGGCTTCTACTAGGTGGCGTCAAGTCAACATATATGTTTGATCTGCTGTTG
GAGACGAGAAAGCCTGATCAGGTTTTCCAATCTTATAAACCTGGAGAAGTGATGGTGAAAGTTCATGTTG
TTGATCTAAAGGCAGAATCTGTAGCTGCTCCTATAACTGTTCGTGCTTACTTAAATCAGACAGTTACAGA
ATTCAAACAACTGATTTCAAAGGCCATCCATTTACCTGCTGAAACAATGAGAATAGTGCTGGAACGCTGC
TACAATGATTTGCGTCTTCTCAGTGTCTCCAGTAAAACCCTGAAAGCTGAAGGATTTTTTAGAAGTAACA
AGGTGTTTGTTGAAAGCTCCGAGACTTTGGATTACCAGATGGCCTTTGCAGACTCTCATTTATGGAAACT
CCTGGATCGGCATGCAAATACAATCAGATTATTTGTTTTGCTACCTGAACAATCCCCAGTATCTTATTCC
AAAAGGACAGCATACCAGAAAGCTGGAGGCGATTCTGGTAATGTGGATGATGACTGTGAAAGAGTCAAAG
GACCTGTAGGAAGCCTAAAGTCTGTGGAAGCTATTCTAGAAGAAAGCACTGAAAAACTCAAAAGCTTGTC
ACTGCAGCAACAGCAGGATGGAGATAATGGGGACAGCAGCAAAAGTACTGAGACAAGTGACTTTGAAAAC
ATCGAATCACCTCTCAATGAGAGGGACTCTTCAGCATCAGTGGATAATAGAGAACTTGAACAGCATATTC
AGACTTCTGATCCAGAAAATTTTCAGTCTGAAGAACGATCAGACTCAGATGTGAATAATGACAGGAGTAC
AAGTTCAGTGGACAGTGATATTCTTAGCTCCAGTCATAGCAGTGATACTTTGTGCAATGCAGACAATGCT
CAGATCCCTTTGGCTAATGGACTTGACTCTCACAGTATCACAAGTAGTAGAAGAACGAAAGCAAATGAAG
GGAAAAAAGAAACATGGGATACAGCAGAAGAAGACTCTGGAACTGATAGTGAATATGATGAGAGTGGCAA
GAGTAGGGGAGAAATGCAGTACATGTATTTCAAAGCTGAACCTTATGCTGCAGATGAAGGTTCTGGGGAA
GGACATAAATGGTTGATGGTGCATGTTGATAAAAGAATTACTCTGGCAGCTTTCAAACAACATTTAGAGC
CCTTTGTTGGAGTTTTGTCCTCTCACTTCAAGGTCTTTCGAGTGTATGCCAGCAATCAAGAGTTTGAGAG
CGTCCGGCTGAATGAGACACTTTCATCATTTTCTGATGACAATAAGATTACAATTAGACTGGGGAGAGCA
CTTAAAAAAGGAGAATACAGAGTTAAAGTATACCAGCTTTTGGTCAATGAACAAGAGCCATGCAAGTTTC
TGCTAGATGCTGTGTTTGCTAAAGGAATGACTGTACGGCAATCAAAAGAGGAATTAATTCCTCAGCTCAG
GGAGCAATGTGGTTTAGAGCTCAGTATTGACAGGTTTCGTCAAGGAAAAAAACATGGAAGAATCCTGGC
ACTGTCTTTTTGGATTATCATATTTATGAAGAAGATATTAATATTTCCAGCAACTGGGAGGTTTTCCTTG
AAGTTCTTGATGGGGTAGAGAAGATGAAGTCCATGTCACAGCTTGCAGTTTTGTCAAGACGGTGGAAGCC
TTCAGAGATGAAGTTGGATCCCTTCCAGGAGGTTGTATTGGAAAGCAGTAGTGTGGACGAATTGCGAGAG
AAGCTTAGTGAAATCAGTGGGATTCCTTTGGATGATATTGAATTTGCTAAGGGTAGAGGAACATTTCCCT
GTGATATTTCTGTCCTTGATATTCATCAGGATTTAGACTGGAATCCTAAAGTTTCTACCCTGAATGTCTG
GCCTCTTTATATCTGTGATGATGGTGCGGTCATATTTTATAGGGATAAAACAGAAGAATTAATGGAATTG
ACAGATGAGCAAAGAAATGAACTGATGAAAAAAGAAAGCAGTCGACTCCAGAAGACTGGACATCGTGTAA
CATACTCACCTCGTAAAGAGAAAGCACTAAAAATATATCTGGATGGAGCACCAAATAAAGATCTGACTCA
AGACTGACTCTGATAGTGTAGCATTTTCCCTGGGGGAGTTTTGGTTTTAATTAGATGGTTCACTACCACT
GGGTAGTGCCATTTTGGCCGGACATGGTTGGGGTAACCCAGTGACACCAGCACTGATTGGACTGCCCTAC
ACCAATCAGAAGCTCAGTGCCCAATGGGCCACTGTTTTGACTCGGAATCATGTTGTGCACTATAGTCAAA
TGTACTGTAAAGTGAAAAGGGATGTGCAAAAAAATAAAAAAAAACAACAAAAAAAGCTAACCTTCTATTA
```

```
GAAAAGGGGACAGGGGAATGAGTAAACTTCTTTTATTGCGGACAAATGTGCACATAGCCGCTAGTAAAAC

TAGCCTCAAACAGGATGCTCATAGCTTAATAATAAAAGCTGTGCAAAGGCCATGAATGAATGAATTTTCT

GTTTATTTCACTGATGCACACATTACCTCATTGACAATTCAGAAGTAAATCCAACGTGTGTTGACTCTTG

GAAAGCAGCAAAAACAGGAGCTGAAGAAAAGAAATTCTTGGAACCAGCCGTAACCCAGTAAGGAATTGTG

AAGTTGTGTTTTATTTTGTTTCATTTTTTGCAGAGTATTAAGAACATTATTCTGGAACATCAGAACGTT

TCCCTTAGACCGATCCCAGCAGGTGGCAGCTCAGATTGCTGCAGTGTTGTAATTATAACTGATTGTACTT

AAGTTATGGATGTAGAGAATATGTTTCATTCATTTATTCAGCATGTAAATAAAATTGATCCTGTTGAGTT

ATCATAATTGCAGTTCAACTATCTGCCATGATTATTCTTTTCACGTATCATTCATTCTGTACATTTGTGT

ACATTGAGAAGTATAGCAATCTATGTAAATGTAATCCTCAGTGAGGTTCCTCAGTGCTAGGTCCCATAGG

ATTGTCGTTGCCCTTGTTAATGAGGTTTCTCTGTTCAGCGGCTTCAATTTTTTTCTCTTTGTACATCTAG

TTTTGAAGATTTACTTCAAGTTTGAATCTTCTAGAATGCTTGTAAGTCCAGTTTTAATTTTTAGAGTCAA

TTTGTAGTTACATGTAGTTTAACTTTTGGGAAACGTCTTAACATTGTTCTGAATAAACTTGCTAATGAGG

TCAGGTCATGGTACAGACTGATGCAGTCAACATGATTTCATTGCAGAGTTTATTAGTATCAGCAAGTTTT

TGCTTTGCTAAATAAAAGTACTCAATGAACACAATTCTACATAAATTTTGACATACCATCTAATTTATAA

AAATCAATAAAAAAGGTTTTGGTAAAACTTTTTCATGCCAGATGCTGTTTACAACAATGAACATGCCAAT

AAAACATTTGTTCATTCTGTTGTGTTATTTTAGTCATTAAACTTCTGTGGATGAAGAATCTGGGTTAAGA

ATAGATTTGTCATCTTTAAATATGACATTTTGTAATGTGTATTGGATATCTCATTTCTATGATAAAGGTA

TATTTACAGTAAAGTTCTCATAAGAGAAATGAAAAGCTGTGTTAATATCTAACTTTGGGGAACCCTGTCA

GTATTTCAGATCCGATTTTTACCCTTTTTTTCTTATAAGAAAGATAAAATTAGAAAATACTGTTAGCAAA

TGTGGCTCTGCCATTTGAATATAATCACCGAGAATTCCATGTCTTAAAAGTCTCCTGGAATCCACAATGA

AAAAAAAAATCTTTTCTAAGGTATTTTTCTGGCTAATTTTTATTTGAAGAAAGCTATAGCATTTAGCGAA

ATTTGACTGAAGTAATGTTCTGAGTTTGCATTAGTGGGATTGGTGATGTTCTCAGAAGAAAATTGGAAAC

ACTTGTGATGAATTGTCTTTCAGATCACTTAGATTTTCTGATGTAAGAGGACAGCTGTTTGGTTCTGATA

CAGGCCTGCTTACTTGGGATGTAGGGTTAGTAAATGGGGTTTCTGCTTTAAAGGACTGACTTGCTATCAC

ACAAAAGAGGCAGACTTGTAAACACAATGGGCTTTGGAGTTTGGTCTGATTGGGTTTGGTTTAGTATTCC

TATGAGCGTAAATGGTAAAATTCTTCTGATACCCACTCTTTAGACTGTGCCTTCTGCTCTGTTCTTTGTT

TTATGTTTAACTGCTGTTTCTAATTGCAGGTGTATTACAGATACAAATAAGAGTAAAGAAAATATATTTC

ATTATAGAAAAGAAAAAATTAAAAGCTTCTTGCTTTTCAGTGCCTGATAGAGTGAAAACACAAAGTTGCA

CTTTAATAATTTCAATAAAAGCTAATCTGTGTCAGCCTCCCTCTGCTTCAGAGAGTCAGGTGAGCATCCA

TAACCTAACAGGCAGAGCCCTAGCGATGTGGATCAAGTTTCCTGAGCCCGGGGCGGTGGAGCCTCATGA

TCTCTTATCTTTTGAGGCTGAGGCAGGTCACATGCAACAAATTGTGACCCTGCTCCCCACAAGTCATGCA

AAGGTTTTGAAGAGCTTTTACCGTGGGGCAGATGAACTTGTGTCAACCATGCACACCCTGTGAGAACCAA

GTACCTGTGTTTCTAAGGCGGGCACTCAAGGTGAGGGGTGCATTCTGGCCAAAGAAACAAAAGCTGTGGT

TTCAGGACCATGCCGTGTGTAGCTGATCTGTACGGGACGTGTATGTAAGGAAGAGCAATCATGATAGATA

AGAACAGTGTGTGAAGCAGCCTTCACACTAGAGTGTTTGGTCATCTCTTATAATGTAAGGGAAGGTACTT

TAAAATTCTGGGAAGATGCGATGAACTCATGTCCCAGTCAGAAAATAATCCAATGAAATAAGCATTGGTT

GCCAGGCCACAGTTAGGAATTGTATTGTGATACATCTAGAGGCCAAGAGAGCAGGAGAGAGCTACCAACT

TACACTGTGGTTTAAGCTAAATGACCGCACAGCATCATAGCATTGCAGTGTTGTTACTAAATCTGGAAGT

GACCTGTGAATGTATGGAATACAATAAAGTCTTTTATTCTGGTTCATTTGCTAGTACTTCCTTTTTGATT

GGATACTGTAGTTCTTCCTCTGGATTTTATTTTGTTCAGCGTCAAGGCCCTAATTTTGCAAATGTAGTCT
```

-continued

AAACCACATTACGTGGACTAGAGGATACTCTGAATTAGCAAGTTTTTTGTTTGCTGAATAAAACTATTCC

ATCTTAA.

ZBTB16: NM_006006.4 *Homo sapiens* zinc finger and BTB domain containing 16 (ZBTB16), transcript variant 1, mRNA. The sequence is as follows:

(SEQ ID NO: 10)

GCAGCAGAGAGGAGTTGAGGGCGATGAGAGCGGGTACTGCGAACTGCCGGGCGATGCTGTCGCTGCCGCC

GTGATACGGAGAGCAACAGTTCCCCAGCAACACCCCTCCCCGACACAGGCACACACCCCCCGACAGGCAC

GCACACCCACCCCACAGTGCCCGGCTCGGCTGCGCCTCCTCTATTGGCCCAGGAAGCCCACCCAGCCCCG

CCACGCAGAGCCCAGAAGGAAAGAAAGCCTCATGCCTGAGCCGAGGGGAGCACCATGGATCTGACAAAAA

TGGGCATGATCCAGCTGCAGAACCCTAGCCACCCCACGGGGCTACTGTGCAAGGCCAACCAGATGCGGCT

GGCCGGGACTTTGTGCGATGTGGTCATCATGGTGGACAGCCAGGAGTTCCACGCCCACCGGACGGTGCTG

GCCTGCACCAGCAAGATGTTTGAGATCCTCTTCCACCGCAATAGTCAACACTATACTTTGGACTTCCTCT

CGCCAAAGACCTTCCAGCAGATTCTGGAGTATGCATATACAGCCACGCTGCAAGCCAAGGCGGAGGACCT

GGATGACCTGCTGTATGCGGCCGAGATCCTGGAGATCGAGTACCTGGAGGAACAGTGCCTGAAGATGCTG

GAGACCATCCAGGCCTCAGACGACAATGACACGGAGGCCACCATGGCCGATGGCGGGGCCGAGGAAGAAG

AGGACCGCAAGGCTCGGTACCTCAAGAACATCTTCATCTCGAAGCATTCCAGCGAGGAGAGTGGGTATGC

CAGTGTGGCTGGACAGAGCCTCCCTGGGCCCATGGTGGACCAGAGCCCTTCAGTCTCCACTTCATTTGGT

CTTTCAGCCATGAGTCCCACCAAGGCTGCAGTGGACAGTTTGATGACCATAGGACAGTCTCTCCTGCAGG

GAACTCTTCAGCCACCTGCAGGGCCCGAGGAGCCAACTCTGGCTGGGGTGGGCGGCACCCTGGGGTGGC

TGAGGTGAAGACGGAGATGATGCAGGTGGATGAGGTGCCCAGCCAGGACAGCCCTGGGGCAGCCGAGTCC

AGCATCTCAGGAGGGATGGGGGACAAGGTTGAGGAAAGAGGCAAAGAGGGGCCTGGGACCCCGACTCGAA

GCAGCGTCATCACCAGTGCTAGGGAGCTACACTATGGGCGAGAGGAGAGTGCCGAGCAGGTGCCACCCCC

AGCTGAGGCTGGCCAGGCCCCCACTGGCCGACCTGAGCACCCAGCACCCCCGCCTGAGAAGCATCTGGGC

ATCTACTCCGTGTTGCCCAACCACAAGGCTGACGCTGTATTGAGCATGCCGTCTTCCGTGACCTCTGGCC

TCCACGTGCAGCCTGCCCTGGCTGTCTCCATGGACTTCAGCACCTATGGGGGCTGCTGCCCCAGGGCTT

CATCCAGAGGGAGCTGTTCAGCAAGCTGGGGGAGCTGGCTGTGGGCATGAAGTCAGAGAGCCGGACCATC

GGAGAGCAGTGCAGCGTGTGTGGGGTCGAGCTTCCTGATAACGAGGCTGTGGAGCAGCACAGGAAGCTGC

ACAGTGGGATGAAGACGTACGGGTGCGAGCTCTGCGGGAAGCGGTTCCTGGATAGTTTGCGGCTGAGAAT

GCACTTACTGGCTCATTCAGCGGGTGCCAAAGCCTTTGTCTGTGATCAGTGCGGTGCACAGTTTTCGAAG

GAGGATGCCCTGGAGACACACAGGCAGACCCATACTGGCACTGACATGGCCGTCTTCTGTCTGCTGTGTG

GGAAGCGCTTCCAGGCGCAGAGCGCACTGCAGCAGCACATGGAGGTCCACGCGGGCGTGCGCAGCTACAT

CTGCAGTGAGTGCAACCGCACCTTCCCCAGCCACACGGCTCTCAAACGCCACCTGCGCTCACATACAGGC

GACCACCCCTACGAGTGTGAGTTCTGTGGCAGCTGCTTCCGGGATGAGAGCACACTCAAGAGCCACAAAC

GCATCCACACGGGTGAGAAACCCTACGAGTGCAATGGCTGTGGCAAGAAGTTCAGCCTCAAGCATCAGCT

GGGAGACGCACTATAGGGTGCACACAGGTGAGAAGCCCTTTGAGTGTAAGCTCTGCCACCAGCGCTCCCGG

GACTACTCGGCCATGATCAAGCACCTGAGAACGCACAACGGCGCCTCGCCCTACCAGTGCACCATCTGCA

CAGAGTACTGCCCCAGCCTCTCCTCCATGCAGAAGCACATGAAGGGCCACAAGCCCGAGGAGATCCCGCC

CGACTGGAGGATAGAGAAGACGTACCTCTACCTGTGCTATGTGTGAAGGGAGGCCCGCGGCGGTGGAGCC

GAGCGGGGAGCCAGGAAAGAAGAGTTGGAGTGAGATGAAGGAAGGACTATGACAAATAAAAAAGGAAAAG

AAAAAAAAAAACAGAAGGAAAAGGAAAAAAAAAAAAA.

PLPP1: NM_003711.3 *Homo sapiens* phospholipid phosphatase 1 (PLPP1), transcript variant 1, mRNA. The sequence is as follows:

(SEQ ID NO: 11)

CGCGAACCCGCGCGCTGCCCGGTCCTGCGCTGCTCAGCGGGAGGGGCTGGACCCCGCGTTCCTCCTCCCT

```
GCCGGTCCCCATCCTTAAAGCGAGAGTCTGGACGCCCCGCCTGTGGGAGAGAGCGCCGGGATCCGGACGG

GGAGCAACCGGGGCAGGCCGTGCCGGCTGAGGAGGTCCTGAGGCTACAGAGCTGCCGCGGCTGGCACACG

AGCGCCTCGGCACTAACCGAGTGTTCGCGGGGGCTGTGAGGGGAGGGCCCCGGGCGCCATTGCTGGCGGT

GGGAGCGCCGCCCGGTCTCAGCCCGCCCTCGGCTGCTCTCCTCCTCCGGCTGGGAGGGGCCGTAGCTCGG

GGCCGTCGCCAGCCCCGGCCCGGGCTCGAGAATCAAGGGCCTCGGCCGCCGTCCCGCAGCTCAGTCCATC

GCCCTTGCCGGGCAGCCCGGGCAGAGACCATGTTTGACAAGACGCGGCTGCCGTACGTGGCCCTCGATGT

GCTCTGCGTGTTGCTGGCTGGATTGCCTTTTGCAATTCTTACTTCAAGGCATACCCCCTTCCAACGAGGA

GTATTCTGTAATGATGAGTCCATCAAGTACCCTTACAAAGAAGACACCATACCTTATGCGTTATTAGGTG

GAATAATCATTCCATTCAGTATTATCGTTATTATTCTTGGAGAAACCCTGTCTGTTTACTGTAACCTTTT

GCACTCAAATTCCTTTATCAGGAATAACTACATAGCCACTATTTACAAAGCCATTGGAACCTTTTTATTT

GGTGCAGCTGCTAGTCAGTCCCTGACTGACATTGCCAAGTATTCAATAGGCAGACTGCGGCCTCACTTCT

TGGATGTTTGTGATCCAGATTGGTCAAAAATCAACTGCAGCGATGGTTACATTGAATACTACATATGTCG

AGGGAATGCAGAAAGAGTTAAGGAAGGCAGGTTGTCCTTCTATTCAGGCCACTCTTCGTTTTCCATGTAC

TGCATGCTGTTTGTGGCACTTTATCTTCAAGCCAGGATGAAGGGAGACTGGGCAAGACTCTTACGCCCCA

CACTGCAATTTGGTCTTGTTGCCGTATCCATTTATGTGGGCCTTTCTCGAGTTTCTGATTATAAACACCA

CTGGAGCGATGTGTTGACTGGACTCATTCAGGAGCTCTGGTTGCAATATTAGTTGCTGTATATGTATCG

GATTTCTTCAAAGAAAGAACTTCTTTTAAAGAAAGAAAGAGGAGGACTCTCATACAACTCTGCATGAAA

CACCAACAACTGGGAATCACTATCCGAGCAATCACCAGCCTTGAAAGGCAGCAGGGTGCCCAGGTGAAGC

TGGCCTGTTTTCTAAAGGAAAATGATTGCCACAAGGCAAGAGGATGCATCTTTCTTCCTGGTGTACAAGC

CTTTAAAGACTTCTGCTGCTGCTATGCCTCTTGGATGCACACTTTGTGTGTACATAGTTACCTTTAACTC

AGTGGTTATCTAATAGCTCTAAACTCATTAAAAAAAACTCCAAGCCTTCCACCAAAACAGTGCCCCACCTG

TATACATTTTTATTAAAAAAATGTAATGCTTATGTATAAACATGTATGTAATATGCTTTCTATGAATGAT

GTTTGATTTAAATATAATACATATTAAAATGTATGGGAGAACCAAATCCACACTTGCAAAAAAAAAAAAA

AAAAA.

PLEKHH2: NM_172069.3 Homo sapiens pleckstrin homology, MyTH4 and FERM
domain containing H2 (PLEKHH2), mRNA. The sequence is as follows:
                                                           (SEQ ID NO: 12)
GAGAGTCCGGGGATCCCGGGGCCAGTCGCGGCCGGGACATCGGGCGCTGCGGCCGGGGACCCGCTGCTG

AGATAGACAGAATATGGCAGAGCTTTCTGAGCCAGAGGGACCAGTAGATTGGAAGGAACGATGTGTAGCT

CTGGAGTCCCAACTCATGAAATTTAGAGTTCAAGCAAGCAAGATACGAGAGCTTTTAGCAGAGAAGATGC

AACAGCTTGAGAGACAAGTTATTGATGCTGAACGTCAAGCAGAAAAAGCTTTTCAACAGGTACAAGTTAT

GGAAGATAAATTAAAAGCAGCTAATATTCAAACCAGTGAATCAGAGACAAGATTATATAATAAGTGTCAA

GATCTGGAGTCGCTAATACAGGAAAAAGATGACGTCATTCAAAACTTGGAATTGCAACTTGAAGAGCAGA

AACAAATAAGAATACAAGAAGCTAAAATAATAGAAGAGAAAGCAGCTAAGATAAAAGAATGGGTAACAGT

TAAGTTAAATGAGCTGGAATTGGAGAATCAGAATCTTCGTTTGATCAACCAAAACCAAACTGAAGAGATA

AGAACAATGCAGTCAAAACTACAAGAAGTTCAAGGAAAGAAGTCATCCACTGTCTCTACACTAAAGCTTT

CGGAAGGCCAGCGCCTGAGCAGTTTGACCTTTGGGTGCTTTTTATCTCGAGCAAGGAGTCCTCCTCAAGT

AGTAAAATCTGAGGAAATGAGCAAGATATCATCGAAAGAACCTGAGTTCACTGAAGGAAAAGACATGGAA

GAAATGGAAATTCCAGAAAAGTCTGTTGATAACCAAGTTCTAGAAAACAACAGAGGCCAGAGAACATTGC

ATCAAACCCCTTGTGGCTCAGAACAGAATCGGAAAACAAGAACAAGCTTTGCCACAGATGGTGGCATCTC

CCAGAATTCTGGGGCTCCTGTGAGTGACTGGAGCTCTGATGAGGAAGACGGGAGCAAAGGAAGATCCAAG

TCCAGATGCACATCCACCCTCTCCAGTCACACATCTGAGGAAGGGGTCCAGTGTAGCAGGATGGGAAGTG
```

-continued

AAATGTATCTGACAGCATCTGATGACAGCAGCTCTATATTTGAGGAAGAGACTTTTGGCATAAAGAGACC

AGAACACAAGAAGCTATATTCTTGGCAGCAGGAGGCACAGTGGAAAGCTCTAAATAGTCCTCTTGGAAAG

GGAAATTCTGAATTAAGTAAAAAGGAACAAGATAGTTCCTCGGATGAACTGAATAAAAAATTTCAATCCC

AGAGACTCGATTATTCATCTTCATCGAGTGAAGCCAACACCCCAAGCCCTATTTTGACCCCAGCTTTAAT

GCCAAAGCATCCTAACTCACTCTCTGGAAAAGGAACACAATTAGTGCCTTCATCACACCTGCCACCCCCA

AAGTTAAGGATTCCTAATGTTTTCAGTATAAGTGTAGCACTAGCCAAAAGGCACTTAAGCCAGCCACAGT

TAAGCTCTGACAGGATGTTTGGTACAAATAGAAACGCTATAAGCATGATACGACCACTGAGACCTCAGGA

AACTGATCTTGATCTAGTTGATGGAGACAGTACAGAAGTTTTAGAGAATATGGACACGAGTTGTGATGAT

GGATTATTTTCCTATGACTCCTTGGACTCTCCAAATTCAGATGACCAGGAACACTGTGACTCAGCAAAGA

AGGTGGCATACAGCAAACCTCCAACTCCTCCCCTGCACCGTTTTCCTTCTTGGGAAAGCAGAATTTATGC

TGTAGCCAAATCAGGTATTCGAATGTCTGAGGCCTTCAATATGGAGAGTGTTAATAAAAATTCTGCTGCA

ACCCTTTCCTATACTACATCAGGACTTTATACATCTCTGATATACAAGAACATGACCACCCCAGTGTATA

CAACTTTGAAGGGGAAGGCGACCCAAATAAGTAGCAGCCCTTTCCTGGATGACTCATCTGGGTCAGAGGA

AGAAGACAGCTCCAGATCCAGCTCCCGGACGTCAGAGTCAGACTCACGCAGTAGGAGTGGGCCAGGCAGC

CCCAGAGCCATGAAACGAGGTGTGTCTCTCTCCTCTGTGGCTTCTGAAAGTGATTATGCTATTCCTCCTG

ATGCTTACTCCACAGACACGGAGTACTCACAGCCAGAGCAGAAGCTCCCAAAAACTTGCTCATCTTCCAG

TGATAATGGGAAAAATGAACCACTGGAAAAATCTGGTTATTTATTAAAAATGAGTGGTAAAGTCAAGTCT

TGGAAGCGGCGGTGGTTTGTTCTTAAAGGTGGTGAATTACTTTACTACAAATCTCCGAGTGATGTAATTA

GAAAACCCCAGGGCCATATTGAACTTAGTGCATCCTGTAGTATTTTAAGAGGAGATAACAAACAAACAGT

TCAGTTGACCACTGAAAAACACACATACTATCTGACTGCAGATTCTCCCAATATATTGGAAGAGTGGATT

AAAGTGTTACAGAATGTTCTTCGAGTACAAGCTGCCAACCCACTTTCCCTGCAGCCTGAGGGCAAACCCA

CCATGAAGGGATTGCTCACTAAGGTAAAACATGGATATTCCAAGAGAGTCTGGTGTACACTAATAGGAAA

GACATTATATTATTTTCGGAGTCAAGAAGATAAGTTTCCTTTAGGTCAGATCAAACTCTGGGAGGCTAAA

GTGGAAGAGGTTGACAGATCTTGTGATTCAGATGAAGATTATGAAGCCAGTGGACGAAGTCTGTTATCCA

CACATTATACTATCGTTATCCATCCCAAAGACCAAGGTCCAACTTACCTCCTAATTGGATCCAAGCATGA

AAAGGACACTTGGCTTTATCATCTGACTGTTGCAGCTGGAAGCAACAATGTAAACGTTGGATCTGAATTT

GAACAACTGGTTTGCAAATTGCTAAATATAGACGGGGAGCCTTCCTCTCAGATATGGAGACACCCCACTT

TGTGTCACAGTAAAGAAGGAATCATTTCCCCTCTGACAACTCTACCTTCCGAAGCCCTGCAGACAGAAGC

TATTAAATTATTTAAGACCTGCCAGCTTTTTATAAATGCTGCAGTTGACTCTCCTGCAATTGATTACCAC

ATATCTTTAGCCCAGAGTGCTTTGCAAATCTGCCTGACACATCCTGAGCTGCAGAATGAAATTTGCTGTC

AGCTTATTAAACAGACAAGACGAAGACAGCCACAGAATCAACCAGGACCATTGCAGGGCTGGCAGCTCTT

GGCACTCTGCGTTGGGCTCTTCCTTCCCCATCATCCTTTCCTGTGGCTCCTCAGGCTTCACCTAAAGAGG

AATGCAGATTCCAGGACAGAATTTGGAAAATATGCCATTTACTGCCAGCGTTGTGTAGAAAGAACGCAAC

AAAATGGTGACAGAGAAGCAAGACCCTCAAGGATGGAAATTCTTTCAACTCTTCTCCGAAACCCTTATCA

CCATTCTTTGCCCTTTAGTATACCTGTGCACTTCATGAATGGGATATACCAGGTAGTTGGTTTTGACGCA

TCTACCACAGTGGAAGAATTTTTGAATACTTTGAACCAGGACACAGGAATGAGGAAACCAGCGCAGTCTG

GATTTGCGTTGTTCACTGACGATCCTTCTGGCAGAGATTTAGAGCATTGTCTTCAAGGAAACATCAAGAT

TTGTGACATTATTTCCAAATGGGAACAGGCTTCCAAAGAACAGCAGCCTGGAAAATGTGAAGGTACAAGG

ACTGTTCGTCTGACATACAAAAACAGACTATATTTCTCAGTGCAAGCTCGTGGAGAGACTGATAGAGAAA

AGTTGCTGTTAATGTATCAGACAAATGATCAAATCATAAATGGACTTTTTCCTCTGAACAAAGATCTGGC

-continued

```
ATTAGAAATGGCAGCTCTTTTATCTCAGGTAGAGATTGGAGATTTTGAAAGACCTTTCTCAACTCCAGCA
GGGCATGTTACCAATCAGTGCAAAGTGAATCAAACTCTAAAGCAAGTCATAGAGAAATTTTATCCTAAAA
GGTATAGAGATGGCTGTTCTGAAGAGCAGTTAAGGCAGCTTTGCCAGCGACTTTCAACCAGATGGATGGC
CCTCCGGGGACACAGTGCTGCTGACTGTGTGCGCATTTATTTGACAGTAGCCAGGAAGTGGCCATTCTTT
GGTGCCAAGTTGTTTCTTGCAAAACCCATAACTCCATCATCACTTGGAAGTACTTTCTTGTGGCTGGCTG
TACATGAGGATGGTTTAAGCCTCTTAGAATACAACTCCATGAGGTTAATAGTCAGCTATGTGTACAAGAG
TCTAATGACCTTTGGAGGCTATCAAGATGATTTTATGGTAGTCATTAACAATACACATTCAAAGGACAAA
CCAACGAGAAATTACTTTTTGCCATGGCAAAACCCAAGATTCTTGAAATCACTCTTTTGATCGCCAGTT
ACATAAACAACTTCCATCAGCAAAAGGCAGCATTTCACCACCTCTCTGCTCCAGCACTGCTCTCAGCCCA
GACCCGGGGACCCCAAGCCAGAATGATGGGAAGCCAGCCTCTTCTGTCAAGCAGCAGACCGACCAAAGGC
CCCACCTTACTCTGAAAGCTGGGGAGCCTGAACATTCACTCCTTGTCCTCCATGCTGTGGCTGTATCAGC
TCCCTACAAGTTCGTTTACACCTGGCAGCACGGCAGCCACACACCGGTATTCCAAACCTTAACAATGAAG
GGGGTTAGTCTCTTTTATTTGATTCTTAAATATTCAAATAAATATTAACAGTAAAACATAAACACAAAAT
TTGCCAACACACTAATTTTCTTATAGAGTAAATGAGTAAGAATTCATCATTTTTTCCATCTCCCTTCTCC
CTTGTCATCAGACACATTGTGCAATGTGGCTTTTCTTTTCTTTTCTTTTTTTCCCCTTTTTAATATTCTG
GCAATCTTTAGAAAGGGAGATTCCAAACTCCCATTTGGTAAACCAGTTGATTATTTGGAAATGTTCACTG
CCAAAATAGTAAGTGCTATAACTAAATGCGCTTTTAATTAATGATATAGTGTTTGGAAAGGAGTAGAACA
TGCAGCATAAGAAACTGCTGCAGAGTGGTGCGAGGAGTACATTTTCAGAGCAGGTGCAGTACATCTTCCG
GCTCTATGAATCATTATGTGAGAAAGCAGGATAACATTAGGTAACCTGAGCCTCCTGTGTGGTATTAGAA
AGTATACCGTCACCTTTTCACATCACTGGAGTGTAAAATTTAAAACAAGATGGTGATTCCTGACATTCCT
TGGCTGTCAGTGCTGCCCAGATTCAGAAGAATATTGCCCACATTTCACTGTATTTGGTGCTGGGTCATTT
TGACCTTGCTTTGTTAATAATATCTTTAAAAACAAAGACAATCCTTAAAGCTTTGCTCCTCACACATTAC
CTTCTAATTATAGTTTGAAAATAGATTCCCTACACATACATACATATGTATGCACAGATAGGGTCTTGCT
ATGTTGCCCAGGCTGGTCTTGAACTCCTGGCCTCAAGCAATCCTCTCTCCTCAGCCTCCCAAAGTGCTGG
GATTACAAGTGTGAGCCACCACACCTGGCTCCAGAAATTTTATTTTATTTTTTTGAGGCAGGGTCTCACT
CTGGTTGCCCAGGCTGGAGTGCAGTGGTGCCATCATAGCTCACTGTAGCCTCGACCTTCCGGGATCAAGC
AATCCCACTTCAGCCTCTTGAATAGCTGGGACTAGAAGCATGCACCACCATGCCCATCTAATATTTGTAT
TTTTAGTAGAGACAGGATCTCCCTATGTTGTCCAGCCTAGTCTCAAACTCCTGGGTTCAAGCAATCCTCC
CACCTCGGCCTCCCAAAGTGCTGGGATTGCAGGCATGAGCCACCGTGCCCAGCCTCAAAAATATTTTTA
AAAGAAAAGAGAAAATAATTCTTCTGTCAAAGGAGGTTAAATTTTAGTTGATAGAGTACTTAAATGCATT
ACTTTATTAGGTTATGTAAGTGGTCAGTGCATTCCAGTATGTGTCACAACAGTGTAGTTCATATTCATGA
TAAAAATGAAACTGTGATAAGACATGAAAATTATATTATTAAAATGTTCAATGTAATGGTAATCATGAG
TATACTTAATTTTATTTATGTATAGAATATTTGTATTTATTTTTTGGACATATATTTATCACTTTGTCAT
TTTTTTTAACCAATTTGAGAAATGTTAGCTGCTGAATTAATTTGTTGCCCGAGCCTTCATATTTTCTTCT
TTGCTGCCTTCTCCCTGTGGCAATGTACTGTTCTCACATTAAGCCTTTTAAAAATGTTCCATACTGTATT
AGCATCCTTAGAAGGGACAGAACTAAGAAATACATTGCTCAAATAATATTTTACTTTATTGATAATGACA
AAAGAATATTTTTAAACCCCATCAAAATAGATTTCAATTGACTGTTTCCCCTACATCTTTTGAGCCAC
AGTCGCCCATCGAATAAGCAAATTTGTTTTTGAGAATAAACTGGTAACCAGTTTGTGATGACTCTCAGAA
GCCTTTTGGCTGGGTTACAGAAGAGTTTCTAAGTTCCTAGAGAGCCATTTAATAATTAGTTGGTGAGCCA
GAGGCTTGACAGAGCTGTTACTTATGTGTGAGGGCTTTATTCTCAGGCAGTAGTTTATTCATCATTTGGT
AAGCCCCTCCCCACACTCCTCTAATTTAAACAAGTAGTGAAGGCTTATCTTAAACTGTGTAGTACCTTAG
```

-continued

```
ACTTGGCATTTATTTTTGATAGAGCAGAGATAAAATATTTTGATGGAAGGAAATCAATTTTCTGTAACTG

ATGATGTGAAAATTTTATTTTCTGGGAAATTATATAGCCATTCAAAAATTCAAAGTATGTTATTATGATT

GGTTACAAGAGAATAATGTTACATGTTTAATTGTAATATTTGTCTCCTATCATTTTCTTCCCTTTCAGTC

ATAATAAATGATTTACAAAACCCAAAAAAAAAAAAAAAAAAA.
```

Example 1

Results

Meta-Analysis Identified a 587-Gene Signature Frequently Deregulated in Human Breast Cancer.

Figures 1A, 1B:
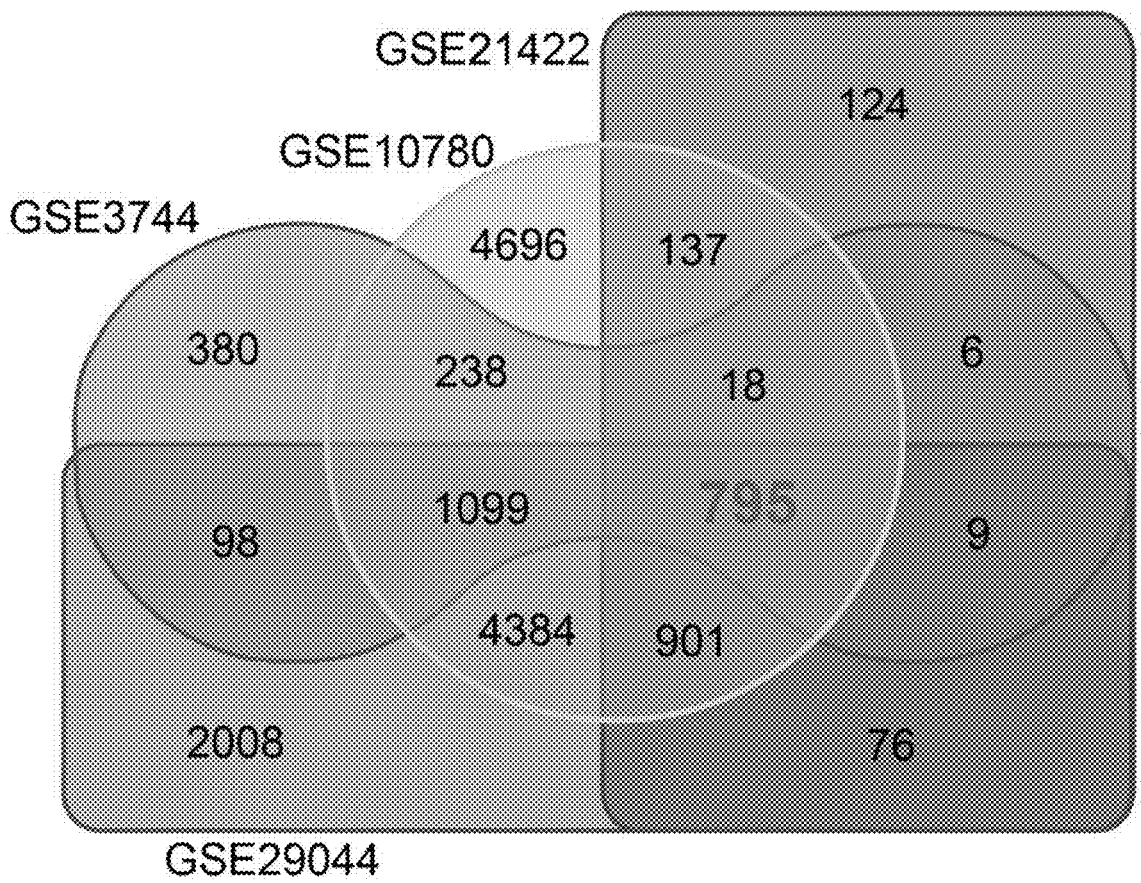
FIG. 1A shows the four independent gene transcript data sets containing invasive ductal carcinoma and normal breast tissue samples were used in this study.
FIG. 1B shows differential expression of tumor versus normal using a fold-change cutoff of 1.5 and adjusted p-value 0.01 identified the 795 common probe ID set.

We conducted a meta-analysis of genes consistently deregulated in human breast cancers. We collected gene transcript data from normal and tumor breast tissues represented by four independent gene expression data sets totaling 160 invasive ductal carcinomas and 191 normal breast tissues (FIG. 1A) [11-15]. The significant differential expression of genes was assessed by a fold change cutoff of 1.5 and adjusted p-value<0.01 (Table S1). This resulted in a gene signature of 795 probe IDs (590 down-regulated and 205 up-regulated) represented by 587 unique genes, for which the direction of expression was consistent across all four datasets (FIG. 1B; Table S2).

381 Genes Significantly Associated with Relapse-Free Survival in Breast Cancer Patients.

To investigate whether any of the 587 common deregulated genes were associated with relapse-free survival (RFS), we evaluated the prognostic value for each individual gene in a large public clinical microarray database using the Kaplan-Meier plotter (website for kmplot.com/) [16]. The BC patient cohort was divided into two equal groups based on median expression for each gene and compared by a Kaplan-Meier survival analysis. In addition, the hazard ratio with a 95% confidence interval and logrank p-value was calculated to evaluate the prognostic significance of each gene for RFS. This analysis identified 381 genes significantly associated with RFS (p-value<6.3E-05; FIG. 3, Table S3); 249 genes had a hazard ratio <1 (higher gene expression associated with good prognosis) and 133 genes had a hazard ratio >1 (higher gene expression associated with poor prognosis).

Genes that Predict Prognosis are Enriched for Microenvironment- and Cell Cycle-Related Biological Processes.

To reveal the biological functions enriched in the 381-gene set associated with RFS, we performed Gene Ontology analysis separately on the 249 genes that exhibited a HR<1 and 133 genes with HR>1. The 249-gene signature (HR<1) was significantly enriched for tissue microenvironment related processes including cell adhesion (adj. p-value=6E-04), cell migration (adj. p-value=2.74E-05), wound healing (adj. p-value=3.1E-03), and vasculature development (adj. p-value=4.13E-05) (Table S4). On the other hand, the 133-gene signature (HR>1) was strongly enriched for cell cycle related processes (adj. p-value=5.33E-51) (Table S4). This strong dichotomy between RFS genes with HR<1—associated with tumor processes enriched for tissue microenvironment-related biological functions (e.g. vasculature, wound healing, cell migration)—and RFS genes with HR>1—almost exclusively associated with cell cycle related processes—prompted us to further investigate the genetic architecture of these genes in normal breast tissues and BCs.

Gene Co-Expression Network Analysis Visualizes the Genetic Architecture of RFS Associated Genes in Normal Breast and Breast Cancer.

Since gene sets that are correlated in expression across tissue samples often share a common function, co-expression network analysis has been used to identify clusters of genes with common biological functionality important in normal or tumor tissues. We used data obtained from the GTEX database of 214 normal human breast tissues and the TCGA database of 1100 BC samples to reveal the genetic architecture of RFS associated genes in normal and tumor breast tissue. We first calculated correlation coefficients of 381 genes associated with RFS across 214 normal human breast tissues and 1100 breast cancer samples (FIG. 4A). We then constructed a gene expression correlation network where nodes represented individual gene and edges connecting genes represented a correlation in their expression (FIG. 4B, R≥|0.6|; p-value<8E-08). In normal breast tissue, three main co-expression cliques were identified (FIG. 4B). One clique was highly enriched for genes involved in cell cycle and mitosis, and whose genes all had a hazard ratio for RFS>1 (FIG. 4B, 4D). The remaining two co-expression cliques contained predominantly genes with a hazard ratio for RFS<1. One clique was enriched for genes involved in transcriptional regulation and cell adhesion, while the other clique was generally involved in cytoskeleton organization and metabolic processes. Interestingly, while expression levels of genes within each clique were predominantly positively correlated, expression levels of genes between these two cliques were negatively correlated (FIG. 4C). The cell cycle clique is connected to these two cliques through EZH2, MCM2 and MAD2L1.

A similar co-expression correlation analysis using TCGA data revealed two main co-expression cliques (FIG. 5A, 5B). Similar to normal breast tissue, one clique was highly enriched for genes involved in cell cycle and mitosis, all of which had a hazard ratio for RFS>1 (FIG. 5B). The remaining clique contained genes with a hazard ratio for RFS<1 and was enriched for blood vessel development, cell adhesion and mammary gland development. These two co-expression cliques were negatively correlated through 7 genes: CREBRF, DIXDC1, AHNAK, CYBRD1, NOSTRIN, TNS2 and TNFSF12 (FIG. 5C). Given the negative correlation with cell cycle related genes, these 7 genes could mediate negative regulation of cell growth and are potential therapeutic targets.

A 12-Gene Prognostic Signature Predicts Breast Cancer Patient Survival.

Using the 381-gene set associated with RFS we developed a gene signature that accurately predicts BC patient survival. We created 60 training sets through randomly selecting 300 patients each time from the BC gene expression dataset GSE6532, which has RFS information of 393 patients. The residual 93 patients from all 60 training sets formed the 60 test sets. We then performed Cox regression analysis on all 60 training sets to simultaneously assess the importance of the genes within the 381-gene in the RFS. The genes that recurred in at least half of the training sets were included in our final 12-gene signature: EPS15, MELK, NUF2, PLEKHH2, PLPP1, RNASEH2A, S100P, THYN1, TIMM17A, TSC1, USP47, ZBTB16.

The average beta-value (Cox regression coefficient) of each of the 12 genes was calculated and used as a weighting factor for the expression value of each gene. A prognostic score was estimated for each patient: gene expression values were multiplied by their respective beta-value and the prognostic score was determined as the sum of resulting weighted gene expression values. The patients were ranked by their prognostic score, divided into two equal sized cohorts based on the median score, and Kaplan-Meier analysis was performed to determine differences in RFS between two cohorts. Using the mean beta values developed in the training set, prognostic scores were calculated for all patients in the 60 test sets. Patients were again ranked on their prognostic score and divided into two cohorts based on the average prognostic-score cut-point in the 60 training sets. Kaplan-Meier analysis was performed and a log-rank test was used to determine if there was a significant difference in RFS between two cohorts. The hazard ratio was calculated for each of the 60 test sets. In only 2 out of 60 (3.3%) test sets, the hazard ratio confidence interval crossed "1" (FIG. 6A).

Validation of 12-Gene Prognostic Signature.

We then tested our 12-gene prognostic signature in an independent set of 1100 BC patients obtained from the TCGA database. Prognostic scores for all 1100 patients were calculated and patients were ranked based on their score and divided into two equal sized cohorts. Kaplan-Meier analysis revealed a significant difference between the two patient cohorts. Patients with a high prognostic score had a significantly shorter overall survival compared to patients with a low prognostic score (FIG. 6B; p<0.001). To determine if our prognostic score was independent of age at diagnosis, tumor stage, estrogen- and progesterone-receptor status, we ran multivariate Cox regression force-entry with these factors including the prognostics scores as covariates. We found that prognostic score, age at diagnosis and tumor stages III and IV (compared to stage I) were significantly associated with overall survival (FIG. 6C). These data confirmed that our prognostic score has clinical validity independent of tumor stage and age at diagnosis (p-value=0.007, HR=2.1, 95% CI:1.2-3.7) (FIG. 6C).

We further validated our 12-gene prognostic signature in a second independent breast cancer dataset consisting of 1980 BC patients and containing data for individual breast cancer molecular subtypes (METABRIC; [17, 18]). Prognostic scores for all 1980 patients were calculated as described above for the TCGA cohort and patients were ranked based on their score and divided into two equal sized cohorts. Kaplan-Meier analysis revealed a significant difference between the two patient cohorts (FIG. 7A; p=1.01E-17). To address the interaction of our signature with breast cancer molecular subtypes we stratified our patient cohort by molecular subtype (based on PAM50; [19]) and used Kaplan-Meier analysis to investigate differences in survival between the low and high prognostic score cohorts. We found that higher prognostic score was significantly associated with shorter survival in "normal-like", "luminal A" and "HER2" subtypes (FIG. 7B). To determine, in this data set, if our prognostic score was independent of age at diagnosis, tumor grade, estrogen- and progesterone-receptor status and molecular subtype (PAM50) we ran multivariate Cox regression force-entry with these factors including the prognostics scores as covariates. We further confirmed that our prognostic signature has clinical validity independent of age at diagnosis, estrogen receptor status, tumor grade and molecular subtype.

Discussion

Selecting patients who would most likely benefit from adjuvant systemic therapy is important considering the associated risks of treatment; the development of prognostic biomarkers is useful in this regard. While it remains difficult to identify good targets for the development of targeted therapies, cancer genome analysis has shown great promise in identifying key aberrations in tumor growth and survival pathways that could serve as prognostic biomarkers and targets for therapeutic intervention. We created a 12-gene prognostic scoring system, which robustly predicted BC patients' RFS in independent breast cancer data sets. Our gene signature could guide adjuvant therapy for breast cancer patients and includes novel potential molecular targets for therapy. Genes in our signature did not overlap with existing gene signatures that predict breast cancer outcome and metastasis [20-22]. Multiple reasons can explain the lack of overlap between these signatures, including differences in sample size and data sets, clinical phenotypes and methods of signature development. Also, we have shown using co-expression network analysis that functionally related genes often strongly correlate in expression. Even though different signatures select different genes, they may still originate from co-expression cliques representing the same biological function. For example, the Oncotype DX gene signature, which is prognostic of breast cancer recurrence, consists of 16 cancer genes. Five of these genes were also included in our analysis (MKi67, STK15, BIRC5, CCNB1 and MMP11), but were not selected in our final gene signature. However, MKi67, STK15, BIRC5 and CCNB1 were all part of the same strongly interconnected and cell-cycle enriched co-expression clique. Our analysis selected NUF2, MELK and RNASEH2A from the same clique, however, given the strong correlations in expression, any one of the highly connected genes is likely to perform equally well. Using multivariate Cox regression with our 12-gene signature and the Oncotype DX 16-gene signature, we determined that our 12-gene signature was independent (p<0.005; HR=2.4, 95% CI:1.7-3.4), but equally important as the Oncotype DX gene signature (p<0.005; HR=2.2, 95% CI: 1.3-3.7). Another important variable associated with breast cancer survival is molecular subtype. Using a cohort of 1980 breast cancer patients with approximately 30 years of follow-up we determined that our signature could predict breast cancer patient survival for "normal-like", "luminal-A" and "HER2" subtypes, but not "luminal-B", "basal" and "claudin-low" subtypes. We should point out that in our analysis patients were stratified into two equally sized cohorts based on the median prognostic score and then further stratified by molecular subtype. This resulted in unequally sized cohorts for each subtype, which could potentially have confounded our analysis. To test this, we generated equally sized cohorts based on prognostic score for each individual subtype. We first stratified patients by molecular subtype and then further stratified patients inside each subtype by the median of the prognostic score. This analysis revealed similar observations as presented in FIG. 7B confirming that our results are not confounded by unequally sized cohorts within different score groups. Future studies are granted to investigate whether our prognostic score can predict sensitivity to radiation- and/or chemotherapy.

The majority of the genes in our signature have previously been associated with cancer progression and patient outcome. MELK, NUF2 and ZBTB16 play important roles in cell cycle-related processes. Loss of ZBTB16 expression has been reported in a number of different tumor types including prostate cancer, non-small cell lung cancer, melanoma [23-25]. Overexpression of MELK, a serine/threonine kinase implicated in embryogenesis and cell cycle control has been identified in numerous human cancer types including breast, prostate, brain, colorectal and gastric cancer [26-30]. In BC, overexpression of MELK correlated with poor prognosis, whereas knockdown decreased proliferation [28, 30, 31]. NUF2 is part of a conserved protein complex associated with the centromere and plays a regulatory role in chromosomal segregation. Down regulation of NUF2 in pancreatic cancer cell lines inhibited tumor growth and enhanced apoptosis [32] whereas upregulation of NUF2 in colon cancer cells promoted tumorigenicity [33]. Overexpression of EPS15, which plays a role in terminating growth factor signaling, was shown to be a favorable prognostic factor in BC [34, 35]. Our signature also included the inner mitochondrial membrane protein TIMM17A. Decreased expression of TIMM17A reduced the aggressiveness of BC cells and TIMM17A expression was significantly associated with BC survival [36-38]. PLEKHH2 and TSC1 are involved in cell adhesion and actin dynamics. Loss of TSC1 was shown to result in the deregulation of cell motility and adhesion [39]. A polymorphic variant of TSC1 was associated with delayed age at diagnosis of ER-positive ductal carcinomas [40]. Also, TSC1, in coordination with TSC2, inhibits MTOR, which promotes cell growth and cell cycle progression [41]. PLPP1 degrades lysophosphatidate and is often down-regulated in tumor types. Using syngeneic and xenograft mouse models showed that PLPP1 overexpression in BC cells decreased tumor growth and the metastasis [42]. S100P is overexpressed in a variety of human tumor types [43]. S100P transcription is influenced by a number of signaling molecules including progesterone, androgens, glucocorticoids, BMP4 and IL6 and through interactions with a various proteins integrates and regulates multiple signaling pathways involved in degradation of extracellular matrix, invasion and metastasis and tumorigenesis (reviewed in [44]).

The role of PLEKHH2, USP47 and THYN1 has not been extensively studied in cancer progression. PLEKHH2 protein was enriched in renal glomerular podocytes, and shown to interact with focal adhesion proteins and actin to stabilize the actin cytoskeleton [45]. USP47 plays an important role in base-excision repair and the maintenance of genome integrity [46]. Depletion of USP47 induced accumulation of Cdc25A and decreased cell survival [47]. However, our results indicate that patients with high breast tumor expression of USP47 have significantly better relapse-free survival compared to patients with low breast tumor expression of USP47 (HR=0.65; p-value=2.40E-07). Thus, the exact role of USP47 in BC has yet to be determined. The role of THYN1 in BC is currently unknown, however, downregulation of THYN1 has been correlated with the induction of apoptosis in a specific B-cell lymphoma cell line [48].

Our gene co-expression network analysis identified a number of potential therapeutic targets. We found that 7 genes CREBRF, DIXDC1, AHNAK, CYBRD1, NOSTRIN, TNS2 and TNFSF12 were negatively correlated with the strongly interconnected cell cycle and mitosis clique. Indeed, a number of these genes have been identified as candidate tumor suppressor genes including CREBRF, DIXDC1, AHNAK and TNS2 [49-52]. Furthermore, NOSTRIN was found to be a potential negative regulator of disease aggressiveness in pancreatic cancer and CYBRD1 was identified as part of an iron regulatory gene signature that predicts outcome in BC [53, 54]. TNFSF12 (TWEAK) can promote cell death in tumor cell lines under certain conditions [55-57], and may also activate local macrophages to inhibit tumor progression [58]. The negative correlation of these 7 genes with the cell cycle enriched gene co-expression clique was observed in the co-expression network of breast tumor samples, but not the normal breast tissue co-expression network. This suggests that a therapeutic approach that increases expression of one or more of these 7 genes could collapse the tumor cell cycle machinery, while sparing adverse effects in healthy tissue.

In summary, we have generated a prognostic scoring system and 12-gene signature that is prognostic of BC patient relapse-free survival. Furthermore, using co-expression network analysis, we investigated the genetic architecture of RFS associated genes in normal and tumor tissues and identified 7 potential therapeutic targets that could be developed to target the tumor cell cycle machinery. Our analysis pipeline could furthermore be applied to other tumor types.

Materials and Methods

Data Sets Used in this Study.

Gene transcript data of normal and tumor breast tissues was obtained from NCBI GEO accession numbers: GSE3744 (40 invasive ductal carcinoma samples and 7 normal breast samples), GSE10780 (42 invasive ductal carcinoma samples and 143 normal breast samples), GSE21422 (5 invasive ductal carcinoma samples and 5 normal breast samples) and GSE29044 (72 invasive ductal carcinoma samples and 36 normal breast samples). Normal breast gene transcript data used for generating gene expression correlation networks was obtained from GTEX (website for: gtexportal.org/home/datasets) using the RPKM normalized gene transcript counts table [9, 10].

Statistical Analysis.

GEO2R was used to calculate the differential expression of tumor versus normal using a fold-change cutoff of 1.5 and adjusted p-value 0.01. Association of differentially expressed genes and relapse-free survival in breast cancer patients was assessed using Kaplan-Meier plotter (website for: kmplot.com) including KM survival analysis, hazard ratio with 95% confidence interval and logrank p-value for each gene using all available patients (not restricted to any clinical parameters such as grade, PR status, etc) [16].

Gene ontology enrichment analysis was performed using the web-based gene set analysis toolkit (adjusted p<0.05 was used as a threshold for significance) (website for: bioinfo.vanderbilt.edu/webgestalt/) [59, 60].

Gene Co-Expression Network Construction.

Gene expression Spearman correlation coefficients were calculated in "R" for 795 probes (587 genes) that were differentially expressed between breast tumor and normal tissues samples. A gene network was generated where nodes represent individual genes and edges connecting nodes were drawn when the correlation coefficient exceeded $|R|\geq 0.6$ (adjusted p-value≤7.911E-08). The gene co-expression network was visualized using Cytoscape 3.1.1. (website for: cytoscape.org).

Prognostic Gene Signature.

BC microarray data (GSE6532), describing RFS status and gene expression for our 357-gene panel, was collected for 393 patients. Sixty random samplings of 300 patients were extracted from this dataset and used as training sets to identify a biomarker panel associated with RFS. The residual 93 patients from each sample were used as test sets to validate the prognostic significance of the biomarker panel. A forward-conditional Cox regression using all 357 genes as covariates was performed using SPSS on each of the training sets in order to identify the biomarker panel. The results of each test were recorded and the genes that appeared in more than half of the training sets were included in our biomarker panel.

Cox regression was repeated on all 60 training sets using our 12-gene signature as covariates using the forced-entry (enter) method to obtain the beta values (coefficient) for each biomarker. The resulting 60 beta values of each biomarker were averaged to estimate the true beta value of each gene. A prognostic scoring system was created based on this formula.

$$\sum_{i=1}^{12} (\text{gene } i \, \beta) \times (\text{gene } i \text{ expression level})$$

The patients were ranked by their prognostic score and divided into two equal sized cohorts. Kaplan-Meier plots were constructed and a long-rank test was used to determine differences among relapse free survival.

Prognostic scores for each of the test set samples were then calculated using the same set of mean beta values developed in the training set. Patients were ranked based on their prognostic score and divided into two cohorts based on the average prognostic-score cut-point in the training sets. Kaplan-Meier plots were constructed and a log-rank test was used to determine differences among RFS.

To further validate our biomarker panel, mRNA expression levels (normalized RNA-seq mRNA expression z-scores) for our 12-gene signature were obtained from cBioPortal for 1100 breast cancer samples (TCGA; website for: cbioportal.org/data_sets.jsp) [61, 62] and for 1980 breast cancer samples (METABRIC) [17, 18]. New beta values for each of the twelve biomarkers were obtained using Cox regression. Prognostic scores were calculated and patients were ranked based on their score and divided into two equal sized cohorts. Kaplan-Meier analysis and a log-rank test were used to determine differences in survival.

REFERENCES

1. DeSantis C, Ma J, Bryan L and Jemal A. Breast cancer statistics, 2013. CA: a cancer journal for clinicians. 2014; 64(1):52-62.
2. Siegel R, Ma J, Zou Z and Jemal A. Cancer statistics, 2014. CA: a cancer journal for clinicians. 2014; 64(1):9-29.
3. Holloway C M, Easson A, Escallon J, Leong W L, Quan M L, Reedjik M, Wright F C and McCready D R. Technology as a force for improved diagnosis and treatment of breast disease. Canadian journal of surgery Journal canadien de chirurgie. 2010; 53(4):268-277.
4. Duffy S W, Lynge E, Jonsson H, Ayyaz S and Olsen A H. Complexities in the estimation of overdiagnosis in breast cancer screening. British journal of cancer. 2008; 99(7):1176-1178.
5. Glass A G, Lacey J V, Jr., Carreon J D and Hoover R N. Breast cancer incidence, 1980-2006: combined roles of menopausal hormone therapy, screening mammography, and estrogen receptor status. Journal of the National Cancer Institute. 2007; 99(15):1152-1161.
6. Anampa J, Makower D and Sparano J A. Progress in adjuvant chemotherapy for breast cancer: an overview. BMC medicine. 2015; 13:195.
7. Chew H K. Adjuvant therapy for breast cancer: who should get what? The Western journal of medicine. 2001; 174(4):284-287.
8. Cianfrocca M and Goldstein U. Prognostic and predictive factors in early-stage breast cancer. The oncologist. 2004; 9(6):606-616.
9. Consortium G T. The Genotype-Tissue Expression (GTEx) project. Nature genetics. 2013; 45(6):580-585.
10. Mele M, Ferreira P G, Reverter F, DeLuca D S, Monlong J, Sammeth M, Young T R, Goldmann J M, Pervouchine D D, Sullivan T J, Johnson R, Segre A V, Djebali S, Niarchou A, Consortium G T, Wright F A, et al. Human genomics. The human transcriptome across tissues and individuals. Science. 2015; 348(6235):660-665.
11. Alimonti A, Carracedo A, Clohessy J G, Trotman L C, Nardella C, Egia A, Salmena L, Sampieri K, Haveman W J, Brogi E, Richardson A L, Zhang J and Pandolfi P P. Subtle variations in Pten dose determine cancer susceptibility. Nature genetics. 2010; 42(5):454-458.
12. Richardson A L, Wang Z C, De Nicolo A, Lu X, Brown M, Miron A, Liao X, Iglehart J D, Livingston D M and Ganesan S. X chromosomal abnormalities in basal-like human breast cancer. Cancer cell. 2006; 9(2):121-132.
13. Colak D, Nofal A, Albakheet A, Nirmal M, Jeprel H, Eldali A, Al-Tweigeri T, Tulbah A, Ajarim D, Malik O A, Inan M S, Kaya N, Park B H and Bin Amer S M. Age-specific gene expression signatures for breast tumors and cross-species conserved potential cancer progression markers in young women. PloS one. 2013; 8(5):e63204.
14. Kretschmer C, Sterner-Kock A, Siedentopf F, Schoenegg W, Schlag P M and Kemmner W. Identification of early molecular markers for breast cancer. Molecular cancer. 2011; 10(1):15.
15. Chen D T, Nasir A, Culhane A, Venkataramu C, Fulp W, Rubio R, Wang T, Agrawal D, McCarthy S M, Gruidl M, Bloom G, Anderson T, White J, Quackenbush J and Yeatman T. Proliferative genes dominate malignancy-risk gene signature in histologically-normal breast tissue. Breast cancer research and treatment. 2010; 119(2):335-346.
16. Gyorffy B, Lanczky A, Eklund A C, Denkert C, Budczies J, Li Q and Szallasi Z. An online survival analysis tool to rapidly assess the effect of 22,277 genes on breast cancer prognosis using microarray data of 1,809 patients. Breast cancer research and treatment. 2010; 123(3):725-731.
17. Curtis C, Shah S P, Chin S F, Turashvili G, Rueda O M, Dunning M J, Speed D, Lynch A G, Samarajiwa S, Yuan Y, Graf S, Ha G, Haffari G, Bashashati A, Russell R, McKinney S, et al. The genomic and transcriptomic architecture of 2,000 breast tumours reveals novel subgroups. Nature. 2012; 486(7403):346-352.
18. Pereira B, Chin S F, Rueda O M, Vollan H K, Provenzano E, Bardwell H A, Pugh M, Jones L, Russell R, Sammut S J, Tsui D W, Liu B, Dawson S J, Abraham J, Northen H, Peden J F, et al. The somatic mutation profiles of 2,433 breast cancers refines their genomic and transcriptomic landscapes. Nature communications. 2016; 7:11479.
19. Parker J S, Mullins M, Cheang M C, Leung S, Voduc D, Vickery T, Davies S, Fauron C, He X, Hu Z, Quackenbush J F, Stijleman I J, Palazzo J, Marron J S, Nobel A B, Mardis E, et al. Supervised risk predictor of breast cancer based on intrinsic subtypes. Journal of clinical oncology: official journal of the American Society of Clinical Oncology. 2009; 27(8):1160-1167.
20. van't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R and Friend S H. Gene expression profiling predicts clinical outcome of breast cancer. Nature. 2002; 415(6871):530-536.
21. Wang Y, Klijn J G, Zhang Y, Sieuwerts A M, Look M P, Yang F, Talantov D, Timmermans M, Meijer-van Gelder M E, Yu J, Jatkoe T, Berns E M, Atkins D and Foekens J A. Gene-expression profiles to predict distant metastasis of lymph-node-negative primary breast cancer. Lancet. 2005; 365(9460):671-679.
22. Paik S, Shak S, Tang G, Kim C, Baker J, Cronin M, Baehner F L, Walker M G, Watson D, Park T, Hiller W, Fisher E R, Wickerham D L, Bryant J and Wolmark N. A multigene assay to predict recurrence of tamoxifen-treated, node-negative breast cancer. The New England journal of medicine. 2004; 351(27):2817-2826.
23. Xiao G Q, Unger P, Yang Q, Kinoshita Y, Singh K, McMahon L, Nastiuk K, Sha K, Krolewski J and Burstein D. Loss of PLZF expression in prostate cancer by immunohistochemistry correlates with tumor aggressiveness and metastasis. PloS one. 2015; 10(3):e0121318.
24. Wang X, Wang L, Guo S, Bao Y, Ma Y, Yan F, Xu K, Xu Z, Jin L, Lu D, Xu J and Wang J C. Hypermethylation reduces expression of tumor-suppressor PLZF and regulates proliferation and apoptosis in non-small-cell lung cancers. FASEB journal: official publication of the Federation of American Societies for Experimental Biology. 2013; 27(10):4194-4203.
25. Brunner G, Reitz M, Schwipper V, Tilkorn H, Lippold A, Biess B, Suter L and Atzpodien J. Increased expression of the tumor suppressor PLZF is a continuous predictor of long-term survival in malignant melanoma patients. Cancer biotherapy & radiopharmaceuticals. 2008; 23(4):451-459.
26. Du T, Qu Y, Li J, Li H, Su L, Zhou Q, Yan M, Li C, Zhu Z and Liu B. Maternal embryonic leucine zipper kinase enhances gastric cancer progression via the FAK/Paxillin pathway. Molecular cancer. 2014; 13:100.
27. Kuner R, Falth M, Pressinotti N C, Brase J C, Puig S B, Metzger J, Gade S, Schafer G, Bartsch G, Steiner E, Klocker H and Sultmann H. The maternal embryonic leucine zipper kinase (MELK) is upregulated in high-grade prostate cancer. Journal of molecular medicine. 2013; 91(2):237-248.
28. Pickard M R, Green A R, Ellis T O, Caldas C, Hedge V L, Mourtada-Maarabouni M and Williams G T. Dysregulated expression of Fau and MELK is associated with poor prognosis in breast cancer. Breast cancer research: BCR. 2009; 11(4):R60.
29. Nakano I, Masterman-Smith M, Saigusa K, Paucar A A, Horvath S, Shoemaker L, Watanabe M, Negro A, Bajpai R, Howes A, Lelievre V, Waschek J A, Lazareff J A, Freije W A, Liau L M, Gilbertson R J, et al. Maternal embryonic leucine zipper kinase is a key regulator of the proliferation of malignant brain tumors, including brain tumor stem cells. Journal of neuroscience research. 2008; 86(1):48-60.
30. Gray D, Jubb A M, Hogue D, Dowd P, Kljavin N, Yi S, Bai W, Frantz G, Zhang Z, Koeppen H, de Sauvage F J and Davis D P. Maternal embryonic leucine zipper kinase/murine protein serine-threonine kinase 38 is a promising therapeutic target for multiple cancers. Cancer research. 2005; 65(21):9751-9761.
31. Wang Y, Lee Y M, Baitsch L, Huang A, Xiang Y, Tong H, Lako A, Von T, Choi C, Lim E, Min J, Li L, Stegmeier F, Schlegel R, Eck M J, Gray N S, et al. MELK is an oncogenic kinase essential for mitotic progression in basal-like breast cancer cells. eLife. 2014; 3:e01763.
32. Hu P, Shangguan J and Zhang L. Downregulation of NUF2 inhibits tumor growth and induces apoptosis by regulating lncRNA AF339813. International journal of clinical and experimental pathology. 2015; 8(3):2638-2648.
33. Sugimasa H, Taniue K, Kurimoto A, Takeda Y, Kawasaki Y and Akiyama T. Heterogeneous nuclear ribonucleoprotein K upregulates the kinetochore complex component NUF2 and promotes the tumorigenicity of colon cancer cells. Biochemical and biophysical research communications. 2015; 459(1):29-35.
34. Dai X, Liu Z and Zhang S. Over-expression of EPS15 is a favorable prognostic factor in breast cancer. Molecular bioSystems. 2015; 11(11):2978-2985.
35. Amatschek S, Koenig U, Auer H, Steinlein P, Pacher M, Gruenfelder A, Dekan G, Vogl S, Kubista E, Heider K H, Stratowa C, Schreiber M and Sommergruber W. Tissue-wide expression profiling using cDNA subtraction and microarrays to identify tumor-specific genes. Cancer research. 2004; 64(3):844-856.
36. Yang X, Si Y, Tao T, Martin T A, Cheng S, Yu H, Li J, He J and Jiang W G. The Impact of TIMM17A on Aggressiveness of Human Breast Cancer Cells. Anticancer research. 2016; 36(3):1237-1241.
37. Salhab M, Patani N, Jiang W and Mokbel K. High TIMM17A expression is associated with adverse pathological and clinical outcomes in human breast cancer. Breast cancer. 2012; 19(2):153-160.
38. Xu X, Qiao M, Zhang Y, Jiang Y, Wei P, Yao J, Gu B, Wang Y, Lu J, Wang Z, Tang Z, Sun Y, Wu W and Shi Q. Quantitative proteomics study of breast cancer cell lines isolated from a single patient: discovery of TIMM17A as a marker for breast cancer. Proteomics. 2010; 10(7):1374-1390.
39. Goncharova E, Goncharov D, Noonan D and Krymskaya V P. TSC2 modulates actin cytoskeleton and focal adhesion through TSC1-binding domain and the Rac 1 GTPase. The Journal of cell biology. 2004; 167(6):1171-1182.
40. Mehta M S, Vazquez A, Kulkarni D A, Kerrigan J E, Atwal G, Metsugi S, Toppmeyer D L, Levine A J and Hirshfield K M. Polymorphic variants in TSC1 and TSC2 and their association with breast cancer phenotypes. Breast cancer research and treatment. 2011; 125(3):861-868.
41. Findlay G M, Harrington L S and Lamb R F. TSC1-2 tumour suppressor and regulation of mTOR signalling: linking cell growth and proliferation? Current opinion in genetics & development. 2005; 15(1):69-76.
42. Tang X, Benesch M G, Dewald J, Zhao Y Y, Patwardhan N, Santos W L, Curtis J M, McMullen T P and Brindley D N. Lipid phosphate phosphatase-1 expression in cancer cells attenuates tumor growth and metastasis in mice. Journal of lipid research. 2014; 55(11):2389-2400.
43. Parkkila S, Pan P W, Ward A, Gibadulinova A, Oveckova I, Pastorekova S, Pastorek J, Martinez A R, Helin H O and Isola J. The calcium-binding protein S100P in normal and malignant human tissues. BMC clinical pathology. 2008; 8:2.

44. Prica F, Radon T, Cheng Y and Crnogorac-Jurcevic T. The life and works of S100P—from conception to cancer. American journal of cancer research. 2016; 6(2):562-576.
45. Perisic L, Lal M, Hulkko J, Hultenby K, Onfelt B, Sun Y, Duner F, Patrakka J, Betsholtz C, Uhlen M, Brismar H, Tryggvason K, Wernerson A and Pikkarainen T. Plekhh2, a novel podocyte protein downregulated in human focal segmental glomerulosclerosis, is involved in matrix adhesion and actin dynamics. Kidney international. 2012; 82(10):1071-1083.
46. Parsons J L, Dianova, I I, Khoronenkova S V, Edelmann M J, Kessler B M and Dianov G L. USP47 is a deubiquitylating enzyme that regulates base excision repair by controlling steady-state levels of DNA polymerase beta. Molecular cell. 2011; 41(5):609-615.
47. Peschiaroli A, Skaar J R, Pagano M and Melino G. The ubiquitin-specific protease USP47 is a novel beta-TRCP interactor regulating cell survival. Oncogene. 2010; 29(9):1384-1393.
48. Jiang X Z, Toyota H, Yoshimoto T, Takada E, Asakura H and Mizuguchi J. Anti-IgM-induced down-regulation of nuclear Thy28 protein expression in Ramos B lymphoma cells. Apoptosis: an international journal on programmed cell death. 2003; 8(5):509-519.
49. Lee I H, Sohn M, Lim H J, Yoon S, Oh H, Shin S, Shin J H, Oh S H, Kim J, Lee D K, Noh D Y, Bae D S, Seong J K and Bae Y S. Ahnak functions as a tumor suppressor via modulation of TGFbeta/Smad signaling pathway. Oncogene. 2014; 33(38):4675-4684.
50. Goodwin J M, Svensson R U, Lou H J, Winslow M M, Turk B E and Shaw R J. An AMPK-independent signaling pathway downstream of the LKB1 tumor suppressor controls Snail1 and metastatic potential. Molecular cell. 2014; 55(3):436-450.
51. Hong S Y, Shih Y P, Sun P, Hsieh W J, Lin W C and Lo S H. Down-regulation of tensin2 enhances tumorigenicity and is associated with a variety of cancers. Oncotarget. 2016.
52. Xue H, Zhang J, Guo X, Wang J, Li J, Gao X, Guo X, Li T, Xu S, Zhang P, Liu Q and Li G. CREBRF is a potent tumor suppressor of glioblastoma by blocking hypoxia-induced autophagy via the CREB3/ATG5 pathway. International journal of oncology. 2016; 49(2):519-528.
53. Miller L D, Coffman L G, Chou J W, Black M A, Bergh J, D'Agostino R, Jr., Torti S V and Torti F M. An iron regulatory gene signature predicts outcome in breast cancer. Cancer research. 2011; 71(21):6728-6737.
54. Wang J, Yang S, He P, Schetter A, Gaedcke J, Ghadimi B M, Ried T, Yfantis H G, Lee D H, Gaida M M, Hanna N, Alexander H R and Hussain S P. Endothelial Nitric Oxide Synthase Traffic Inducer (NOSTRIN) is a Negative Regulator of Disease Aggressiveness in Pancreatic Cancer. Clinical cancer research: an official journal of the American Association for Cancer Research. 2016.
55. Wilson C A and Browning J L. Death of HT29 adenocarcinoma cells induced by TNF family receptor activation is caspase-independent and displays features of both apoptosis and necrosis. Cell death and differentiation. 2002; 9(12):1321-1333.
56. Nakayama M, Ishidoh K, Kayagaki N, Kojima Y, Yamaguchi N, Nakano H, Kominami E, Okumura K and Yagita H. Multiple pathways of TWEAK-induced cell death. Journal of immunology. 2002; 168(2):734-743.
57. Schneider P, Schwenzer R, Haas E, Muhlenbeck F, Schubert G, Scheurich P, Tschopp J and Wajant H. TWEAK can induce cell death via endogenous TNF and TNF receptor 1. European journal of immunology. 1999; 29(6):1785-1792.
58. Gu L, Dai L, Cao C, Zhu J, Ding C, Xu H B, Qiu L and Di W. Functional expression of TWEAK and the receptor Fn14 in human malignant ovarian tumors: possible implication for ovarian tumor intervention. PloS one. 2013; 8(3):e57436.
59. Wang J, Duncan D, Shi Z and Zhang B. WEB-based GEne SeT AnaLysis Toolkit (WebGestalt): update 2013. Nucleic acids research. 2013; 41(Web Server issue):W77-83.
60. Zhang B, Kirov S and Snoddy J. WebGestalt: an integrated system for exploring gene sets in various biological contexts. Nucleic acids research. 2005; 33(Web Server issue):W741-748.
61. Cerami E, Gao J, Dogrusoz U, Gross B E, Sumer S O, Aksoy B A, Jacobsen A, Byrne C J, Heuer M L, Larsson E, Antipin Y, Reva B, Goldberg A P, Sander C and Schultz N. The cBio cancer genomics portal: an open platform for exploring multidimensional cancer genomics data. Cancer discovery. 2012; 2(5):401-404.
62. Gao J, Aksoy B A, Dogrusoz U, Dresdner G, Gross B, Sumer S O, Sun Y, Jacobsen A, Sinha R, Larsson E, Cerami E, Sander C and Schultz N. Integrative analysis of complex cancer genomics and clinical profiles using the cBioPortal. Science signaling. 2013; 6(269):p 11.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

What is claimed is:

1. A method for calculating a cancer patient's prognostic score comprising steps of: (a) measuring the gene expression level of the EPS15, MELK, NUF2, RNASEH2A, S100P, THYN1, TIMM17A, TSC1, USP47, ZBTB16, PLPP1, and PLEKHH2 genes in a patient's breast tumor tissue with a biomarker panel comprising the EPS15, MELK, NUF2, RNASEH2A, S100P, THYN1, TIMM17A, TSC1, USP47, ZBTB16, PLPP1, and PLEKHH2 genes; (b) calculating the prognostic score using the formula $$\sum_{i=1}^{12} (\text{gene } i\, \beta) \times (\text{gene } i \text{ expression level})$$

wherein the beta values for each of the 12 genes is obtained from Cox Hazard Regression model; (c) assigning the patient to an appropriate prognostic group based on the calculated prognostic score, whereby a high score above a threshold number indicates the patient has poor prognosis for breast cancer and a low score below the threshold number indicates the patient has good prognosis for relapse-free survival from breast cancer.

* * * * *

SEQUENCE LISTING

```
<160> NUMBER OF SEQ ID NOS: 12

<210> SEQ ID NO 1
<211> LENGTH: 5220
<212> TYPE: DNA
<213> ORGANISM: Homo sapiens

<400> SEQUENCE: 1
ggcctcgcct gcggccgctc cctccgcctc ctccccgccc cgagcccag tcagcccgtc      60 ttccttcccc tcccttgcat gatggaaaca ccatggctgc ggcggcccag ctctctctga    120
cacagttatc aagtgggaat cctgtatatg aaaaatacta tagacaggtt gatacaggca    180
atactggaag ggtgttggct tctgatgctg ctgctttcct gaaaaaatca gggcttccag    240
```

```
acttgatact tggaaagatt tgggatttag ccgacacaga tggcaaaggt atcctgaaca    300
aacaagaatt ctttgttgct ttgcgtcttg tggcatgtgc ccagaatgga ttggaagttt    360
cactaagtag tttgaacctg gctgttcctc caccaagatt tcatgatacc agtagtcctt    420
tgctaatcag tggaacctct gcagctgagc tcccatgggc tgtaaaacct gaagataagg    480
ccaaatatga tgcaatattt gatagtttaa gcccagtgaa tggatttctg tctggtgata    540
aagtgaaacc agtgttgctc aactctaagt tacctgtgga tatccttgga agagtttggg    600
agttgagtga tattgaccat gatggaatgc ttgacagaga tgagtttgca gttgccatgt    660
ttttggtata ctgtgcactg gagaaagaac ctgtgccaat gtccttgcct ccagccttgg    720
tgccaccatc taagagaaaa acgtgggttg tatcccctgc agaaaagct aaatatgatg    780 aaatcttcct gaaaactgat aaagatatgg acggatttgt gtctggattg gaggtccgtg    840
aaatattctt gaaaacaggt ttaccttcta ccttactagc ccatatatgg tcattatgcg    900
acacaaagga ctgtgggaag ctttcaaagg atcagtttgc cttggctttt cacttaatca    960
gtcagaagtt aatcaagggc attgatcctc ctcacgttct tactcctgaa atgattccac   1020
catcagacag ggccagttta caaaagaaca tcataggatc aagtcctgtt gcagatttct   1080
ctgctattaa ggaactagat actcttaaca atgaaatagt tgacctacag agggaaaaga   1140
ataatgtgga acaggacctt aaggagaagg aagatactat taaacagagg acaagtgagg   1200
ttcaggatct tcaagatgaa gttcaagggg agaatactaa tctgcaaaaa ctacaggccc   1260
agaaacagca ggtacaggaa ctccttgatg aactggatga gcagaaagcc cagctggagg   1320
agcaactcaa ggaagtcaga aagaaatgtg ctgaggaggc ccaactgatc tcttctctga   1380
aagctgaatt aactagtcag gaatcgcaga tctccactta cgaagaagaa ttggcaaaag   1440
ctagagaaga gctgagccgt ctacagcaag aaacagcaga attggaggag agtgtagagt   1500
cagggaaggc tcagttggaa cctcttcagc agcacctaca agattcacaa caggaaatta   1560
gttcaatgca aatgaaactg atggaaatga agatttgga aaatcataat agtcagttaa   1620
attggtgcag tagcccacac agcattcttg taaacggagc tacagattat tgcagcctca   1680
gcaccagcag cagtgaaaca gccaaccta atgaacatgt tgaaggccag agcaacctag   1740
agtctgagcc catacaccag gaatctccag caagaagtag tcctgaacta ctgccttctg   1800
gtgtgactga tgaaaatgag gtgactacag ctgttactga aaagtttgt tctgaactcg   1860 acaataatag acattcaaaa gaggaagatc catttaatgt agactcaagt tcgctgacag   1920
gtccagttgc agatacaaac ttggattttt tccagtctga tccttttgtt ggcagtgatc   1980
ctttcaagga tgatcctttt ggaaaaatcg atccatttgg tggtgatcct ttcaaaggtt   2040
cagatccatt tgcatcagac tgtttcttca ggcaatctac tgatcctttt gccacttcaa   2100
gcactgaccc tttcagtgca gccaacaata gcagtattac atcggtagaa acgttgaagc   2160
acaatgatcc ttttgctcct ggtggaacag ttgttcagc aagcgattca gccacagacc   2220
cctttgcttc tgttttggg aatgaatcat ttggaggtgg atttgctgac ttcagcacat   2280
tgtcaaaggt caacaatgaa gatccttttc gttcagccac atcgagctct gtcagcaacg   2340
tagtgattac aaaaaatgta tttgaggaaa catcggtcaa aagtgaagat gaaccccag   2400 cactgccacc aaagatcgga actccaacaa gaccctgccc tctaccacct gggaaaagat   2460
ccatcaacaa attggattct cctgatccct ttaaactgaa tgatccattt cagccttcc   2520 caggcaacga tagccccaaa gaaaaagatc ctgaaatatt ttgtgatcca ttcacttctg   2580
```

```
ctactaccac taccaataaa gaggctgatc caagcaattt tgccaacttc agtgcttatc    2640
cctctgaaga agatatgatc gaatgggcca agagggaaag tgagagagag aagagcaga     2700 ggcttgcccg actaaatcag caggaacaag aagacttaga actggctatt gcactcagca    2760
aatctgagat atcagaagca tgaagaattc tcttgttctt tggcaacaat atagtattct    2820
tcttcctgaa tactgaaact atttacaatg tgtatcaaaa ctacctgtga gcatgggaat    2880
acaaaaggtt tgagattcct gtaaatgtga caaaatttta ggattttttt ttttcttca    2940 ttacagattc gtcttttttt tttttcttta taaaagccgt aacccagtca gacaaattca    3000
ccttcactta ggcccctgtt ctggtataca tttactgtga gcttttgcct gcctgtgcta    3060
ttttacttgt aaagctagag cacccaagct tctgccttct ggaatataga gaaatagttt    3120
caccctgcac taccctgttc tgtagttatt ctgatgatag ccagtgaggt tcttaaagtt    3180
tgcagtattc tcccctgatt ggaatggttg agtgagggta agggaaagaa tatcttattt    3240
cttttatgat tggtgcaaat tggctaaagt gcattttaa atttcctcta cttaatttgt     3300
ttttcagaga taaggaaaaa tattttgcac agatttactc cactatggaa aagggatgct    3360
gtaggttgaa ccattatagc ctcagattcg atcttttcct aactaaaaat attaaagcct    3420
catgtgtgaa ataaatttt aaaaagattt atctggattt agaaatttt agatcaacag      3480 atacctctca gtgtgtttgc taattaataa aaatcagttt cttacaaata agtttgtaa     3540 gaaaatgttc attttaagtg atagatagtg gagaaaattt atcacctaaa atatacccat    3600
cagtataagg caagcaaaag tcttaacatg gcagccattc tgcctttgcc gtggccctgt    3660
cctgtttagt tcttagtggg ttaatttttg tactttttgca gaagaaactt cagcaagcta   3720
gaactggaag gtactttaat ttttcatata tatttgtttt ttttttttta atgaaggctc    3780
atttacttga aatgtaaaaa ctttcactga atacaaatag aaaagtgat gtgttttata   3840 tcatattgct ttttgtccat ctttgtggtt tagtttattt actcacttca tgtttttcac    3900
ctataaaatt gtcaagctag caaaaaaact cttgtttttt taattgggag agaagagacc    3960
tgccagatta tcagacctct tcatgttaaa agaccatctc ctgtaaaact gacctagtgg    4020
acaagctgaa tttgaaatag actgtgaagt aagctgtaac ttgtcatttt aattttgttt    4080
aacacggtta ctgacttaga tgatgtatta ataccaaga taaagaaaaa tgcacctaaa    4140
atctaattag aattctctgg gtcaacaagt caaggtggta ttgatctgtg ttaatctgag    4200
taacttattg cctagcctat aaataaattc caaaatatcc aattcatttc tcttgaaat     4260 ggtgcttgtt ttgttttctt tccattacac aattagactc ctacagttta aaacaaactt    4320
taaaccacta tcttgcactg ctaacttttt tctaccttg taaatagaaa catttctgca     4380
taaaagtcat acatatgaag caagggctga atcataatca caaggcttaa ttttgataaa    4440
cgaatccagt gacctaagga ttttctgcaa aatttgactg ggagttgtga taggtggtat    4500 ttttgttat tttcttcctc ttactcctta ggataaaggt aagttgactt gaacaacttt     4560
cttttgcact gggaaaataa gcaaatgttt aaatgcttca aaaaaatttt caattaaact    4620
caaatattaa atatctataa cttataaaca ccaactttca atgtaataaa tgtatcctaa    4680
tcttatgtat gttaactgg attacataga ttttatctt tgttaaaat gtgtataccc      4740 cgtggaccaa cataatatta aagtatgtat atattatata aatatatatg tatatgtgct    4800
cgcttgtgta ggatgaatgt cttagagtcg tttgtggtat tttatgttgt tgactctggc    4860
tccagggcct gtgcttgaaa aggacagata agtattgccc agagctaagt ggcactactt    4920
acaaagtttt aaatgtcttc tacatactga ttcatgttta tttgagctct ctttatagaa    4980
```

| | | |
|---|---|---|
| ttttctctta aagtttcaaa cctctaagtt gtagcctgta attatgagaa cagtaaactt | 5040 | |
| taagtaataa taaagaatcc catccatata tccaatttgc aattgagttt tgcatggttc | 5100 | |
| tctgattatg tccatgctgt gtccaaggag gagtaggtac atacaatcag cacagattaa | 5160 | |
| tatatgtaaa gggtttggga cagcacctgg tatagaataa ataataaatg taaactatta | 5220 | |

<210> SEQ ID NO 2
<211> LENGTH: 2486
<212> TYPE: DNA
<213> ORGANISM: Homo sapiens

<400> SEQUENCE: 2

| | | |
|---|---|---|
| gagatttgat tcccttggcg ggcggaagcg gccacaaccc ggcgatcgaa aagattctta | 60 | |
| ggaacgccgt accagccgcg tctctcagga cagcaggccc ctgtccttct gtcgggcgcc | 120 | |
| gctcagccgt gccctccgcc cctcaggttc tttttctaat tccaaataaa cttgcaagag | 180 | |
| gactatgaaa gattatgatg aacttctcaa atattatgaa ttacatgaaa ctattgggac | 240 | |
| aggtggcttt gcaaaggtca aacttgcctg ccatatcctt actggagaga tggtagctat | 300 | |
| aaaaatcatg gataaaaaca cactagggag tgatttgccc cggatcaaaa cggagattga | 360 | |
| ggccttgaag aacctgagac atcagcatat atgtcaactc taccatgtgc tagagacagc | 420 | |
| caacaaaata ttcatggttc ttgagtactg ccctggagga gagctgtttg actatataat | 480 | |
| ttcccaggat cgcctgtcag aagaggagac ccgggttgtc ttccgtcaga tagtatctgc | 540 | |
| tgttgcttat gtgcacagcc agggctatgc tcacagggac ctcaagccag aaaatttgct | 600 | |
| gtttgatgaa tatcataaat taaagctgat tgactttggt ctctgtgcaa acccaagggg | 660 | |
| taacaaggat taccatctac agacatgctg tgggagtctg gcttatgcag cacctgagtt | 720 | |
| aatacaaggc aaatcatatc ttggatcaga ggcagatgtt tggagcatgg gcatactgtt | 780 | |
| atatgttctt atgtgtggat ttctaccatt tgatgatgat aatgtaatgg ctttatacaa | 840 | |
| gaagattatg agaggaaaat atgatgttcc caagtggctc tctcccagta gcattctgct | 900 | |
| tcttcaacaa atgctgcagg tggacccaaa gaaacggatt tctatgaaaa atctattgaa | 960 | |
| ccatccctgg atcatgcaag attacaacta tcctgttgag tggcaaagca agaatccttt | 1020 | |
| tattcacctc gatgatgatt gcgtaacaga actttctgta catcacagaa acaacaggca | 1080 | |
| aacaatggag gatttaattt cactgtggca gtatgatcac ctcacggcta cctatcttct | 1140 | |
| gcttctagcc aagaaggctc ggggaaaacc agttcgttta aggctttctt ctttctcctg | 1200 | |
| tggacaagcc agtgctaccc cattcacaga catcaagtca ataattgga gtctggaaga | 1260 | |
| tgtgaccgca agtgataaaa attatgtggc gggattaata gactatgatt ggtgtgaaga | 1320 | |
| tgatttatca acaggtgctg ctactccccg aacatcacag tttaccaagt actggacaga | 1380 | |
| atcaaatggg gtggaatcta atcattaac tccagcctta tgcagaacac ctgcaaataa | 1440 | |
| attaaagaac aaagaaaatg tatatactcc taagtctgct gtaaagaatg aagagtactt | 1500 | |
| tatgtttcct gagccaaaga ctccagttaa taagaaccag cataagagag aaatactcac | 1560 | |
| tacgccaaat cgttacacta caccctcaaa agctagaaac cagtgcctga agaaactcc | 1620 | |
| aattaaaata ccagtaaatt caacaggaac agacaagtta atgacaggtg tcattagccc | 1680 | |
| tgagaggcgg tgccgctcag tggaattgga tctcaaccaa gcacatatgg aggagactcc | 1740 | |
| aaaaagaaag ggagccaaag tgtttgggag ccttgaaagg gggttggata aggttatcac | 1800 | |
| tgtgctcacc aggagcaaaa ggaagggttc tgccagagac gggcccagaa gactaaagct | 1860 | |

-continued

| | | | | |
|---|---|---|---|---|
| tcactataac | gtgactacaa | ctagattagt | gaatccagat | caactgttga | atgaaataat | 1920 |
| gtctattctt | ccaaagaagc | atgttgactt | tgtacaaaag | ggttatacac | tgaagtgtca | 1980 |
| aacacagtca | gattttggga | aagtgacaat | gcaatttgaa | ttagaagtgt | gccagcttca | 2040 |
| aaaacccgat | gtggtgggta | tcaggaggca | gcggcttaag | ggcgatgcct | gggtttacaa | 2100 |
| aagattagtg | gaagacatcc | tatctagctg | caaggtataa | ttgatggatt | cttccatcct | 2160 |
| gccggatgag | tgtgggtgtg | atacagccta | cataaagact | gttatgatcg | ctttgatttt | 2220 |
| aaagttcatt | ggaactacca | acttgtttct | aaagagctat | cttaagacca | atatctcttt | 2280 |
| gttttttaaac | aaaagatatt | attttgtgta | tgaatctaaa | tcaagcccat | ctgtcattat | 2340 |
| gttactgtct | tttttaatca | tgtggttttg | tatattaata | attgttgact | ttcttagatt | 2400 |
| cacttccata | tgtgaatgta | agctcttaac | tatgtctctt | tgtaatgtgt | aatttctttc | 2460 |
| tgaaataaaa | ccatttgtga | atatag | | | | 2486 |

<210> SEQ ID NO 3
<211> LENGTH: 1989
<212> TYPE: DNA
<213> ORGANISM: Homo sapiens

<400> SEQUENCE: 3

| | | | | | | |
|---|---|---|---|---|---|---|
| gcggaatggg | gcgggacttc | cagtaggagg | cggcaagttt | gaaaagtgat | gacggttgac | 60 |
| gtttgctgat | ttttgacttt | gcttgtagct | gctccccgaa | ctcgccgtct | tcctgtcggc | 120 |
| ggccggcact | gtaggtgagc | gcgagaggac | ggaggaagga | agcctgcaga | cagacgcctt | 180 |
| ctccatccca | aggcgcgggc | aggtgccggg | acgctgggcc | tggcggtgtt | ttcgtcgtgc | 240 |
| tcagcggtgg | gaggaggcgg | aagaaaccag | agcctgggag | attaacagga | aacttccaag | 300 |
| atggaaactt | tgtctttccc | cagatataat | gtagctgaga | ttgtgattca | tattcgcaat | 360 |
| aagatcttaa | caggagctga | tggtaaaaac | ctcaccaaga | atgatcttta | tccaaatcca | 420 |
| aagcctgaag | tcttgcacat | gatctacatg | agagccttac | aaatagtata | tggaattcga | 480 |
| ctggaacatt | tttacatgat | gccagtgaac | tctgaagtca | tgtatccaca | tttaatggaa | 540 |
| ggcttcttac | cattcagcaa | tttagttact | catctggact | cattttttgcc | tatctgccgg | 600 |
| gtgaatgact | ttgagactgc | tgatattcta | tgtccaaaag | caaaacggac | aagtcggttt | 660 |
| ttaagtggca | ttatcaactt | tattcacttc | agagaagcat | gccgtgaaac | gtatatggaa | 720 |
| tttctttggc | aatataaatc | ctctgcggac | aaaatgcaac | agttaaacgc | cgcacaccag | 780 |
| gaggcattaa | tgaaactgga | gagacttgat | tctgttccag | ttgaagagca | agaagagttc | 840 |
| aagcagcttt | cagatggaat | tcaggagcta | caacaatcac | taaatcagga | ttttcatcaa | 900 |
| aaaacgatag | tgctgcaaga | gggaaattcc | caaaagaagt | caaatatttc | agagaaaacc | 960 |
| aagcgtttga | atgaactaaa | attgtcggtg | gtttctttga | agaaatacac | agagagtttg | 1020 |
| aaaacaaaaa | ttgtggattc | tccagagaag | ttaaagaatt | ataaagaaaa | aatgaaagat | 1080 |
| acggtccaga | agcttaaaaa | tgccagacaa | gaagtggtgg | agaaatatga | aatctatgga | 1140 |
| gactcagttg | actgcctgcc | ttcatgtcag | ttggaagtgc | agttatatca | aaagaaaata | 1200 |
| caggaccttt | cagataatag | ggaaaaatta | gccagtatct | taaggagag | cctgaacttg | 1260 |
| gaggaccaaa | ttgagagtga | tgagtcagaa | ctgaagaaat | tgaagactga | agaaaattcg | 1320 |
| ttcaaaagac | tgatgattgt | gaagaaggaa | aaacttgcca | cagcacaatt | caaaataaat | 1380 |
| aagaagcatg | aagatgttaa | gcaatacaaa | cgcacagtaa | ttgaggattg | caataaagtt | 1440 |
| caagaaaaaa | gaggtgctgt | ctatgaacga | gtaaccacaa | ttaatcaaga | aatccaaaaa | 1500 |

```
attaaacttg gaattcaaca actaaaagat gctgctgaaa gggagaaact gaagtcccag    1560
gaaatatttc taaacttgaa aactgctttg gagaaatacc acgacggtat tgaaaaggca    1620
gcagaggact cctatgctaa gatagatgag aagacagctg aactgaagag gaagatgttc    1680
aaaatgtcaa cctgattaac aaaattacat gtcttttgt aaatggcttg ccatctttta     1740
attttctatt tagaaagaaa agttgaagcg aatggaagta tcagaagtac caaataatgt    1800
tggcttcatc agtttttata cactctcata agtagttaat aagatgaatt taatgtaggc    1860
ttttattaat ttataattaa ataaacttgt gcagctattc atgtctctac tctgcccctt    1920
gttgtaaata gtttgagtaa aacaaaacta gttacctttg aaatatatat attttttct     1980 gttactatc                                                          1989

<210> SEQ ID NO 4
<211> LENGTH: 1148
<212> TYPE: DNA
<213> ORGANISM: Homo sapiens

<400> SEQUENCE: 4
gcgccgagac ccgctcctgc agtattagtt cttgcagctg gtggtggcgg ctgaggcggc      60
atggatctca gcgagctgga gagagacaat acaggccgct gtcgcctgag ttcgcctgtg     120
cccgcggtgt gccgcaagga gccttgcgtc ctgggcgtcg atgaggcggg caggggcccc     180
gtgctgggcc ccatggtcta cgccatctgt tattgtcccc tgcctcgcct ggcagatctg     240
gaggcgctga aagtggcaga ctcaaagacc ctattggaga gcgagcggga aaggctgttt     300
gcgaaaatgg aggacacgga ctttgtcggc tgggcgctgg atgtgctgtc tccaaacctc     360
atctctacca gcatgcttgg gcgggtcaaa tacaacctga actccctgtc acatgataca     420
gccactgggc ttatacagta tgcattggac cagggcgtga acgtcaccca ggtattcgtg     480
gacaccgtag ggatgccaga gacataccag gcgcggctgc agcaaagttt tcccgggatt     540
gaggtgacgg tcaaggccaa agcagatgcc ctctacccgg tggttagtgc tgccagcatc     600
tgtgccaagg tggcccggga ccaggccgtg aagaaatggc agttcgtgga gaaactgcag     660
gacttggata ctgattatgg ctcaggctac cccaatgatc ccaagacaaa agcgtggttg     720
aaggagcacg tggagcctgt gttcggcttc ccccagtttg tccggttcag ctggcgcacg     780
gcccagacca tcctggagaa agaggcggaa gatgttatat gggaggactc agcatccgag     840
aatcaggagg gactcaggaa gatcacatcc tacttcctca atgaagggtc ccaagcccgt     900
ccccgttctt cccaccgata tttcctggaa cgcggcctgg agtcagcaac cagcctctag     960
cagctgcctc tacgcgctct acctgcttcc ccaacccaga cattaaaatt gtttaaggag    1020
aaccacacgt aggggatgta cttttgggac agaagcaagg tggagtgtg ctctgcagcc     1080 gggtccagct acttcctttt ggaaccttaa atagaatggg tgttggttga ttaattttat    1140
ttaaaaaa                                                            1148

<210> SEQ ID NO 5
<211> LENGTH: 510
<212> TYPE: DNA
<213> ORGANISM: Homo sapiens

<400> SEQUENCE: 5
tgaggctgcc ttataaagca ccaagaggct gccagtggga catttctcg gccctgccag       60 ccccaggag gaaggtgggt ctgaatctag caccatgacg gaactagaga cagccatggg      120
```

| | |
|---|---|
| catgatcata gacgtctttt cccgatattc gggcagcgag ggcagcacgc agaccctgac | 180 |
| caagggggag ctcaaggtgc tgatggagaa ggagctacca ggcttcctgc agagtggaaa | 240 |
| agacaaggat gccgtggata aattgctcaa ggacctggac gccaatggag atgcccaggt | 300 |
| ggacttcagt gagttcatcg tgttcgtggc tgcaatcacg tctgcctgtc acaagtactt | 360 |
| tgagaaggca ggactcaaat gatgccctgg agatgtcaca gattcctggc agagccatgg | 420 |
| tcccaggctt cccaaaagtg tttgttggca attattcccc taggctgagc ctgctcatgt | 480 |
| acctctgatt aataaatgct tatgaaatga | 510 |

<210> SEQ ID NO 6
<211> LENGTH: 1323
<212> TYPE: DNA
<213> ORGANISM: Homo sapiens

<400> SEQUENCE: 6

| | |
|---|---|
| gcggggtcg cgctgcacag cctgcggcgc agcggaggcg gaccgcagtc gagtctgcag | 60 |
| agtgttgggt ctgtagccag caaattactt catcatctag attatccatt cagttgatcc | 120 |
| taattagcaa ggataacaag gtaacacaag gcttacttat attcacccaa caaaagtgtc | 180 |
| tctgtggagc cacttcccag tgaactacat actgagatag ggttcctgg atgagaagga | 240 |
| ccaaggacag aaccgagaag agtttagggg caggttatgc gagatggaaa tggcgcagat | 300 |
| aacgagggga aggatttgag ggctcaaacg taggcgtctg tgtttcgcaa agttggaga | 360 |
| cgttctaggc tgcctctcgt tgcctccatc tcgctctgcg cgggttttgg aggacattag | 420 |
| cattctttct tgtatctccg ttgattccag aatcgtccgc actaaagtcc cctgcagcgt | 480 |
| gaccatgtcg agaccccgga gaggctggc tgggacttct ggttcagaca agggactatc | 540 |
| aggaaaacgc accaaaactg agaactcagg tgaggcatta gctaaagtgg aggactccaa | 600 |
| ccctcagaag acttcagcca ctaaaaactg tttgaagaat ctaagcagcc actggctgat | 660 |
| gaagtcagag ccagagagcc gcctagaaa aggtgtagat gtgaagttca gcattgagga | 720 |
| tctcaaagca cagcccaaac agacaacatg ctgggatggt gttcgtaact accaggctcg | 780 |
| gaacttcctt agagccatga agctgggaga agaagccttc ttctaccata gcaactgcaa | 840 |
| agagccaggc atcgcaggac tcatgaagat cgtgaaagag gcttacccag accacacaca | 900 |
| gtttgagaaa acaatccccc attatgaccc atctagcaaa gaggacaacc ctaagtggtc | 960 |
| catggtggat gtacagtttg ttcggatgat gaaacgtttc attcccctgg ctgagctcaa | 1020 |
| atcctatcat caagctcaca agctactggt ggcccctta aaaaatatgg ttctcttcac | 1080 |
| tcgccagaga ttatcaatcc agcccctgac ccaggaagag tttgatttg ttttgagcct | 1140 |
| ggaggaaaag gaaccaagtt aactgagata ctgctgctgg aatgggcgag acattgctgc | 1200 |
| aaagaagtca agcttttttc agacaaaagg tgtgaggggg cttgcttggt atgcttacct | 1260 |
| gggcttgtgt acctcagtgg tttttgtgta cttttttcaa taaaatatca agttgaaga | 1320 |
| aaa | 1323 |

<210> SEQ ID NO 7
<211> LENGTH: 1675
<212> TYPE: DNA
<213> ORGANISM: Homo sapiens

<400> SEQUENCE: 7

| | |
|---|---|
| agcttgcccg gcatcactcg cggcattgga gtcaagatgg aggagtacgc gcgagagcct | 60 |
| tgcccatggc gaattgtgga tgactgtggt ggggccttta cgatgggtac cattggtggt | 120 |

-continued

| | |
|---|---|
| ggtatctttc aagcaatcaa aggttttcgc aattctccag tgggagtaaa ccacagacta | 180 |
| cgagggagtt tgacagctat taaaaccagg gctccacagt taggaggtag ctttgcagtt | 240 |
| tggggagggc tgttttccat gattgactgt agtatggttc aagtcagagg aaaggaagat | 300 |
| ccctggaact ccatcacaag tggtgcctta acgggagcca tactggcagc aagaaatgga | 360 |
| ccagtggcca tggttgggtc agccgcaatg ggtggcattc tcctagcttt aattgaagga | 420 |
| gctggtatct tgttgacaag atttgcctct gcacagtttc ccaatggtcc tcagtttgca | 480 |
| gaagacccct cccagttgcc ttcaactcag ttaccttcct caccttttgg agactatcga | 540 |
| caatatcagt aggacttctt tcctaggatt tcttttaacag aacgagttgt ggttcgagaa | 600 |
| ggatttcaga agatcaagtt acagtctgtt tttaaaacca taggtgggac agctatggcc | 660 |
| aataggctat aaagagacat ttagcacttt tttctattta aaggaacaag cggggaaggg | 720 |
| tgctaaaaga taatacgttt atttattcac acttgaattg catttgtgat caaaataaat | 780 |
| gtttaaatcg ctaaaggaaa atacagtaag tgcttgaaag atgaaggacc aaaaggccaa | 840 |
| aaaacagtga aatatgatca tcatctcctt gcggacttct ctgcctggtt ttgtgtgttc | 900 |
| tgttattcaa acaataaaaa gctggtggaa cttactcttt cttttaagat aagttgtaga | 960 |
| cttcgatgtt tcatgctcat gtacttcaaa taatgcatgt tttatagtta gtccctcatc | 1020 |
| acttgaagtg acttctgaga attatgcaga gtcaacatgg atcatttcac agtgagatgc | 1080 |
| tttatggatt gaaggatatg gtaaaatgtt tatagtttac tttgaaagta aaatatacta | 1140 |
| tgtcttggtt ttgaggatat tggatacaaa actctcttcc tttagggcta ctgagtcttg | 1200 |
| attcctgatc atcagaaatt tcaccagaaa caacttgctt ccaatatacc caattctata | 1260 |
| tgaagaattc atggagagtg tactggcact ggaagagttt agtgtttctt gtatgcttga | 1320 |
| aaataaagta tgtactgttt tgaatgtgtt ccaagtcctc tgcataaacg atgtattttg | 1380 |
| gggtctggtt gggcctggaa aatggatgag cacttcagaa caggtcattt tcctgatatt | 1440 |
| ggaagtgaca tgtggcccta taggaggcat gatgttagtt aattacacat ttgcctacat | 1500 |
| ctgtgggaaa tggagaacaa agccatgtgg gtactgtaaa cacacgttta tcttttggcc | 1560 |
| caatgccata catatggtag gcatttaatt actgattgtg tttggataat ttgggaattt | 1620 |
| tcgactgtgg taaaatatac ataaaataat acttattaaa aaaaaaaaa aaaaa | 1675 |

<210> SEQ ID NO 8
<211> LENGTH: 8626
<212> TYPE: DNA
<213> ORGANISM: Homo sapiens

<400> SEQUENCE: 8

| | |
|---|---|
| acgacggggg aggtgctgta cgtccaagat ggcggcgccc tgtaggctgg agggactgtg | 60 |
| aggtaaacag ctgaggggga ggagacggtg gtgaccatga aagacaccag gttgacagca | 120 |
| ctggaaactg aagtaccagt tgtcgctaga acagtttggt agtggcccca atgaagaacc | 180 |
| ttcagaacct gtagcacacg tcctggagcc agcacagcgc cttcgagcga gagaatggcc | 240 |
| caacaagcaa atgtcgggga gcttcttgcc atgctggact cccccatgct gggtgtgcgg | 300 |
| gacgacgtga cagctgtctt taagagaaac ctcaattctg accgtggccc tatgcttgta | 360 |
| aacaccttgg tggattatta cctggaaacc agctctcagc cggcattgca catcctgacc | 420 |
| acccttgcaag agccacatga caagcacctc ttggacagga ttaacgaata tgtgggcaaa | 480 |
| gccgccactc gtttatccat cctctcgtta ctgggtcatg tcataagact gcagccatct | 540 |

```
tggaagcata agctctctca agcacctctt ttgccttctt tactaaaatg tctcaagatg      600
gacactgacg tcgttgtcct cacaacaggc gtcttggtgt tgataaccat gctaccaatg      660
attccacagt ctgggaaaca gcatcttctt gatttctttg acattttggg ccgtctgtca      720
tcatggtgcc tgaagaaacc aggccacgtg gcggaagtct atctcgtcca tctccatgcc      780
agtgtgtacg cactctttca tcgcctttat ggaatgtacc cttgcaactt cgtctccttt      840
ttgcgttctc attacagtat gaaagaaaac ctggagactt tgaagaagt ggtcaagcca       900 atgatggagc atgtgcgaat tcatccggaa ttagtgactg gatccaagga ccatgaactg      960
gaccctcgaa ggtggaagag attagaaact catgatgttg tgatcgagtg tgccaaaatc     1020
tctctggatc ccacagaagc ctcatatgaa gatggctatt ctgtgtctca ccaaatctca     1080
gcccgctttc ctcatcgttc agccgatgtc accaccagcc cttatgctga cacacagaat     1140
agctatgggt gtgctacttc tacccccttac tccacgtctc ggctgatgtt gttaaatatg    1200
ccagggcagc tacctcagac tctgagttcc ccatcgacac ggctgataac tgaaccacca     1260
caagctactc tttggagccc atctatggtt tgtggtatga ccactcctcc aacttctcct     1320
ggaaatgtcc cacctgatct gtcacaccct tacagtaaag tctttggtac aactgcaggt     1380
ggaaaaggaa ctcctctggg aaccccagca acctctcctc ctccagcccc actctgtcat     1440
tcggatgact acgtgcacat ttcactcccc caggccacag tcacaccccc caggaaggaa     1500
gagagaatgg attctgcaag accatgtcta cacagacaac accatcttct gaatgacaga     1560
ggatcagaag agccacctgg cagcaaaggt tctgtcactc taagtgatct tccagggttt     1620
ttaggtgatc tggcctctga agaagatagt attgaaaaag ataaagaaga agctgcaata     1680
tctagagaac tttctgagat caccacagca gaggcagagc ctgtggttcc tcgaggaggc     1740
tttgactctc cctttaccg agacagtctc ccaggttctc agcggaagac ccactcggca     1800
gcctccagtt ctcagggcgc cagcgtgaac cctgagcctt acactcctc cctggacaag      1860 cttgggcctg acacaccaaa gcaagccttt actcccatag acctgccctg cggcagtgct     1920
gatgaaagcc ctgcgggaga cagggaatgc cagacttctt tggagaccag tatcttcact     1980
cccagtcctt gtaaaattcc acctccgacg agagtgggct ttggaagcgg gcagcctccc     2040
ccgtatgatc atcttttga ggtggcattg ccaaagacag cccatcattt tgtcatcagg      2100
aagactgagg agctgttaaa gaaagcaaaa ggaaacacag aggaagatgg tgtgccctct     2160
acctccccaa tggaagtgct ggacagactg atacagcagg gagcagacgc gcacagcaag     2220
gagctgaaca agttgccttt acccagcaag tctgtcgact ggaccacctt ggaggctct      2280 cctccttcag atgagatccg caccctccga gaccagttgc ttttactgca caaccagtta     2340
ctctatgagc gttttaagag gcagcagcat gccctccgga caggcggct cctccgcaag     2400 gtgatcaaag cagcagctct ggaggaacat aatgctgcca tgaaagatca gttgaagtta     2460
caagagaagg acatccagat gtggaaggtt agtctgcaga aagaacaagc tagatacaat     2520
cagctccagg agcagcgtga cactatggta accaagctcc acagccagat cagacagctg     2580
cagcatgacc gagaggaatt ctacaaccag agccaggaat tacagacgaa gctggaggac     2640
tgcaggaaca tgattgcgga gctgcggata gaactgaaga aggccaacaa caaggtgtgt     2700
cacactgagc tgctgctcag tcaggttttcc caaaagctct caaacagtga gtcggtccag     2760
cagcagatgg agttcttgaa caggcagctg ttggttcttg ggaggtcaa cgagctctat      2820 ttggaacaac tgcagaacaa gcactcagat accacaaagg aagtagaaat gatgaaagcc     2880
gcctatcgga aagagctaga aaaaaacaga agccatgttc tccagcagac tcagaggctt     2940
```

```
gatacctccc aaaaacggat tttggaactg aatctcacc  tggccaagaa agaccacctt   3000
cttttggaac agaagaaata tctagaggat gtcaaactcc aggcaagagg acagctgcag   3060
gccgcagaga gcaggtatga ggctcagaaa aggataaccc aggtgtttga attggagatc   3120
ttagatttat atggcaggtt ggagaaagat ggcctcctga aaaaacttga agaagaaaaa   3180
gcagaagcag ctgaagcagc agaagaaagg cttgactgtt gtaatgacgg gtgctcagat   3240
tccatggtag ggcacaatga agaggcatct ggccacaacg gtgagaccaa gaccccagg    3300 cccagcagcg cccggggcag tagtggaagc agaggtggtg gaggcagcag cagcagcagc   3360
agcgagcttt ctaccccaga gaaaccccca caccagaggg caggcccatt cagcagtcgg   3420
tgggagacga ctatgggaga agcgtctgcc agcatcccca ccactgtggg ctcacttccc   3480
agttcaaaaa gcttcctggg tatgaaggct cgagagttat ttcgtaataa gagcgagagc   3540
cagtgtgatg aggacggcat gaccagtagc cttttctgaga gcctaaagac agaactgggc   3600
aaagacttgg gtgtggaagc caagattccc ctgaacctag atggccctca cccgtctccc   3660
ccgaccccgg acagtgttgg acagctacat atcatggact acaatgagac tcatcatgaa   3720
cacagctaag gaatgatggt caatcagtgt taacttgcat attgttggca cagaacagga   3780
ggtgtgaatg cacgtttcaa agctttcctg tttccagggt ctgagtgcaa gttcatgtgt   3840
ggaaatggga cggaggtcct ttggacagct gactgaatgc agaacggttt ttggatctgg   3900
cattgaaatg cctcttgacc ttcccctcca cccgccctaa ccccctctca tttacctcgc   3960
agtgtgttct aatccaaggg ccagttggtg ttcctcagta gctttacttt cttcctttcc   4020
cccccaaatg gttgcgtcct ttgaacctgt gcaatatgag gccaaattta atctttgagt   4080
ctaacacacc actttctgct ttcccgaagt tcagataact gggttggctc tcaattagac   4140
caggtagttt gttgcattgc aggtaagtct ggttttgtcc cttccaggag acatagcct   4200 gcaaagctgg ttgtctttac atgaaagcgt ttacatgaga cttccgact  gctttttga   4260 ttctgaagtt cagcatctaa agcagcaggt ctagaagaac aacggtttat tcatacttgc   4320
attcttttgg cagttctgat aagcttccta gaaagttctg tgtaaacaga agcctgtttc   4380
agaaatctgg agctggcact gtggagacca cacccctttt gggaaagctc ttgtctcttc   4440
ttcccccact acctcttatt tatttggtgt ttgcttgaat gctggtacta ttgtgaccac   4500
aggctggtgt gtaggtggta aaacctgttc tccataggag ggaaggagca gtcactggga   4560
gaggttaccc gagaagcact tgagcatgag gaactgcacc tttaggccat ctcagcttgc   4620
tgggcctttt gttaaaccct tctgtctact ggcctccctt tgtgtgcata cgcctcttgt   4680
tcatgtcagc ttatatgtga cactgcagca gaaaggctct gaaggtccaa agagtttctg   4740
caaagtgtat gtgaccatca tttcccaggc cattagggtt gcctcactgt agcaggttct   4800
aggctaccag aagaggggca gcttttttcat accaattcca actttcaggg gctgactctc   4860
cagggagctg atgtcatcac actctccatg ttagtaatgg cagagcagtc taaacagagt   4920
ccgggagaat gctggcaaag gctggctgtg tatacccact aggctgcccc acgtgctccc   4980
gagagatgac actagtcaga aaattggcag tggcagagaa tccaaactca acaagtgctc   5040
ctgaaagaaa cgctagaagc ctaagaactg tggtctggtg ttccagctga ggcaggggga   5100
tttggtagga aggagccagt gaacttggct ttcctgtttc tatctttcat taaaaagaat   5160
agaaggattc agtcataaag aggtaaaaaa ctgtcacggt acgaaatctt agtgcccacg   5220
gaggcctcga gcagagagaa tgaaagtctt tttttttttt tttttttttt agcatggcaa   5280
```

```
taaatattct agcatccctc actaaagggg actagacagt tagagactct gtcaccctag      5340
ctataccagc agaaaacctg ttcaggcagg cttcctgggt gtgactgatt cccagcctgt      5400
ggcagggcgt ggtcccaact actcagccta gcacaggctg gcagttggta ctgaattgtc      5460
agatgtggag tattagtgac accacacatt taattcagct ttgtccaaag gaaagcttaa      5520
aacccaatac agtctagttt cctggttccg ttttagaaaa ggaaaacgtg aacaaactta      5580
gaaagggaag gaaatcccat cagtgaatcc tgaaactggt tttaagtgct ttccttctcc      5640
tcatgcccaa gagatctgtg ccatagaaca agataccagg cacttaaagc cttttcctga      5700
attggaaagg aaaagaggcc caagtgcaaa agaaaaaaca ttttagaaac ggacagctta      5760
taaaaataaa gggaagaaag gaggcagcat ggagagaggc ctgtgctaga agctccatgg      5820
acgtgtctgc acagggtcct cagctcatcc atgcggcctg ggtgtccttt tactcagctt      5880
tataacaaat gtggctccaa gctcaggtgc ctttgagttc taggaggctg tgggttttat      5940
tcaactacgg ttgggagaat gagacctgga gtcatgttga aggtgcccaa cctaaaaatg      6000
taggctttca tgttgcaaag aactccagag tcagtagtta ggtttggttt ggttttggac      6060
atgataaacc tgccaagagt caacaggtca cttgatcatg ctgcagtggg tagttctaag      6120
gatgaaaagg tgacagtatt actctcgaga ggcaattcag tcctgggcaa aggtattagt      6180
acaataagcg ttaagggcag agtctacctt gaaccaatt aagcagcttg gtattcataa       6240
atattgggat tggatggcct ccatccagaa atcactatgg gtgagcatac ctgtctcagc      6300
tgtttggcca atgtgcataa cctactcgga tccccacctg acactaacca gagtcagcac      6360
aggcccgag gagcccgaag tctgctgctg tgcagcatgg aattccttta aaaggtgca       6420
ctacagttt agcggggagg gggataggaa gacgcagagc aaatgagctc cggagtccct       6480
gcaggtgaat aaacacacag atctgcatct gatagaactt tgatggattt tcaaaaagcc      6540
gttgacaagg ctctgctata cagtctataa aaattgttat tatgggattg aagaaacac       6600
gtggtcatga atagaaaaaa aacaaaccca aaggtaggaa ggtcaaggtc atttcttaga     6660
tggagaagtt gtgaaagatg tccttggaga tgagttttag gaccagcatt actaaggcag     6720
gtgggcagac agtgacctct ctaggtgtgt ccacagagtt tttcaggaga gaaaactgcc     6780
tgacctttgg gactaagctg cggaatcttc ttactaagct tgaagagtgg agaggcgaga     6840
ggtgagctac tttgtgagcc aaagcttatg tgacatggtt ggggaaacag tccaaactgt     6900
tctgagaagg tgaactgtta cgacccagga caattagaaa aattcaccca ccatgccgca     6960
cattactggg taaagcagg gcagcaggga acaaaactcc agactcttgg gccgtcccca      7020
tttgcaacag cacacatagt ttctggtata tttgttggga agataaaac tctagcagtt      7080
gttgagggga ggatgtataa aatggtcatg gggatgaaag gatctctgag accacagagg     7140
ctcagactca ctgttaagaa tagaaaactg ggtatgcgtt tcatgtagcc agcagaactg     7200
aagtgtgctg tgacaagcca atgtgaattt ctaccaaata gtagagcata ccacttgaag     7260
aaggaaagaa ccgaagagca aacaaaagtt ctgcgtaatg agactcacct tttctcgctg     7320
aaagcactaa gaggtgggag gaggcctgca caggctggag gagggtttgg gcagagcgaa     7380
gacccggcca ggaccttggt gagatggggt gccgcccacc tcctgcggat actcttggag     7440
agttgttccc ccaggggct ctgccccacc tggagaagga agctgcctgg tgtggagtga      7500
ctcaaatcag tatacctatc tgctgcacct tcactctcca gggtacatgc tttaaaaccg     7560
acccgcaaca agtattggaa aaatgtatcc agtctgaaga tgtttgtgta tctgtttaca     7620
tccagagttc tgtgacacat gccccccaga ttgctgcaaa gatcccaagg cattgattgc     7680
```

| | |
|---|---|
| acttgattaa gcttttgtct gtaggtgaaa gaacaagttt aggtcgagga ctggcccta | 7740 |
| ggctgctgct gtgacccttg tcccatgtgg cttgtttgcc tgtccgggac tcttcgatgt | 7800 |
| gcccagggga gcgtgttcct gtctcttcca tgccgtcctg cagtccttat ctgctcgcct | 7860 |
| gagggaagag tagctgtagc tacaagggaa gcctgcctgg aagagccgag cacctgtgcc | 7920 |
| catggcttct ggtcatgaaa cgagttaatg atggcagagg agcttcctcc ccacttcgca | 7980 |
| gcgccacatt atccatcctc tgagataagt aggctggttt aaccattgga atggaccttt | 8040 |
| cagtggaaac cctgagagtc tgagaacccc cagaccaacc cttccctccc tttccccacc | 8100 |
| tcttacagtg ttttggacag agggtatggt gctgctctgt gtagcaagta ctttggctta | 8160 |
| tgaaagaggc agccacgcat tttgcactag gaagaatcag taatcacttt tcagaagact | 8220 |
| tctatggacc acaaatatat tacggaggaa cagattttgc taagacataa tctagttta | 8280 |
| taactcaatc atgaatgaac catgtgtggc aaacttgcag tttaaagggg tcccatcagt | 8340 |
| gaaagaaact gatttttttt aacgactgc ttttagttaa attgaagaaa gtcagctctt | 8400 |
| gtcaaaaggt ctaaactttc ccgcctcaat cctaaaagca tgtcaacaat ccacatcaga | 8460 |
| tgccataaat atgaactgca ggataaaatg gtacaatctt agtgaatggg aattggaatc | 8520 |
| aaaagagttt gctgtccttc ttagaatgtt ctaaaatgtc aaggcagttg cttgtgttta | 8580 |
| actgtgaaca ataaaaatt tattgttttg cactacaaaa aaaaaa | 8626 |

<210> SEQ ID NO 9
<211> LENGTH: 7777
<212> TYPE: DNA
<213> ORGANISM: Homo sapiens

<400> SEQUENCE: 9

| | |
|---|---|
| agagggaaaa agaacgtcag gagagtgaac gggagcaaat aaaacgctgt ccattctgac | 60 |
| tggaagggcc agagccgtgt ctaagggcgg gggccgggag gtggcccgcg gtggtgtctc | 120 |
| taccaggacg aggcctgggg tatctgaaga ggggatgacg tccaggcgct ttgctaaagg | 180 |
| gaagccagaa gggtatgagt tgctagggtc agagatgggg cttttcggctc gagtcttttcc | 240 |
| ctgcagggca gagagtccga agagcccgag aaggcaggga ggacagtggg cctggtcctt | 300 |
| ccccggccgg cagagggagt cccgagatgg aacgtccagc tctcctctaa cgaaaagcgt | 360 |
| ttgcatggct gtctcgccaa ttctgtacct cccggggctg aggaagagcc gaggtgacta | 420 |
| gaagctagcg acaagtgccg gccacctccg acgccaggcg ccgggcttgg agcccgacgg | 480 |
| gccgaattct cgcgagagcg gccgccgcca tttttccatt gattgcagcg ggctggggga | 540 |
| ggggccgacg acgaaggcgg ctgtggtagc ggcggcggcg gcggcggagc cctgggtcgg | 600 |
| tgtctgcgcg ctggtgtctg aggcccaggc tgaggcctcc gctattgctg gagcgcaggc | 660 |
| ggcggagagg atgactgccg ctgccattct ctcttgagct agcgagccgc cgccacccctc | 720 |
| caccctcccc cggcagggcg gagaggagcg gccgagtca gcgatggtgc ccggcgagga | 780 |
| gaaccaactg gtcccgaaag aggcaccact ggatcatacc agtgacaagt cacttctcga | 840 |
| cgctaatttt gagccaggaa agaagaactt tctgcatttg acagataaag atggtgaaca | 900 |
| acctcaaata ctgctggagg attccagtgc tgggaagac agtgttcatg acaggtttat | 960 |
| aggtccgctt ccaagagaag gttctggggg ttctaccagt gattatgtca gccaaagcta | 1020 |
| ctcctactca tctattttga ataaatcaga aactggatat gtgggactag taaaccaagc | 1080 |
| aatgacttgc tatttgaata gccttttgca aacacttttt atgactcctg aatttaggaa | 1140 |

```
tgcattatat aagtgggaat tgaagaatc tgaagaagat ccagtgacaa gtattccata    1200
ccaacttcaa aggctttttg ttttgttaca aaccagcaaa aagagagcaa ttgaaaccac    1260
agatgttaca aggagctttg gatgggatag tagtgaggct tggcagcagc atgatgtaca    1320
agaactatgc agagtcatgt ttgatgcttt ggaacagaaa tggaagcaaa cagaacaggc    1380
tgatcttata aatgagctat atcaaggcaa gctgaaggac tacgtgagat gtctggaatg    1440
tggttatgag ggctggcgaa tcgacacata tcttgatatt ccattggtca tccgacctta    1500
tgggtccagc caagcatttg ctagtgtgga agaagcattg catgcattta ttcagccaga    1560
gattctggat ggcccaaatc agtattttg tgaacgttgt aagaagaagt gtgatgcacg    1620
gaagggcctt cggttttgc attttcctta tctgctgacc ttacagctga aaagattcga    1680
ttttgattat acaaccatgc ataggattaa actgaatgat cgaatgacat ttcccgagga    1740
actagatatg agtactttta ttgatgttga agatgagaaa tctcctcaga ctgaaagttg    1800
cactgacagt ggagcagaaa atgaaggtag ttgtcacagt gatcagatga gcaacgattt    1860
ctccaatgat gatggtgttg atgaaggaat ctgtcttgaa accaatagtg gaactgaaaa    1920
gatctcaaaa tctggacttg aaaagaattc cttgatctat gaactttct ctgttatggt    1980 tcattctggg agcgctgctg gtggtcatta ttatgcatgt ataaagtcat tcagtgatga    2040
gcagtggtac agcttcaatg atcaacatgt cagcaggata acacaagagg acattaagaa    2100
aacacatggt ggatcttcag gaagcagagg atattattct agtgctttcg caagttccac    2160
aaatgcatat atgctgatct atagactgaa ggatccagcc agaaatgcaa atttctaga    2220 agtggatgaa tacccagaac atattaaaaa cttggtgcag aaagagagag agttggaaga    2280
acaagaaaag agacaacgag aaattgagcg caatacatgc aagataaaat tattctgttt    2340
gcatcctaca aaacaagtaa tgatggaaaa taaattggag gttcataagg ataagacatt    2400
aaaggaagca gtagaaatgg cttataagat gatggattta gaagaggtaa taccccctgga    2460 ttgctgtcgc cttgttaaat atgatgagtt tcatgattat ctagaacggt catatgaagg    2520
agaagaagat acaccaatgg ggcttctact aggtggcgtc aagtcaacat atatgtttga    2580
tctgctgttg gagacgagaa agcctgatca ggttttccaa tcttataaac ctggagaagt    2640
gatggtgaaa gttcatgttg ttgatctaaa ggcagaatct gtagctgctc ctataactgt    2700
tcgtgcttac ttaaatcaga cagttacaga attcaaacaa ctgatttcaa aggccatcca    2760
tttacctgct gaaacaatga gaatagtgct ggaacgctgc tacaatgatt tgcgtcttct    2820
cagtgtctcc agtaaaaaccc tgaaagctga aggattttttt agaagtaaca aggtgtttgt    2880
tgaaagctcc gagactttgg attaccagat ggcctttgca gactctcatt tatggaaact    2940
cctggatcgg catgcaaata caatcagatt atttgttttg ctacctgaac aatccccagt    3000
atcttattcc aaaaggacag cataccagaa agctggaggc gattctggta atgtggatga    3060
tgactgtgaa agagtcaaag gacctgtagg aagcctaaag tctgtggaag ctattctaga    3120
agaaagcact gaaaaactca aaagcttgtc actgcagcaa cagcaggatg gagataatgg    3180
ggacagcagc aaaagtactg agacaagtga ctttgaaaac atcgaatcac ctctcaatga    3240
gagggactct tcagcatcag tggataatag agaacttgaa cagcatattc agacttctga    3300
tccagaaaat tttcagtctg aagaacgatc agactcagat gtgaataatg acaggagtac    3360
aagttcagtg gacagtgata ttcttagctc cagtcatagc agtgatactt tgtgcaatgc    3420
agacaatgct cagatccctt tggctaatgg acttgactct cacagtatca aagtagtag    3480 aagaacgaaa gcaaatgaag ggaaaaaaga aacatgggat acagcagaag aagactctgg    3540
```

```
aactgatagt gaatatgatg agagtggcaa gagtagggga gaaatgcagt acatgtattt    3600
caaagctgaa ccttatgctg cagatgaagg ttctggggaa ggacataaat ggttgatggt    3660
gcatgttgat aaagaattca ctctggcagc tttcaaacaa catttagagc cctttgttgg    3720
agttttgtcc tctcacttca aggtctttcg agtgtatgcc agcaatcaag agtttgagag    3780
cgtccggctg aatgagacac tttcatcatt ttctgatgac aataagatta caattagact    3840
ggggagagca cttaaaaaag gagaatacag agttaaagta taccagcttt tggtcaatga    3900
acaagagcca tgcaagtttc tgctagatgc tgtgtttgct aaaggaatga ctgtacggca    3960
atcaaaagag gaattaattc ctcagctcag ggagcaatgt ggtttagagc tcagtattga    4020
caggtttcgt ctaaggaaaa aaacatggaa gaatcctggc actgtctttt tggattatca    4080
tatttatgaa gaagatatta atatttccag caactgggag gttttccttg aagttcttga    4140
tggggtagag aagatgaagt ccatgtcaca gcttgcagtt ttgtcaagac ggtggaagcc    4200
ttcagagatg aagttggatc ccttccagga ggttgtattg gaaagcagta gtgtggacga    4260
attgcgagag aagcttagtg aaatcagtgg gattcctttg gatgatattg aatttgctaa    4320
gggtagagga acatttccct gtgatatttc tgtccttgat attcatcagg atttagactg    4380
gaatcctaaa gtttctaccc tgaatgtctg gcctctttat atctgtgatg atggtgcggt    4440 catatttat agggataaaa cagaagaatt aatggaattg acagatgagc aaagaaatga    4500
actgatgaaa aaagaaagca gtcgactcca gaagactgga catcgtgtaa catactcacc    4560
tcgtaaagag aaagcactaa aaatatatct ggatggagca ccaaataaag atctgactca    4620
agactgactc tgatagtgta gcattttccc tgggggagtt ttggttttaa ttagatggtt    4680
cactaccact gggtagtgcc attttggccg gacatggttg gggtaaccca gtgacaccag    4740
cactgattgg actgccctac accaatcaga agctcagtgc ccaatgggcc actgttttga    4800
ctcggaatca tgttgtgcac tatagtcaaa tgtactgtaa agtgaaaagg gatgtgcaaa    4860
aaaataaaaa aaacaacaa aaaaagctaa ccttctatta gaaaagggga caggggaatg    4920
agtaaacttc ttttattgcg gacaaatgtg cacatagccg ctagtaaaac tagcctcaaa    4980
caggatgctc atagcttaat aataaaagct gtgcaaaggc catgaatgaa tgaattttct    5040
gtttatttca ctgatgcaca cattacctca ttgacaattc agaagtaaat ccaacgtgtg    5100
ttgactcttg gaaagcagca aaaacaggag ctgaagaaaa gaaattcttg gaaccagccg    5160
taacccagta aggaattgtg aagttgtgtt tttatttgt ttcattttt gcagagtatt    5220 aagaacatta ttctggaaca tcagaacgtt tcccttagac cgatcccagc aggtggcagc    5280
tcagattgct gcagtgttgt aattataact gattgtactt aagttatgga tgtagagaat    5340
atgtttcatt catttattca gcatgtaaat aaaattgatc ctgttgagtt atcataattg    5400
cagttcaact atctgccatg attattcttt tcacgtatca ttcattctgt acatttgtgt    5460
acattgagaa gtatagcaat ctatgtaaat gtaatcctca gtgaggttcc tcagtgctag    5520
gtcccatagg attgtcgttg cccttgttaa tgaggtttct ctgttcagcg gcttcaattt    5580
ttttctcttt gtacatctag ttttgaagat ttacttcaag tttgaatctt ctagaatgct    5640
tgtaagtcca gttttaattt ttagagtcaa tttgtagtta catgtagttt aacttttggg    5700
aaacgtctta acattgttct gaataaactt gctaatgagg tcaggtcatg gtacagactg    5760
atgcagtcaa catgatttca ttgcagagtt tattagtatc agcaagtttt tgctttgcta    5820
aataaaagta ctcaatgaac acaattctac ataaattttg acataccatc taatttataa    5880
```

| | |
|---|---|
| aaatcaataa aaaaggtttt ggtaaaactt tttcatgcca gatgctgttt acaacaatga | 5940 |
| acatgccaat aaaacatttg ttcattctgt tgtgttattt tagtcattaa acttctgtgg | 6000 |
| atgaagaatc tgggttaaga atagatttgt catctttaaa tatgacattt tgtaatgtgt | 6060 |
| attggatatc tcatttctat gataaaggta tatttacagt aaagttctca taagagaaat | 6120 |
| gaaaagctgt gttaatatct aactttgggg aaccctgtca gtatttcaga tccgattttt | 6180 |
| acccttttt tcttataaga aagataaaat tagaaaatac tgttagcaaa tgtggctctg | 6240 |
| ccatttgaat ataatcaccg agaattccat gtcttaaaag tctcctggaa tccacaatga | 6300 |
| aaaaaaaaat cttttctaag gtattttct ggctaatttt tatttgaaga aagctatagc | 6360 |
| atttagcgaa atttgactga agtaatgttc tgagtttgca ttagtgggat tggtgatgtt | 6420 |
| ctcagaagaa aattggaaac acttgtgatg aattgtcttt cagatcactt agattttctg | 6480 |
| atgtaagagg acagctgttt ggttctgata caggcctgct tacttgggat gtagggttag | 6540 |
| taaatggggt ttctgcttta aaggactgac ttgctatcac acaaaagagg cagacttgta | 6600 |
| aacacaatgg gctttggagt ttggtctgat tgggtttggt ttagtattcc tatgagcgta | 6660 |
| aatggtaaaa ttcttctgat acccactctt tagactgtgc cttctgctct gttctttgtt | 6720 |
| ttatgtttaa ctgctgtttc taattgcagg tgtattacag atacaaataa gagtaaagaa | 6780 |
| aatatatttc attatagaaa agaaaaaatt aaaagcttct tgcttttcag tgcctgatag | 6840 |
| agtgaaaaca caaagttgca ctttaataat ttcaataaaa gctaatctgt gtcagcctcc | 6900 |
| ctctgcttca gagagtcagg tgagcatcca taacctaaca ggcagagccc tagcgatgtg | 6960 |
| gatcaagttt cctgagcccg ggggcggtgg agcctcatga tctcttatct tttgaggctg | 7020 |
| aggcaggtca catgcaacaa attgtgaccc tgctccccac aagtcatgca aaggttttga | 7080 |
| agagcttta ccgtggggca gatgaacttg tgtcaaccat gcacaccctg tgagaaccaa | 7140 |
| gtacctgtgt ttctaaggcg ggcactcaag gtgaggggtg cattctggcc aaagaaacaa | 7200 |
| aagctgtggt ttcaggacca tgccgtgtgt agctgatctg tacgggacgt gtatgtaagg | 7260 |
| aagagcaatc atgatagata agaacagtgt gtgaagcagc cttcacacta gagtgtttgg | 7320 |
| tcatctctta taatgtaagg gaaggtactt taaaattctg ggaagatgcg atgaactcat | 7380 |
| gtcccagtca gaaaataatc caatgaaata agcattggtt gccaggccac agttaggaat | 7440 |
| tgtattgtga tacatctaga ggccaagaga gcaggagaga gctaccaact tacactgtgg | 7500 |
| tttaagctaa atgaccgcac agcatcatag cattgcagtg ttgttactaa atctggaagt | 7560 |
| gacctgtgaa tgtatggaat acaataaagt cttttattct ggttcatttg ctagtacttc | 7620 |
| ctttttgatt ggatactgta gttcttcctc tggattttat tttgttcagc gtcaaggccc | 7680 |
| taattttgca aatgtagtct aaaccacatt acgtggacta aggatactc tgaattagca | 7740 |
| agttttttgt ttgctgaata aaactattcc atcttaa | 7777 |

<210> SEQ ID NO 10
<211> LENGTH: 2417
<212> TYPE: DNA
<213> ORGANISM: Homo sapiens

<400> SEQUENCE: 10

| | |
|---|---|
| gcagcagaga ggagttgagg gcgatgagag cgggtactgc gaactgccgg gcgatgctgt | 60 |
| cgctgccgcc gtgatacgga gagcaacagt tccccagcaa caccctccc cgacacaggc | 120 |
| acacacccc cgacaggcac gcacacccac cccacagtgc ccggctcggc tgcgcctcct | 180 |
| ctattggccc aggaagccca cccagccccg ccacgcagag cccagaagga aagaaagcct | 240 |

```
catgcctgag ccgaggggag caccatggat ctgacaaaaa tgggcatgat ccagctgcag    300
aaccctagcc accccacggg gctactgtgc aaggccaacc agatgcggct ggccgggact    360
ttgtgcgatg tggtcatcat ggtggacagc caggagttcc acgcccaccg gacggtgctg    420
gcctgcacca gcaagatgtt tgagatcctc ttccaccgca atagtcaaca ctatactttg    480
gacttcctct cgccaaagac cttccagcag attctggagt atgcatatac agccacgctg    540
caagccaagg cggaggacct ggatgacctg ctgtatgcgg ccgagatcct ggagatcgag    600
tacctggagg aacagtgcct gaagatgctg agaccatcc aggcctcaga cgacaatgac    660
acggaggcca ccatggccga tggcggggcc gaggaagaag aggaccgcaa ggctcggtac    720
ctcaagaaca tcttcatctc gaagcattcc agcgaggaga gtgggtatgc cagtgtggct    780
ggacagagcc tccctgggcc catggtggac cagagccctt cagtctccac ttcatttggt    840
ctttcagcca tgagtcccac caaggctgca gtggacagtt tgatgaccat aggacagtct    900
ctcctgcagg gaactcttca gccacctgca gggcccgagg agccaactct ggctgggggt    960
gggcggcacc ctggggtggc tgaggtgaag acggagatga tgcaggtgga tgaggtgccc   1020
agccaggaca gccctgggc agccgagtcc agcatctcag agggatgggg ggacaaggtt   1080
gaggaaagag gcaaagaggg gcctgggacc ccgactcgaa gcagcgtcat caccagtgct   1140
agggagctac actatgggcg agaggagagt gccgagcagg tgccacccc agctgaggct   1200
ggccaggcc ccactggccg acctgagcac ccagcacccc cgcctgagaa gcatctgggc   1260
atctactccg tgttgcccaa ccacaaggct gacgctgtat tgagcatgcc gtcttccgtg   1320
acctctggcc tccacgtgca gcctgccctg gctgtctcca tggacttcag cacctatggg   1380
gggctgctgc cccagggctt catccagagg gagctgttca gcaagctggg ggagctggct   1440
gtgggcatga agtcagagag ccggaccatc ggagagcagt gcagcgtgtg tggggtcgag   1500
cttcctgata cgaggctgt ggagcagcac aggaagctgc acagtgggat gaagacgtac   1560
gggtgcgagc tctgcgggaa gcggttcctg gatagtttgc ggctgagaat gcacttactg   1620
gctcattcag cgggtgccaa agcctttgtc tgtgatcagt gcggtgcaca gttttcgaag   1680
gaggatgccc tggagacaca caggcagacc catactggca ctgacatggc cgtcttctgt   1740
ctgctgtgtg ggaagcgctt ccaggcgcag agcgcactgc agcagcacat ggaggtccac   1800
gcgggcgtgc gcagctacat ctgcagtgag tgcaaccgca ccttcccag ccacacggct   1860
ctcaaacgcc acctgcgctc acatacaggc gaccacccct acgagtgtga gttctgtggc   1920
agctgcttcc gggatgagag cacactcaag agccacaaac gcatccacac gggtgagaaa   1980
ccctacgagt gcaatggctg tgcaagaag ttcagcctca gcatcagct ggagacgcac   2040
tatagggtgc acacaggtga aagccccttt gagtgtaagc tctgccacca gcgctcccgg   2100
gactactcgg ccatgatcaa gcacctgaga acgcacaacg cgcctcgcc ctaccagtgc   2160
accatctgca cagagtactg ccccagcctc tcctccatgc agaagcacat gaagggccac   2220
aagcccgagg agatcccgcc cgactggagg atagagaaga cgtacctcta cctgtgctat   2280
gtgtgaaggg aggcccgcgg cggtggagcc gagcggggag ccaggaaaga agagttggag   2340
tgagatgaag gaaggactat gacaaataaa aaggaaaag aaaaaaaaaa acagaaggaa   2400
aaggaaaaaa aaaaaaa                                                  2417
```

<210> SEQ ID NO 11
<211> LENGTH: 1685
<212> TYPE: DNA

<213> ORGANISM: Homo sapiens

<400> SEQUENCE: 11

| | | | | | |
|---|---|---|---|---|---|
| cgcgaacccg | cgcgctgccc | ggtcctgcgc | tgctcagcgg | gaggggctgg | accccgcgtt | 60 |
| cctcctccct | gccggtcccc | atccttaaag | cgagagtctg | gacgcccgc | ctgtgggaga | 120 |
| gagcgccggg | atccggacgg | ggagcaaccg | gggcaggccg | tgccggctga | ggaggtcctg | 180 |
| aggctacaga | gctgccgcgg | ctggcacacg | agcgcctcgg | cactaaccga | gtgttcgcgg | 240 |
| gggctgtgag | gggagggccc | cgggcgccat | tgctggcggt | gggagcgccg | cccggtctca | 300 |
| gcccgccctc | ggctgctctc | ctcctccggc | tgggaggggc | cgtagctcgg | ggccgtcgcc | 360 |
| agccccggcc | cgggctcgag | aatcaagggc | ctcggccgcc | gtcccgcagc | tcagtccatc | 420 |
| gcccttgccg | ggcagcccgg | gcagagacca | tgtttgacaa | gacgcggctg | ccgtacgtgg | 480 |
| ccctcgatgt | gctctgcgtg | ttgctggctg | gattgccttt | tgcaattctt | acttcaaggc | 540 |
| atacccccctt | ccaacgagga | gtattctgta | atgatgagtc | catcaagtac | ccttacaaag | 600 |
| aagacaccat | accttatgcg | ttattaggtg | aataatcat | tccattcagt | attatcgtta | 660 |
| ttattcttgg | agaaaccctg | tctgtttact | gtaacctttt | gcactcaaat | tcctttatca | 720 |
| ggaataacta | catagccact | atttacaaag | ccattggaac | cttttttattt | ggtgcagctg | 780 |
| ctagtcagtc | cctgactgac | attgccaagt | attcaatagg | cagactgcgg | cctcacttct | 840 |
| tggatgttg | tgatccagat | tggtcaaaaa | tcaactgcag | cgatggttac | attgaatact | 900 |
| acatatgtcg | agggaatgca | gaaagagtta | aggaaggcag | gttgtccttc | tattcaggcc | 960 |
| actcttcgtt | ttccatgtac | tgcatgctgt | ttgtggcact | ttatcttcaa | gccaggatga | 1020 |
| agggagactg | ggcaagactc | ttacgccca | cactgcaatt | tggtcttgtt | gccgtatcca | 1080 |
| tttatgtggg | cctttctcga | gtttctgatt | ataaacacca | ctggagcgat | gtgttgactg | 1140 |
| gactcattca | gggagctctg | gttgcaatat | tagttgctgt | atatgtatcg | gatttcttca | 1200 |
| aagaaagaac | ttcttttaaa | gaagaaaag | aggaggactc | tcatacaact | ctgcatgaaa | 1260 |
| caccaacaac | tgggaatcac | tatccgagca | atcaccagcc | ttgaaaggca | gcagggtgcc | 1320 |
| caggtgaagc | tggcctgttt | tctaaaggaa | aatgattgcc | acaaggcaag | aggatgcatc | 1380 |
| tttcttcctg | gtgtacaagc | cttaaagac | ttctgctgct | gctatgcctc | ttggatgcac | 1440 |
| actttgtgtg | tacatagtta | cctttaactc | agtggttatc | taatagctct | aaactcatta | 1500 |
| aaaaaactcc | aagccttcca | ccaaaacagt | gccccacctg | tatacatttt | tattaaaaaa | 1560 |
| atgtaatgct | tatgtataaa | catgtatgta | atatgctttc | tatgaatgat | gtttgattta | 1620 |
| aatataatac | atattaaaat | gtatgggaga | accaaatcca | cacttgcaaa | aaaaaaaaa | 1680 |
| aaaaa | | | | | | 1685 |

<210> SEQ ID NO 12
<211> LENGTH: 6972
<212> TYPE: DNA
<213> ORGANISM: Homo sapiens

<400> SEQUENCE: 12

| | | | | | |
|---|---|---|---|---|---|
| gagagtccgg | ggatcccggg | ggccagtcgc | ggccgggaca | tcgggcgctg | cggccgggga | 60 |
| cccgctgctg | agatagacag | aatatggcag | agctttctga | gccagaggga | ccagtagatt | 120 |
| ggaaggaacg | atgtgtagct | ctggagtccc | aactcatgaa | atttagagtt | caagcaagca | 180 |
| agatacgaga | gcttttagca | gagaagatgc | aacagcttga | gagacaagtt | attgatgctg | 240 |
| aacgtcaagc | agaaaaagct | tttcaacagg | tacaagttat | ggaagataaa | ttaaaagcag | 300 |

```
ctaatattca aaccagtgaa tcagagacaa gattatataa taagtgtcaa gatctggagt    360
cgctaataca ggaaaaagat gacgtcattc aaaacttgga attgcaactt gaagagcaga    420
aacaaataag aatacaagaa gctaaaataa tagaagagaa agcagctaag ataaaagaat    480
gggtaacagt taagttaaat gagctggaat tggagaatca gaatcttcgt ttgatcaacc    540
aaaaccaaac tgaagagata agaacaatgc agtcaaaact acaagaagtt caaggaaaga    600
agtcatccac tgtctctaca ctaaagcttt cggaaggcca gcgcctgagc agtttgacct    660
ttgggtgctt tttatctcga gcaaggagtc ctcctcaagt agtaaaatct gaggaaatga    720
gcaagatatc atcgaaagaa cctgagttca ctgaaggaaa agacatggaa gaaatggaaa    780
ttccagaaaa gtctgttgat aaccaagttc tagaaaacaa cagaggccag agaacattgc    840
atcaaacccc ttgtggctca gaacagaatc ggaaaacaag aacaagcttt gcccacagatg   900 gtggcatctc ccagaattct ggggctcctg tgagtgactg gagctctgat gaggaagacg    960
ggagcaaagg aagatccaag tccagatgca catccaccct ctccagtcac acatctgagg   1020
aaggggtcca gtgtagcagg atgggaagtg aaatgtatct gacagcatct gatgacagca   1080
gctctatatt tgaggaagag acttttggca taaagagacc agaacacaag aagctatatt   1140
cttggcagca ggaggcacag tggaaagctc taaatagtcc tcttggaaag ggaaattctg   1200
aattaagtaa aaaggaacaa gatagttcct cggatgaact gaataaaaaa tttcaatccc   1260
agagactcga ttattcatct tcatcgagtg aagccaacac cccaagccct attttgaccc   1320
cagctttaat gccaaagcat cctaactcac tctctggaaa aggaacacaa ttagtgcctt   1380
catcacacct gccaccccca agttaagga ttcctaatgt tttcagtata agtgtagcac   1440
tagccaaaag gcacttaagc cagccacagt taagctctga caggatgttt ggtacaaata   1500
gaaacgctat aagcatgata cgaccactga gacctcagga aactgatctt gatctagttg   1560
atggagacag tacagaagtt ttagagaata tggacgcgag ttgtgatgat ggattatttt   1620
cctatgactc cttggactct ccaaattcag atgaccagga acactgtgac tcagcaaaga   1680
aggtggcata cagcaaacct ccaactcctc ccctgcaccg ttttccttct tgggaaagca   1740
gaatttatgc tgtagccaaa tcaggtattc gaatgtctga ggccttcaat atggagagtg   1800
ttaataaaaa ttctgctgca acccttttcct atactacatc aggactttat acatctctga   1860
tatacaagaa catgaccacc ccagtgtata caactttgaa ggggaaggcg acccaaataa   1920
gtagcagccc tttcctggat gactcatctg ggtcagagga agaagacagc tccagatcca   1980
gctcccggac gtcagagtca gactcacgca gtaggagtgg gccaggcagc cccagagcca   2040
tgaaacgagg tgtgtctctc tcctctgtgg cttctgaaag tgattatgct attcctcctg   2100
atgcttactc cacagacacg gagtactcac agccagagca gaagctccca aaaacttgct   2160
catcttccag tgataatggg aaaaatgaac cactggaaaa atctggttat ttattaaaaa   2220
tgagtggtaa agtcaagtct tggaagcggc ggtggttttgt tcttaaaggt ggtgaattac   2280
tttactacaa atctccgagt gatgtaatta gaaaacccca gggccatatt gaacttagtg   2340
catcctgtag tattttaaga ggagataaca acaaacagt tcagttgacc actgaaaaac   2400
acacatacta tctgactgca gattctccca atatattgga gagtggatt aaagtgttac   2460 agaatgttct tcgagtacaa gctgccaacc cactttccct gcagcctgag ggcaaaccca   2520
ccatgaaggg attgctcact aaggtaaaac atggatattc caagagagtc tggtgtacac   2580
taataggaaa gacattatat tattttcgga gtcaagaaga taagtttcct ttaggtcaga   2640
```

```
tcaaactctg ggaggctaaa gtggaagagg ttgacagatc ttgtgattca gatgaagatt      2700
atgaagccag tggacgaagt ctgttatcca cacattatac tatcgttatc catcccaaag      2760
accaaggtcc aacttacctc ctaattggat ccaagcatga aaaggacact tggctttatc      2820
atctgactgt tgcagctgga agcaacaatg taaacgttgg atctgaattt gaacaactgg      2880
tttgcaaatt gctaaatata gacggggagc cttcctctca gatatggaga cacccccactt     2940 tgtgtcacag taaagaagga atcatttccc ctctgacaac tctaccttcc gaagccctgc      3000
agacagaagc tattaaatta tttaagacct gccagctttt tataaatgct gcagttgact      3060
ctcctgcaat tgattaccac atatctttag cccagagtgc tttgcaaatc tgcctgacac      3120
atcctgagct gcagaatgaa atttgctgtc agcttattaa acagacaaga cgaagacagc      3180
cacagaatca accaggacca ttgcagggct ggcagctctt ggcactctgc gttgggctct      3240
tccttcccca tcatcctttc ctgtggctcc tcaggcttca cctaaagagg aatgcagatt      3300
ccaggacaga atttgaaaaa tatgccattt actgccagcg ttgtgtagaa agaacgcaac      3360
aaaatggtga cagagaagca agaccctcaa ggatggaaat tctttcaact cttctccgaa      3420
acccttatca ccattctttg ccctttagta tacctgtgca cttcatgaat gggatatacc      3480
aggtagttgg ttttgacgca tctaccacag tggaagaatt tttgaatact ttgaaccagg      3540
acacaggaat gaggaaacca gcgcagtctg gatttgcgtt gttcactgac gatccttctg      3600
gcagagattt agagcattgt cttcaaggaa acatcaagat ttgtgacatt atttccaaat      3660
gggaacaggc ttccaaagaa cagcagcctg gaaaatgtga aggtacaagg actgttcgtc      3720
tgacatacaa aaacagacta tatttctcag tgcaagctcg tggagagact gatagagaaa      3780
agttgctgtt aatgtatcag acaaatgatc aaatcataaa tggacttttt cctctgaaca      3840
aagatctggc attagaaatg gcagctcttt tatctcaggt agagattgga gattttgaaa      3900
gacctttctc aactccagca gggcatgtta ccaatcagtg caaagtgaat caaactctaa      3960
agcaagtcat agagaaattt tatcctaaaa ggtatagaga tggctgttct gaagagcagt      4020
taaggcagct ttgccagcga cttttcaacca gatggatggc cctccgggga cacagtgctg      4080
ctgactgtgt gcgcatttat ttgacagtag ccaggaagtg gccattcttt ggtgccaagt      4140
tgtttcttgc aaaacccata actccatcat cacttggaag tactttcttg tggctggctg      4200
tacatgagga tggtttaagc ctcttagaat acaactccat gaggttaata gtcagctatg      4260
tgtacaagag tctaatgacc tttggaggct atcaagatga ttttatggta gtcattaaca      4320
atacacattc aaaggacaaa ccaacagaga aattactttt tgccatggca aaacccaaga      4380
ttcttgaaat cactcttttg atcgccagtt acataaacaa cttccatcag caaaaggcag      4440
catttcacca cctctctgct ccagcactgc tctcagccca gacccgggga ccccaagcca      4500
gaatgatggg aagccagcct cttctgtcaa gcagcagacc gaccaaaggc cccaccttac      4560
tctgaaagct ggggagcctg aacattcact ccttgtcctc catgctgtgg ctgtatcagc      4620
tccctacaag ttcgtttaca cctggcagca cggcagccac acaccggtat tccaaaccttt     4680 aacaatgaag ggggttagtc tcttttattt gattcttaaa tattcaaata aatattaaca      4740
gtaaaacata aacacaaaat ttgccaacac actaattttc ttatagagta aatgagtaag      4800
aattcatcat ttttttccatc tcccttctcc cttgtcatca gacacattgt gcaatgtggc      4860
ttttcttttc ttttcttttt ttccccttttt taatattctg gcaatcttta gaaagggaga      4920
ttccaaactc ccatttggta aaccagttga ttatttggaa atgttcactg ccaaaatagt      4980
aagtgctata actaaatgcg cttttaatta atgatatagt gtttggaaag gagtagaaca      5040
```

-continued

```
tgcagcataa gaaactgctg cagagtggtg cgaggagtac attttcagag caggtgcagt    5100
acatcttccg gctctatgaa tcattatgtg agaaagcagg ataacattag gtaacctgag    5160
cctcctgtgt ggtattagaa agtataccgt cacctttca catcactgga gtgtaaaatt     5220
taaaacaaga tggtgattcc tgacattcct tggctgtcag tgctgcccag attcagaaga    5280
atattgccca catttcactg tatttggtgc tgggtcattt tgaccttgct tgttaataa     5340 tatctttaaa aacaaagaca atccttaaag ctttgctcct cacacattac cttctaatta    5400
tagtttgaaa atagattccc tacacataca tacatatgta tgcacagata gggtcttgct    5460
atgttgccca ggctggtctt gaactcctgg cctcaagcaa tcctctctcc tcagcctccc    5520
aaagtgctgg gattacaagt gtgagccacc acacctggct ccagaaattt tattttattt    5580
ttttgaggca gggtctcact ctggttgccc aggctggagt gcagtggtgc catcatagct    5640
cactgtagcc tcgaccttcc gggatcaagc aatcccactt cagcctcttg aatagctggg    5700
actagaagca tgcaccacca tgcccatcta atatttgtat tttagtaga  acaggatct     5760 ccctatgttg tccagcctag tctcaaactc ctgggttcaa gcaatcctcc cacctcggcc    5820
tcccaaagtg ctgggattgc aggcatgagc accgtgccc  agcctcaaaa atattttta    5880 aaagaaaaga gaaaataatt cttctgtcaa aggaggttaa attttagttg atagagtact    5940
taaatgcatt actttattag gttatgtaag tggtcagtgc attccagtat gtgtcacaac    6000
agtgtagttc atattcatga taaaaatgaa actgtgataa gacatgaaaa ttatattatt    6060
aaaatgttca attgtaatgg taatcatgag tatacttaat tttatttatg tatagaatat    6120
ttgtatttat ttttttggaca tatatttatc actttgtcat tttttttaac caatttgaga    6180
aatgttagct gctgaattaa tttgttgccc gagccttcat attttcttct ttgctgcctt    6240
ctccctgtgg caatgtactg ttctcacatt aagccttta  aaaatgttcc atactgtatt    6300
agcatcctta gaagggacag aactaagaaa tacattgctc aaataatatt ttactttatt    6360
gataatgaca aaagaatat ttttaaacc ccatcaaaat agattcaat tgactgtttc        6420 ccctacatct tttgagccac agtcgcccat cgaataagca aatttgtttt tgagaataaa    6480
ctggtaacca gtttgtgatg actctcagaa gccttttggc tgggttacag aagagtttct    6540
aagttcctag agagccattt ataattagt tggtgagcca gaggcttgac agagctgtta     6600
cttatgtgtg agggctttat tctcaggcag tagtttattc atcatttggt aagcccctcc    6660
ccacactcct ctaatttaaa caagtagtga aggcttatct taaactgtgt agtaccttag    6720
acttggcatt tatttttgat agagcagaga taaatatttt tgatggaagg aaatcaattt    6780
tctgtaactg atgatgtgaa aattttattt tctgggaaat tatatagcca ttcaaaaatt    6840
caaagtatgt tattatgatt ggttacaaga gaataatgtt acatgtttaa ttgtaatatt    6900
tgtctcctat cattttcttc cctttcagtc ataataaatg atttacaaaa cccaaaaaaa    6960
aaaaaaaaaa aa                                                         6972
```